US011832907B2

(12) United States Patent
Mintz et al.

(10) Patent No.: US 11,832,907 B2
(45) Date of Patent: Dec. 5, 2023

(54) MEDICAL ROBOTICS SYSTEMS IMPLEMENTING AXIS CONSTRAINTS DURING ACTUATION OF ONE OR MORE MOTORIZED JOINTS

(71) Applicant: Auris Health, Inc., Redwood City, CA (US)

(72) Inventors: David Stephen Mintz, Los Altos Hills, CA (US); Bruce R. Woodley, Palo Alto, CA (US); Travis Michael Schuh, Los Altos, CA (US); Yanan Huang, Sunnyvale, CA (US); Matthew Reagan Williams, Walnut Creek, CA (US)

(73) Assignee: Auris Health, Inc., Redwood City, CA (US)

( * ) Notice: Subject to any disclaimer, the term of this patent is extended or adjusted under 35 U.S.C. 154(b) by 146 days.

(21) Appl. No.: 17/339,637

(22) Filed: Jun. 4, 2021

(65) Prior Publication Data
US 2021/0290324 A1  Sep. 23, 2021

Related U.S. Application Data

(63) Continuation of application No. 16/011,521, filed on Jun. 18, 2018, now Pat. No. 11,026,758.
(Continued)

(51) Int. Cl.
*A61B 34/30* (2016.01)
*B25J 9/16* (2006.01)
(Continued)

(52) U.S. Cl.
CPC .............. *A61B 34/35* (2016.02); *A61B 34/20* (2016.02); *A61B 34/25* (2016.02); *A61B 34/30* (2016.02);
(Continued)

(58) Field of Classification Search
None
See application file for complete search history.

(56) References Cited

U.S. PATENT DOCUMENTS

| 2,556,601 A | 6/1951 | Schofield |
| 2,566,183 A | 8/1951 | Forss |

(Continued)

FOREIGN PATENT DOCUMENTS

| CN | 101161426 A | 4/2008 |
| CN | 101500470 A | 8/2009 |

(Continued)

OTHER PUBLICATIONS

Mayo Clinic, Robotic Surgery, https://www.mayoclinic.org/tests-procedures/robotic-surgey/about/pac-20394974?p=1, downloaded from the internet on Jul. 12, 2018, 2 pp.

*Primary Examiner* — Ryan Rink
(74) *Attorney, Agent, or Firm* — Conley Rose, P.C.

(57) ABSTRACT

Certain aspects relate to systems and techniques for medical robotic systems that leverage a versatile, open kinematic chain together with a set of medical-procedure-specific software-controlled actuation constraints in order to perform a variety of medical procedures. The robotic system can be operated in a first mode by identifying a remote center and constraining the actuation of motorized joints to maintain intersection of at least an insertion axis with the remote center. The robotic system can be operated in a second mode by identifying a virtual rail position and constraining the actuation of motorized joints to maintain alignment of the insertion axis along the virtual rail.

23 Claims, 30 Drawing Sheets

Related U.S. Application Data

(60) Provisional application No. 62/525,963, filed on Jun. 28, 2017.

(51) Int. Cl.

| | | |
|---|---|---|
| *A61B 34/35* | (2016.01) | |
| *A61B 34/20* | (2016.01) | |
| *A61B 34/00* | (2016.01) | |
| *A61B 90/50* | (2016.01) | |
| *A61B 90/57* | (2016.01) | |
| *A61G 13/04* | (2006.01) | |
| *A61G 13/02* | (2006.01) | |
| *A61G 13/10* | (2006.01) | |
| *A61B 34/10* | (2016.01) | |
| *A61B 17/00* | (2006.01) | |
| *A61B 10/02* | (2006.01) | |
| *A61B 90/30* | (2016.01) | |
| *A61B 90/00* | (2016.01) | |

(52) U.S. Cl.
CPC .............. *A61B 34/70* (2016.02); *A61B 34/76* (2016.02); *A61B 90/50* (2016.02); *A61B 90/57* (2016.02); *A61G 13/02* (2013.01); *A61G 13/04* (2013.01); *A61G 13/10* (2013.01); *B25J 9/1676* (2013.01); *A61B 10/0233* (2013.01); *A61B 2017/00115* (2013.01); *A61B 2017/00809* (2013.01); *A61B 2034/105* (2016.02); *A61B 2034/2048* (2016.02); *A61B 2034/2051* (2016.02); *A61B 2034/2059* (2016.02); *A61B 2034/2065* (2016.02); *A61B 2034/305* (2016.02); *A61B 2090/306* (2016.02); *A61B 2090/3614* (2016.02); *A61B 2090/376* (2016.02); *A61B 2090/508* (2016.02); *A61B 2090/571* (2016.02)

(56) References Cited

U.S. PATENT DOCUMENTS

| | | |
|---|---|---|
| 2,623,175 A | 12/1952 | Finke |
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,784,031 A | 1/1974 | Nitu |
| 3,790,002 A | 2/1974 | Guilbaud et al. |
| 3,921,536 A | 11/1975 | Savage |
| 3,926,386 A | 12/1975 | Stahmann |
| 4,141,245 A | 2/1979 | Brandstetter |
| 4,241,864 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,857,058 A | 8/1989 | Payton |
| 4,907,168 A | 3/1990 | Boggs |
| 4,945,790 A | 8/1990 | Golden |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,350,101 A | 9/1994 | Godlewski |
| 5,426,687 A | 6/1995 | Goodall et al. |
| 5,507,725 A | 4/1996 | Savage et al. |
| 5,524,180 A | 6/1996 | Wang et al. |
| 5,559,294 A | 9/1996 | Hoium et al. |
| 5,709,661 A | 1/1998 | Van Egmond |
| 5,767,840 A | 6/1998 | Selker |
| 5,779,623 A | 7/1998 | Bonnell |
| 5,792,135 A | 8/1998 | Madhani et al. |
| 5,797,900 A | 8/1998 | Madhani |
| 5,842,390 A | 12/1998 | Bouligny |
| 5,855,583 A | 1/1999 | Wang et al. |
| 5,921,968 A | 7/1999 | Lampropoulos et al. |
| 5,967,934 A | 10/1999 | Ishida et al. |
| 6,077,219 A | 6/2000 | Viebach |
| 6,084,371 A | 7/2000 | Kress et al. |
| 6,154,000 A | 11/2000 | Rastegar et al. |
| 6,171,234 B1 | 1/2001 | White et al. |
| 6,185,478 B1 | 2/2001 | Koakutsu et al. |
| 6,272,371 B1 | 8/2001 | Shlomo |
| 6,289,579 B1 | 9/2001 | Viza et al. |
| 6,394,998 B1 | 5/2002 | Wallace et al. |
| 6,401,572 B1 | 6/2002 | Provost |
| 6,436,107 B1 | 8/2002 | Wang et al. |
| 6,487,940 B2 | 12/2002 | Hart et al. |
| 6,491,701 B2 | 12/2002 | Tierney et al. |
| 6,659,939 B2 | 12/2003 | Moll et al. |
| 6,695,818 B2 | 2/2004 | Wollschlager |
| 6,726,675 B1 | 4/2004 | Beyar |
| 6,786,896 B1 | 9/2004 | Madhani et al. |
| 6,827,712 B2 | 12/2004 | Tovey et al. |
| 7,044,936 B2 | 5/2006 | Harding |
| 7,172,580 B2 | 2/2007 | Hruska et al. |
| 7,248,944 B2 | 7/2007 | Green |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,938,809 B2 | 5/2011 | Lampropoulos et al. |
| 7,972,298 B2 | 7/2011 | Wallace et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,157,308 B2 | 4/2012 | Pedersen |
| 8,182,415 B2 | 5/2012 | Larkin et al. |
| 8,277,417 B2 | 10/2012 | Fedinec et al. |
| 8,291,791 B2 | 10/2012 | Light et al. |
| 8,414,505 B1 | 4/2013 | Weitzner |
| 8,425,465 B2 | 4/2013 | Nagano |
| 8,541,970 B2 | 9/2013 | Nowlin |
| 8,671,817 B1 | 3/2014 | Bogusky |
| 8,720,448 B2 | 5/2014 | Reis et al. |
| 8,746,252 B2 | 6/2014 | McGrogan et al. |
| 8,870,815 B2 | 10/2014 | Bhat et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,173,713 B2 | 11/2015 | Hart et al. |
| 9,204,933 B2 | 12/2015 | Reis et al. |
| 9,259,280 B2 | 2/2016 | Au |
| 9,259,281 B2 | 2/2016 | Griffiths |
| 9,326,822 B2 | 5/2016 | Lewis et al. |
| 9,408,669 B2 | 8/2016 | Kokish et al. |
| 9,446,177 B2 | 9/2016 | Millman et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |

(56) References Cited

U.S. PATENT DOCUMENTS

| | | |
|---|---|---|
| 9,818,681 B2 | 11/2017 | Machida |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco |
| 10,016,900 B1 | 7/2018 | Meyer et al. |
| 10,022,192 B1 | 7/2018 | Ummalaneni |
| 10,143,360 B2 | 12/2018 | Roelle et al. |
| 10,145,747 B1 | 12/2018 | Lin et al. |
| 10,159,532 B1 | 12/2018 | Ummalaneni et al. |
| 10,258,285 B2 | 4/2019 | Hauck |
| 10,285,574 B2 | 5/2019 | Landey et al. |
| 10,299,870 B2 | 5/2019 | Connolly et al. |
| 10,426,559 B2 | 10/2019 | Graetzel et al. |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,517,692 B2 | 12/2019 | Eyre et al. |
| 10,524,866 B2 | 1/2020 | Srinivasan |
| 10,539,478 B2 | 1/2020 | Lin |
| 10,555,778 B2 | 2/2020 | Ummalaneni et al. |
| 10,639,114 B2 | 5/2020 | Schuh |
| 10,667,875 B2 | 6/2020 | DeFonzo |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,820,954 B2 | 11/2020 | Marsot et al. |
| 10,888,386 B2 | 1/2021 | Eyre |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0056561 A1 | 3/2003 | Butscher et al. |
| 2003/0167623 A1 | 9/2003 | Lorenz |
| 2003/0212308 A1 | 11/2003 | Bendall |
| 2004/0015053 A1 | 1/2004 | Bieger |
| 2004/0152972 A1 | 8/2004 | Hunter |
| 2004/0243147 A1 | 12/2004 | Lipow |
| 2004/0254566 A1 | 12/2004 | Plicchi |
| 2005/0004579 A1 | 1/2005 | Schneider et al. |
| 2005/0177026 A1 | 8/2005 | Hoeg et al. |
| 2005/0183532 A1 | 8/2005 | Najaf et al. |
| 2005/0222554 A1 | 10/2005 | Wallace et al. |
| 2006/0041245 A1 | 2/2006 | Ferry |
| 2006/0111692 A1 | 5/2006 | Hlavka et al. |
| 2006/0142657 A1 | 6/2006 | Quaid |
| 2006/0146010 A1 | 7/2006 | Schneider |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0100201 A1 | 5/2007 | Komiya et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0149946 A1 | 6/2007 | Viswanathan |
| 2007/0185485 A1 | 8/2007 | Hauck et al. |
| 2007/0191177 A1 | 8/2007 | Nagai et al. |
| 2007/0239028 A1 | 10/2007 | Houser |
| 2007/0245175 A1 | 10/2007 | Zheng et al. |
| 2007/0299427 A1 | 12/2007 | Yeung et al. |
| 2008/0039255 A1 | 2/2008 | Jinno et al. |
| 2008/0046122 A1 | 2/2008 | Manzo et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers et al. |
| 2008/0300592 A1 | 12/2008 | Weitzner et al. |
| 2008/0302200 A1 | 12/2008 | Tobey |
| 2009/0005768 A1 | 1/2009 | Sharareh |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0163948 A1 | 6/2009 | Sunaoshi |
| 2009/0171371 A1 | 7/2009 | Nixon |
| 2009/0247944 A1 | 10/2009 | Kirschenrnan et al. |
| 2009/0248039 A1 | 10/2009 | Cooper et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0082041 A1 | 4/2010 | Prisco |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2010/0249506 A1 | 9/2010 | Prisco et al. |
| 2010/0274078 A1 | 10/2010 | Kim et al. |
| 2010/0332033 A1 | 12/2010 | Diolaiti |
| 2011/0009863 A1 | 1/2011 | Stanislaw |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028790 A1 | 2/2011 | Farr et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071621 A1 | 3/2012 | Yu |
| 2012/0071894 A1 | 3/2012 | Tanner et al. |
| 2012/0071895 A1 | 3/2012 | Stahler et al. |
| 2012/0132018 A1 | 5/2012 | Tang |
| 2012/0136419 A1 | 5/2012 | Zarembo et al. |
| 2012/0143226 A1 | 6/2012 | Beison et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0217457 A1 | 8/2012 | Schena et al. |
| 2012/0232476 A1 | 9/2012 | Bhat et al. |
| 2012/0239012 A1 | 9/2012 | Laurent et al. |
| 2012/0277730 A1 | 11/2012 | Salahieh |
| 2012/0283747 A1 | 11/2012 | Popovic |
| 2013/0018400 A1 | 1/2013 | Milton et al. |
| 2013/0066335 A1 | 3/2013 | Barwinkel |
| 2013/0144116 A1 | 6/2013 | Cooper et al. |
| 2013/0204124 A1 | 8/2013 | Duindam |
| 2013/0226151 A1 | 8/2013 | Suehara |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0066944 A1 | 3/2014 | Taylor et al. |
| 2014/0069437 A1 | 3/2014 | Reis et al. |

(56) References Cited

U.S. PATENT DOCUMENTS

| | | |
|---|---|---|
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0180063 A1 | 6/2014 | Zhao |
| 2014/0222019 A1 | 8/2014 | Brudnick |
| 2014/0243849 A1 | 8/2014 | Saglam et al. |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0277334 A1 | 9/2014 | Yu et al. |
| 2014/0309649 A1 | 10/2014 | Alvarez et al. |
| 2014/0357984 A1 | 12/2014 | Wallace et al. |
| 2014/0364670 A1 | 12/2014 | Alvarez et al. |
| 2014/0375784 A1 | 12/2014 | Massetti |
| 2014/0379000 A1 | 12/2014 | Romo et al. |
| 2015/0012134 A1 | 1/2015 | Robinson |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119637 A1 | 4/2015 | Alvarez |
| 2015/0119638 A1 | 4/2015 | Yu et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0231364 A1 | 8/2015 | Blanchard |
| 2015/0297864 A1 | 10/2015 | Kokish et al. |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0000512 A1 | 1/2016 | Gombert et al. |
| 2016/0001038 A1 | 1/2016 | Romo et al. |
| 2016/0157945 A1 | 6/2016 | Madhani |
| 2016/0166234 A1 | 6/2016 | Zhang |
| 2016/0192860 A1 | 7/2016 | Allenby |
| 2016/0206389 A1 | 7/2016 | Miller |
| 2016/0213435 A1 | 7/2016 | Hourtash |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2017/0007337 A1 | 1/2017 | Dan |
| 2017/0007343 A1 | 1/2017 | Yu |
| 2017/0020615 A1 | 1/2017 | Koenig et al. |
| 2017/0071684 A1 | 3/2017 | Kokish et al. |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0258534 A1 | 9/2017 | Hourtash |
| 2017/0281049 A1 | 10/2017 | Yamamoto |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0325932 A1 | 11/2017 | Hoelzle |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0042686 A1 | 2/2018 | Peine |
| 2018/0049792 A1 | 2/2018 | Eckert |
| 2018/0056044 A1 | 3/2018 | Chol et al. |
| 2018/0104820 A1 | 4/2018 | Troy et al. |
| 2018/0116735 A1 | 5/2018 | Tierney et al. |
| 2018/0168681 A1 | 6/2018 | Kirk et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0206927 A1 | 7/2018 | Prisco et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0243048 A1 | 8/2018 | Shan |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0110839 A1 | 4/2019 | Rafii-Tari et al. |
| 2019/0125465 A1 | 5/2019 | Evans et al. |
| 2019/0142537 A1 | 5/2019 | Covington et al. |
| 2019/0151148 A1 | 5/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafil-Tari et al. |
| 2019/0183587 A1 | 6/2019 | Rafii-Tari et al. |
| 2019/0191967 A1 | 6/2019 | Yamamoto et al. |
| 2019/0216548 A1 | 7/2019 | Ummalaneni |
| 2019/0216576 A1 | 7/2019 | Eyre |
| 2019/0223967 A1 | 7/2019 | Abbott |
| 2019/0223974 A1 | 7/2019 | Romo |
| 2019/0228525 A1 | 7/2019 | Mintz et al. |
| 2019/0231458 A1 | 8/2019 | DiMaio |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0008874 A1 | 1/2020 | Barbagli |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |

(56) References Cited

U.S. PATENT DOCUMENTS

| | | |
|---|---|---|
| 2020/0107894 A1 | 4/2020 | Wallace |
| 2020/0121502 A1 | 4/2020 | Kintz |
| 2020/0129252 A1 | 4/2020 | Kokish |
| 2020/0146769 A1 | 5/2020 | Eyre |
| 2020/0155245 A1 | 5/2020 | Yu |
| 2020/0155801 A1 | 5/2020 | Kokish |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0230360 A1 | 7/2020 | Yu |
| 2020/0237458 A1 | 7/2020 | DeFnzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0040542 A1 | 12/2020 | Schuh |
| 2020/0375678 A1 | 12/2020 | Wallace |
| 2020/0383735 A1 | 12/2020 | Lewis et al. |
| 2020/0405317 A1 | 12/2020 | Wallace |
| 2020/0405411 A1 | 12/2020 | Draper et al. |
| 2020/0405413 A1 | 12/2020 | Kokish |
| 2020/0405419 A1 | 12/2020 | Mao |
| 2020/0405420 A1 | 12/2020 | Purohit |
| 2020/0405423 A1 | 12/2020 | Schuh |
| 2020/0405434 A1 | 12/2020 | Schuh |
| 2020/0406002 A1 | 12/2020 | Romo |
| 2021/0007819 A1 | 1/2021 | Schuh |
| 2021/0008341 A1 | 1/2021 | Landey et al. |

FOREIGN PATENT DOCUMENTS

| | | |
|---|---|---|
| CN | 102015759 A | 4/2011 |
| CN | 201884596 U | 6/2011 |
| CN | 102316817 A | 1/2012 |
| CN | 102327118 A | 1/2012 |
| CN | 102458295 A | 5/2012 |
| CN | 102665590 A | 9/2012 |
| CN | 102834043 A | 12/2012 |
| CN | 102973317 A | 3/2013 |
| CN | 103037799 A | 4/2013 |
| CN | 103735313 A | 4/2014 |
| CN | 105147393 A | 12/2015 |
| CN | 105559850 A | 5/2016 |
| CN | 105559886 A | 5/2016 |
| DE | 19649082 C1 | 1/1998 |
| DE | 102004020465 B3 | 9/2005 |
| EP | 1442720 | 8/2004 |
| EP | 2567670 | 3/2013 |
| EP | 3025630 | 6/2016 |
| JP | 07136173 | 5/1995 |
| JP | H07136173 A | 5/1995 |
| JP | 2009139187 A | 6/2009 |
| JP | 2010046384 A | 3/2010 |
| JP | 2014159071 A | 9/2014 |
| WO | WO-1994014494 A2 | 7/1994 |
| WO | WO-1996022591 A1 | 7/1996 |
| WO | WO-2002074178 A2 | 9/2002 |
| WO | WO-2007088208 A1 | 8/2007 |
| WO | WO-2007146987 A2 | 12/2007 |
| WO | WO-2009092059 A2 | 7/2009 |
| WO | WO-2011005335 A1 | 1/2011 |
| WO | WO-2012037506 A2 | 3/2012 |
| WO | WO-2013179600 A1 | 12/2013 |
| WO | WO-2015127231 A1 | 8/2015 |
| WO | WO-2017059412 A1 | 4/2017 |
| WO | WO-2017151993 A1 | 9/2017 |
| WO | WO-2017156070 A1 | 9/2017 |
| WO | WO-2018094191 A1 | 5/2018 |

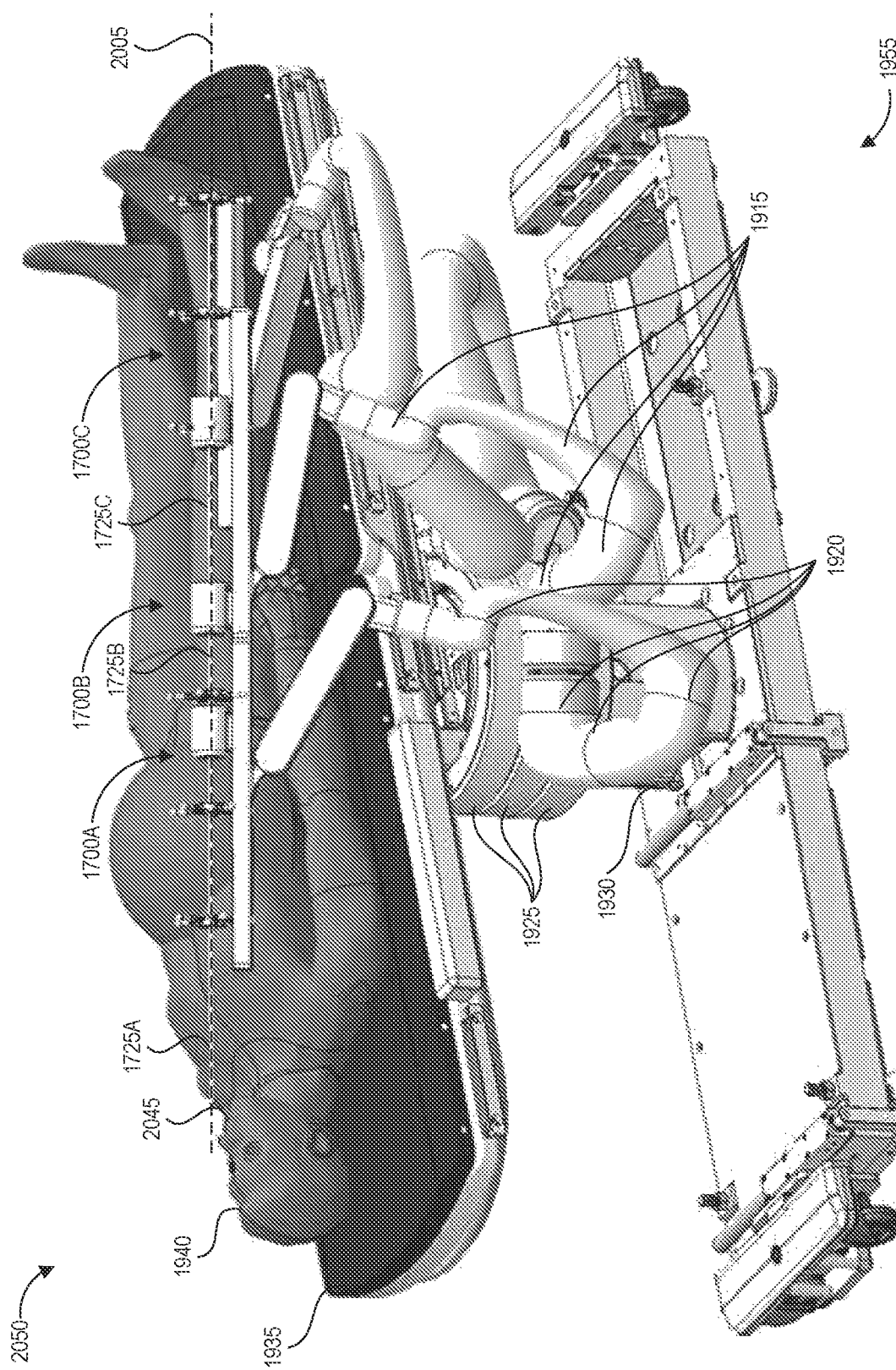

MEDICAL ROBOTICS SYSTEMS IMPLEMENTING AXIS CONSTRAINTS DURING ACTUATION OF ONE OR MORE MOTORIZED JOINTS

CROSS-REFERENCE TO RELATED APPLICATIONS

This application is a continuation of U.S. application Ser. No. 16/011,521, filed Jun. 18, 2018, which claims the benefit of and priority to U.S. Provisional Application No. 62/525,963, filed Jun. 28, 2017, the entireties of each of which are hereby incorporated by reference in their entirety.

TECHNICAL FIELD

The systems and methods disclosed herein are directed to medical devices, and more particularly to robotic systems.

BACKGROUND

Robotic systems can assist physicians in performing medical procedures. Various medical procedures involve localization of a three-dimensional position of a medical instrument within a patient's body in order to provide diagnosis and/or treatment. Articulated robotic arms can be operated under the control of a physician, partially autonomously, or completely autonomously to position the medical instrument at the correct location. Due to use of robotic systems, procedures may be performed with greater precision, smaller incisions, decreased blood loss, and quicker healing time, to name a few examples.

SUMMARY

One challenge with medical robotic systems is that there are a wide variety of medical procedures, with each procedure having its own set of kinematic requirements for a robotic arm usable during the procedure. For instance, the requirements for robotic-assisted endoscopy differ from the requirements for robotic-assisted laparoscopy with respect to system bandwidth, stiffness, workspace range and positioning, and speeds, among other differences. As a result, existing medical robotic systems are typically purpose-built for a specific medical procedure and are unable to perform other types of medical procedures. Accordingly, hospitals or other medical clinics seeking to use such robotic systems have increased costs relating to acquisition (e.g., purchase or rental) and storage of multiple systems. This can, in turn, result in increased costs passed on to patients undergoing such procedures.

The above described problems, among others, are addressed by the multipurpose robotics systems and associated operating techniques described herein. For example, a robotic arm according to the present disclosure includes a versatile kinematic chain and is controlled by computer-implemented instructions that enable the robotic arm to operate in a variety of modes, with different modes usable for different types of medical procedures. The kinematic chain includes a number of motorized joints coupled by linkages in a serial fashion, for example configured as an open chain serial link manipulator. A first motorized joint at the proximal end of the robotic arm (e.g., closest to setup joints or a base of the robotic system) is a revolute joint and a second motorized joint at the distal end of the robotic arm (e.g., closest to the medical instrument) is a prismatic joint, with a number of additional motorized joints positioned serially between the first and second motorized joints. The additional motorized joints can be either revolute or prismatic as explained in more detail below. As used herein, a revolute joint imparts rotary motion to a connected linkage, while a prismatic joint imparts linear motion to a connected linkage. In some embodiments, each joint of the robotic arm can include its own independently actuatable motor in order to achieve the disclosed operational modes.

The same robotic system, configured according to the present disclosure, can advantageously be used in various modes for different types of medical procedures based on computer-executable rules for controlling and/or constraining the motion of the various joints in the versatile kinematic chain. For example, a first mode may be suitable for use during a laparoscopic procedure. In laparoscopy, medical instruments are inserted through incisions in the abdominal wall to access the patient's internal organs. Accordingly, the instructions for operating the robotic system in the first mode can include identifying a remote center at or near the location of the incision, and constraining the actuation of the motorized joints to maintain intersection of at least an insertion axis with the remote center. This can mitigate or prevent undue stress to patient tissue around the incision during manipulation of the medical instrument. As used herein, a remote center can be considered as a fixed point around which the medical instrument rotates, with no physical revolute joint of the robotic system physically located at the remote center.

As another example, a second mode may be suitable for use during endoscopic procedures including bronchoscopy procedures, gastroscopy procedures, and ureteroscopy procedures, to name a few. In endoscopy, medical instruments are moved along an insertion axis aligned with a natural orifice of the patient, with some steerable instruments capable of articulation while inserted into the patient's body. Accordingly, the instructions for operating the robotic system in the second mode can include identifying a virtual position of a virtual rail such that the insertion axis along the virtual rail is aligned with the orifice, and actuating at least one of the motorized joints to control movement of the medical instrument along the virtual rail.

Accordingly, one aspect relates to a robotic system configured to perform medical procedures, the system comprising a robotic arm configured to control movement of a medical instrument with respect to at least first, second, and third axes, the robotic arm comprising a plurality of linkages serially coupling a plurality of motorized joints, the plurality of motorized joints including a first motorized joint comprising a revolute joint, the first motorized joint configured to actuate the movement of the medical instrument about the first axis, a second motorized joint comprising a prismatic joint configured to linearly translate the medical instrument along the second axis, and a plurality of additional motorized joints positioned serially between the first and second motorized joints, the plurality of additional motorized joints configured to actuate the movement of the medical instrument about the third axis; at least one computer-readable memory having stored thereon executable instructions for operating the robotic system in one of a first and second operating modes; and at least one processor in communication with the at least one computer-readable memory and configured to execute the instructions to cause the system to at least in response to receiving a command to operate in the first operating mode, (i) fix a location of a remote center such that the second axis is aligned with an opening of a patient and passes through the remote center, and (ii) constrain the motion of the plurality of motorized joints when actuated in the first operating mode such that the second axis passes through the remote center; and in response to receiving a command to operate in the second operating mode, (i) identify a positioning of a virtual rail based on positioning of the second axis when aligned with the opening of the patient, and (ii) control movement of the medical instrument along the virtual rail.

In some embodiments, each of the plurality of motorized joints comprises its own motor. In some embodiments, each of the plurality of motorized joints further comprises a position sensor configured to determine a position of a rotor of the motor. In some embodiments, the at least one processor is configured to execute the instructions to cause the system to at least control positioning of the robotic arm in the first and second operating modes based at least partly on the position of the rotor of the motor of each of the plurality of motorized joints.

In some embodiments, the at least one processor is configured to execute the instructions to cause the system to at least actuate the second motorized joint to move the medical instrument along the virtual rail. In some embodiments, the at least one processor is configured to execute the instructions to cause the system to at least coordinate actuation of two or more of the plurality of motorized joints to move the medical instrument along the virtual rail.

In some embodiments, the plurality of additional motorized joints comprise third, fourth, and fifth joints. In some embodiments, to constrain the motion of the plurality of motorized joints when actuated in the first operating mode, the at least one processor is configured to execute the instructions to cause the system to at least identify a virtual orientation of a virtual linkage between the remote center and the third joint; and maintain positioning of a linkage of the plurality of linkages coupling the fourth and fifth joints parallel with the virtual orientation of the virtual linkage. In some embodiments, the at least one processor is configured to execute the instructions to cause the system to at least change a distance between the remote center and the third joint. In some embodiments, the at least one processor is configured to execute the instructions to cause the system to at least fix a distance between the remote center and the third joint to be equal to a length of the linkage coupling the fourth and fifth joints.

In some embodiments, each of the third, fourth, and fifth joints comprises an additional revolute joint. In some embodiments, a first linkage of the plurality of linkages couples the first and third joints, a second linkage of the plurality of linkages couples the third and fourth joints, and a first length of the first linkage is longer than a second length of the second linkage. In some embodiments, the at least one processor is configured to execute the instructions to cause the system to at least rotate the third and fourth joints such that the fourth joint passes from a first position on a first side of the first linkage past the first joint to a position on a second side of the first linkage. In some embodiments, a third linkage of the plurality of linkages couples the fourth and fifth joints, with the first, second, and third linkages being configured to be positioned in a substantially parallel fashion with the second linkage positioned between the first and third linkages. In some embodiments, the at least one processor is configured to position the first, second, and third linkages in the substantially parallel fashion in response to receiving a storage command. In some embodiments, a fourth linkage couples the second and fifth joints, the fourth linkage configured to be substantially parallel with and adjacent to the third linkage.

In some embodiments, each of the third and fourth joints comprise first and second additional revolute joints and the fifth joint comprises an additional prismatic joint. In some embodiments, the additional prismatic joint is configured to move along an additional axis parallel to the second axis, wherein the at least one processor is configured to execute the instructions to cause the system to at least move the additional prismatic joint along the additional axis.

Some embodiments further comprise an instrument driver coupled to the second motorized joint and configured to manipulate the medical instrument, wherein the at least one processor is configured to execute the instructions to cause the system to at least actuate the instrument driver to manipulate the medical instrument. In some embodiments, the instrument driver is aligned along the second axis. Some embodiments further comprise at least one additional robotic arm coupled to an additional instrument driver, wherein the at least one processor is configured to execute the instructions to cause the system to at least, in response to receiving the command to operate in the second operating mode, align the additional instrument driver along the virtual rail. In some embodiments, the first axis comprises a yaw axis, the second axis comprises an insertion axis, and the third axis comprises a pitch axis, wherein the at least one processor is configured to execute the instructions to cause the system to at least actuate the instrument driver to control movement of the medical instrument about a roll axis. Some embodiments further comprise a docking port coupled to an end of a linkage of the plurality of linkages with the second motorized joint configured to linearly move along the linkage, wherein the docking port is configured to couple to a cannula holder configured to retain a cannula inserted into the opening of the patient when the robotic arm is operated in the first operating mode, and wherein the docking port is configured to couple to an additional instrument driver when the robotic arm is operated in the second operating mode.

Some embodiments further comprise a cannula holder coupled to a linkage of the plurality of linkages with the second motorized joint configured to linearly move along the linkage, wherein the at least one processor is configured to execute the instructions to cause the system to at least, in response to receiving the command to operate in the first operating mode identify that a cannula is docked to the cannula holder; determine the location of the remote center based at least partly on a location of the cannula holder; and cause the robotic arm and at least one setup joint coupled to the robotic arm to perform at least one null-space movement to align the first axis to pass through the remote center, wherein during the null-space movement at least one joint of the plurality of motorized joints and the at least one setup joint is actuated and the location of the cannula holder remains fixed. In some embodiments, after performing the at least one null-space movement, the at least one processor is configured to execute the instructions to cause the system to at least constrain the motion of the plurality of motorized joints in the first operating mode such that the first, second, and third axes pass through the remote center. In some embodiments, the at least one processor is configured to execute the instructions to cause the system to at least receive a command to adjust a distance between the position of the first motorized joint and the location of the remote center, and perform at least one null-space movement to adjust the distance by actuating at least one joint from the plurality of additional motorized joints while maintaining alignment of the first, second, and third axes through the remote center.

Some embodiments further comprise a setup joint coupled to the robotic arm, wherein a mechanical reach of the robotic arm extends throughout a workspace, and wherein the at least one processor is configured to execute the instructions to cause the system to at least actuate the setup joint to reposition the workspace of the robotic arm. In some embodiments, the at least one processor is configured to execute the instructions to cause the system to at least, in response to receiving the command to operate in the first operating mode, reposition the workspace of the robotic arm while performing null-space movement of the plurality of motorized joints such that the first, second, and third axes pass through the remote center. In some embodiments, the at least one processor is configured to execute the instructions to cause the system to at least, in response to receiving the command to operate in the second operating mode, reposition the workspace of the robotic arm while performing null-space movement of the plurality of motorized joints such that the second axis remains aligned with the opening of a patient.

Another aspect relates to a non-transitory computer readable storage medium having stored thereon instructions that, when executed, cause at least one computing device to at least receive a command to operate in one of a first operating mode and a second operating mode of controlling movement of a medical instrument with respect to at least first, second, and third axes via a robotic arm comprising a plurality of linkages serially coupling a plurality of motorized joints, the plurality of motorized joints including a first motorized joint comprising a revolute joint, the first motorized joint configured to actuate the movement of the medical instrument about the first axis, a second motorized joint comprising a prismatic joint configured to linearly translate the medical instrument along the second axis, and a plurality of additional motorized joints positioned serially between the first and second motorized joints, the plurality of additional motorized joints configured to actuate the movement of the medical instrument about the third axis; in response to receiving the command to operate in the first operating mode, (i) fix a location of a remote center such that the second axis is aligned with an opening of a patient and passes through the remote center, and (ii) constrain the motion of the plurality of motorized joints when actuated in the first operating mode such that the such that the second axis passes through the remote center; and in response to receiving the command to operate in the second operating mode, align a virtual rail coaxial with the second axis with the opening of the patient.

In some embodiments, each of the plurality of motorized joints comprises a motor having a rotor, and wherein the instructions, when executed, cause the at least one computing device to at least control positioning of the robotic arm in the first and second operating modes based at least partly on a position of the rotor of the motor of each of the plurality of motorized joints. In some embodiments, the instructions, when executed, cause the at least one computing device to at least, in response to receiving the command to operate in the second operating mode, (i) actuate at least some of the plurality of motorized joints to align the second axis with the opening of the patient, (ii) identify a positioning of a virtual rail based on positioning of the second axis when aligned with the opening of the patient, and (iii) control actuation of the medical instrument along the virtual rail.

In some embodiments, the instructions, when executed, cause the at least one computing device to at least, in response to receiving the command to operate in the first operating mode identify that a cannula is docked to a cannula holder coupled to a linkage of the plurality of linkages with the distal motorized joint configured to linearly move along the linkage; determine the location of the remote center based at least partly on a location of the cannula holder; and cause the robotic arm and at least one setup joint coupled to the robotic arm to perform at least one null-space movement to align the first axis to pass through the remote center, wherein during the null-space movement at least one joint of the plurality of motorized joints and the at least one setup joint is actuated and the location of the cannula holder remains fixed. In some embodiments, after performing the at least one null-space movement, the instructions, when executed, cause the at least one computing device to at least constrain the motion of the plurality of motorized joints in the first operating mode such that the first, second, and third axes pass through the remote center. In some embodiments, the instructions, when executed, cause the at least one computing device to at least receive a command to adjust a distance between the position of the first motorized joint and the location of the remote center; and perform at least one null-space movement to adjust the distance by actuating at least one of the plurality of motorized joints while maintaining alignment of the first, second, and third axes through the remote center. In some embodiments, the plurality of additional motorized joints comprise third, fourth, and fifth joints, and wherein the instructions to constrain the motion of the plurality of motorized joints when actuated in the first operating mode, when executed, cause the at least one computing device to at least identify a virtual orientation of a virtual linkage between the remote center and the third joint; and maintain positioning of a linkage of the plurality of linkages coupling the fourth and fifth joints parallel with the virtual orientation of the virtual linkage.

In some embodiments, a mechanical reach of the robotic arm extends throughout a workspace, and wherein the instructions, when executed, cause the at least one computing device to at least actuate a setup joint coupled to the robotic arm to reposition the workspace of the robotic arm. In some embodiments, the instructions, when executed, cause the at least one computing device to at least, in response to receiving the command to operate in the first operating mode, reposition the workspace of the robotic arm while performing at least one null-space movement of the plurality of motorized joints such that the first, second, and third axes pass through the remote center. In some embodiments, the instructions, when executed, cause the at least one computing device to at least, in response to receiving the command to operate in the second operating mode, reposition the workspace of the robotic arm while performing at least one null-space movement of the plurality of motorized joints such that the second axis remains aligned with the opening of a patient.

In some embodiments, the instructions, when executed, cause the at least one computing device to at least, in response to receiving a storage command, position the plurality of linkages substantially parallel to one another. In some embodiments, the robotic arm further comprises an instrument driver coupled to the second motorized joint and configured to manipulate the medical instrument, wherein the instructions, when executed, cause the at least one computing device to at least actuate the instrument driver to manipulate the medical instrument. In some embodiments, the instructions, when executed, cause the at least one computing device to at least, in response to receiving the command to operate in the second operating mode identify at least one additional robotic arm coupled to an additional instrument driver; and position the robotic arm and the additional robotic arm such that the instrument driver and additional instrument driver are aligned along the second axis. In some embodiments, the first axis comprises a yaw axis, the second axis comprises an insertion axis, and the third axis comprises a pitch axis, wherein the at least one processor is configured to execute the instructions to cause the system to at least actuate the instrument driver to control movement of the medical instrument about a roll axis. In some embodiments, one of the plurality of additional motorized joints positioned serially adjacent to the second motorized joint comprises an additional prismatic joint configured to move along an additional linear axis parallel to the second axis, and wherein the at least one processor is configured to execute the instructions to cause the system to at least move the additional prismatic joint along the additional linear axis.

Another aspect relates to a method, comprising receiving a command to operate in one of a first operating mode and a second operating mode of controlling movement of a medical instrument via a robotic arm comprising a plurality of linkages serially coupling a plurality of motorized joints, the plurality of motorized joints including a first motorized joint comprising a revolute joint, the first motorized joint configured to rotate about a first axis, a second motorized joint comprising a prismatic joint configured to linearly translate the medical instrument along a second axis, and a plurality of additional motorized joints positioned serially between the first and second motorized joints, the plurality of additional motorized joints configured to actuate the movement of the medical instrument about a third axis; in response to receiving the command to operate in the first operating mode, (i) fixing a location of a remote center based on an opening of a patient, and (iii) constraining the motion of the plurality of motorized joints when actuated in the first operating mode such that the such that the second axis passes through the remote center; and in response to receiving the command to operate in the second operating mode, aligning a virtual rail coaxial with the second axis with the opening of the patient.

The method can be performed programmatically by at least one computing device. In some embodiments, each of the plurality of motorized joints comprises a motor having a rotor, and wherein the method further comprises controlling positioning of the robotic arm in the first and second operating modes based at least partly on a position of the rotor of the motor of each of the plurality of motorized joints. In some embodiments, in response to receiving a command to operate in the second operating mode, the method further comprises (i) actuating at least some of the plurality of motorized joints to align the second axis with the opening of the patient, (ii) identifying a positioning of a virtual rail based on positioning of the second axis when aligned with the opening of the patient, and (iii) controlling actuation of the medical instrument along the virtual rail. Some embodiments further comprise, in response to receiving the command to operate in the first operating mode identifying that a cannula is docked to a cannula holder coupled to a linkage of the plurality of linkages with the second motorized joint configured to linearly move along the linkage; determining the location of the remote center based at least partly on a location of the cannula holder; and causing the robotic arm to perform at least one null-space movement to align the first axis to pass through the remote center, wherein during the null-space movement one or more of the plurality of motorized joints is actuated and the location of the cannula holder remains fixed.

Some embodiments further comprise constraining the motion of the plurality of motorized joints in the first operating mode such that the first, second, and third axes pass through the remote center. In some embodiments, the plurality of additional motorized joints comprise third, fourth, and fifth joints, and, to constrain the motion of the plurality of motorized joints when actuated in the first operating mode, the method further comprises identifying a virtual orientation of a virtual linkage between the remote center and the third joint; and maintaining positioning of a linkage of the plurality of linkages coupling the fourth and fifth joints parallel with the virtual orientation of the virtual linkage. Some embodiments further comprise receiving a command to adjust a distance between the position of the first motorized joint and the location of the remote center; and performing at least one null-space movement to adjust the distance by actuating at least one of the plurality of motorized joints while maintaining alignment of the first, second, and third axes through the remote center.

In some embodiments, a mechanical reach of the robotic arm extends throughout a workspace, the method further comprising actuating a setup joint coupled to the robotic arm to reposition the workspace of the robotic arm. Some embodiments further comprise, in response to receiving the command to operate in the first operating mode, repositioning the workspace of the robotic arm while performing at least one null-space movement of the plurality of motorized joints such that the first, second, and third axes pass through the remote center. Some embodiments further comprise, in response to receiving the command to operate in the second operating mode, repositioning the workspace of the robotic arm while performing at least one null-space movement of the plurality of motorized joints such that the second axis remains aligned with the opening of a patient. Some embodiments further comprise receiving a storage command for positioning of the robotic arm while not in use; and responsive to the storage command, positioning the plurality of linkages substantially parallel to one another. In some embodiments, the robotic arm further comprises an instrument driver coupled to the distal motorized joint and configured to manipulate the medical instrument, and the method further comprises actuating the instrument driver to manipulate the medical instrument.

Some embodiments further comprise, in response to receiving the command to operate in the second operating mode identifying at least one additional robotic arm coupled to an additional instrument driver configured to manipulate an additional medical instrument; and positioning the robotic arm and the additional robotic arm such that the instrument driver and additional instrument driver are aligned along the second axis. In some embodiments, the first axis comprises a yaw axis, the second axis comprises an insertion axis, and the third axis comprises a pitch axis, the method further comprising actuating the instrument driver to control movement of the medical instrument about a roll axis. In some embodiments, one of the plurality of additional motorized joints positioned serially adjacent to the distal motorized joint comprises an additional prismatic joint configured to move along an additional linear axis parallel to the second axis, the method further comprising moving the additional prismatic joint along the additional linear axis.

Another aspect relates to a robotic system configured to perform medical procedures, the system comprising a robotic arm configured to control movement of a medical instrument with respect to at least first, second, and third axes, the robotic arm comprising a plurality of linkages serially coupling a plurality of motorized joints, the plurality of motorized joints including a first motorized joint comprising a revolute joint, the first motorized joint configured to actuate the movement of the medical instrument about the first axis, a second motorized joint comprising a prismatic joint configured to linearly translate the medical instrument along the second axis, and a plurality of additional motorized joints positioned serially between the first and second motorized joints, the plurality of additional motorized joints configured to actuate the movement of the medical instrument about the third axis; at least one computer-readable memory having stored thereon executable instructions for operating the robotic system; and at least one processor in communication with the at least one computer-readable memory and configured to execute the instructions to cause the system to at least fix a location of a remote center relative to an opening of a patient, and constrain the motion of the plurality of motorized joints when actuated such that the second axis passes through the remote center.

In some embodiments, each of the plurality of motorized joints comprises its own motor. In some embodiments, each of the plurality of motorized joints further comprises a position sensor configured to determine a position of a rotor of the motor. In some embodiments, the at least one processor is configured to execute the instructions to cause the system to at least control positioning of the robotic arm based at least partly on the position of the rotor of the motor of each of the plurality of motorized joints.

In some embodiments, the plurality of additional motorized joints comprise third, fourth, and fifth joints. In some embodiments, each of the third, fourth, and fifth joints comprises an additional revolute joint. In some embodiments, a first linkage of the plurality of linkages couples the first and third joints, a second linkage of the plurality of linkages couples the third and fourth joints, and a first length of the first linkage is longer than a second length of the second linkage. In some embodiments, the at least one processor is configured to execute the instructions to cause the system to at least rotate the third and fourth joints such that the fourth joint passes from a first position on a first side of the first linkage past the first joint to a position on a second side of the first linkage. In some embodiments, a third linkage of the plurality of linkages couples the fourth and fifth joints, the first, second, and third linkages being configured to be positioned in a substantially parallel fashion with the second linkage positioned between the first and third linkages. In some embodiments, a fourth linkage couples the second and fifth joints, the fourth linkage configured to be substantially parallel with and adjacent to the third linkage. In some embodiments, each of the third and fourth joints comprise first and second additional revolute joints and the fifth joint comprises an additional prismatic joint. In some embodiments, the additional prismatic joint is configured to move along an additional axis parallel to the second axis, wherein the at least one processor is configured to execute the instructions to cause the system to at least move the additional prismatic joint along the additional axis.

Some embodiments further comprise an instrument driver coupled to the second motorized joint and configured to manipulate the medical instrument, wherein the at least one processor is configured to execute the instructions to cause the system to at least actuate the instrument driver to manipulate the medical instrument. In some embodiments, the instrument driver is aligned along the second axis. In some embodiments, the first axis comprises a yaw axis, the second axis comprises an insertion axis, and the third axis comprises a pitch axis, wherein the at least one processor is configured to execute the instructions to cause the system to at least actuate the instrument driver to control movement of the medical instrument about a roll axis.

Some embodiments further comprise a cannula holder coupled to a linkage of the plurality of linkages with the second motorized joint configured to linearly move along the linkage, wherein the at least one processor is configured to execute the instructions to cause the system to at least identify that a cannula is docked to the cannula holder; determine the location of the remote center based at least partly on a location of the cannula holder; and cause the robotic arm and at least one setup joint coupled to the robotic arm to perform at least one null-space movement to align the first axis to pass through the remote center, wherein during the null-space movement at least one joint of the plurality of motorized joints and the at least one setup joint is actuated and the location of the cannula holder remains fixed. In some embodiments, after performing the at least one null-space movement, the at least one processor is configured to execute the instructions to cause the system to at least constrain the motion of the plurality of motorized joints such that the first, second, and third axes pass through the remote center. Some embodiments further comprise a motorized setup joints coupled to the robotic arm, wherein the at least one processor is configured to execute the instructions to cause the system to at actuate the motorized setup joint to perform the null-space movement.

In some embodiments, each of the third, fourth, and fifth joints comprises an additional revolute joint, and wherein, to constrain the motion of the plurality of motorized joints after performing the at least one null-space movement, the at least one processor is configured to execute the instructions to cause the system to at least identify a virtual orientation of a virtual linkage between the remote center and the third joint; and maintain positioning of a linkage of the plurality of linkages coupling the fourth and fifth joints parallel with the virtual orientation of the virtual linkage. In some embodiments, the at least one processor is configured to execute the instructions to cause the system to at least change a distance between the remote center and the third joint. In some embodiments, the at least one processor is configured to execute the instructions to cause the system to at least fix a distance between the remote center and the third joint to be equal to a length of the linkage coupling the fourth and fifth joints. In some embodiments, the at least one processor is configured to execute the instructions to cause the system to at least receive a command to adjust a distance between the position of the first motorized joint and the location of the remote center; and perform at least one null-space movement to adjust the distance by actuating at least one joint from the plurality of additional motorized joints while maintaining alignment of the first, second, and third axes through the remote center.

Some embodiments further comprise a setup joint coupled to the robotic arm, wherein a mechanical reach of the robotic arm extends throughout a workspace, and wherein the at least one processor is configured to execute the instructions to cause the system to at least actuate the setup joint to reposition the workspace of the robotic arm. In some embodiments, the at least one processor is configured to execute the instructions to cause the system to at least reposition the workspace of the robotic arm while performing null-space movement of the plurality of motorized joints such that the first, second, and third axes pass through the remote center. In some embodiments, the at least one processor is configured to execute the instructions to cause the system to at least reposition the workspace of the robotic arm while performing null-space movement of the plurality of motorized joints such that the second axis remains aligned with the opening of a patient.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 20B depicts the table-based robotic system of FIG. 19B including some of the robotic arms configured as shown in FIG. 20A for operating in the second mode for an endoscopic procedure.

DETAILED DESCRIPTION

1. Overview.

Aspects of the present disclosure may be integrated into a robotically enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
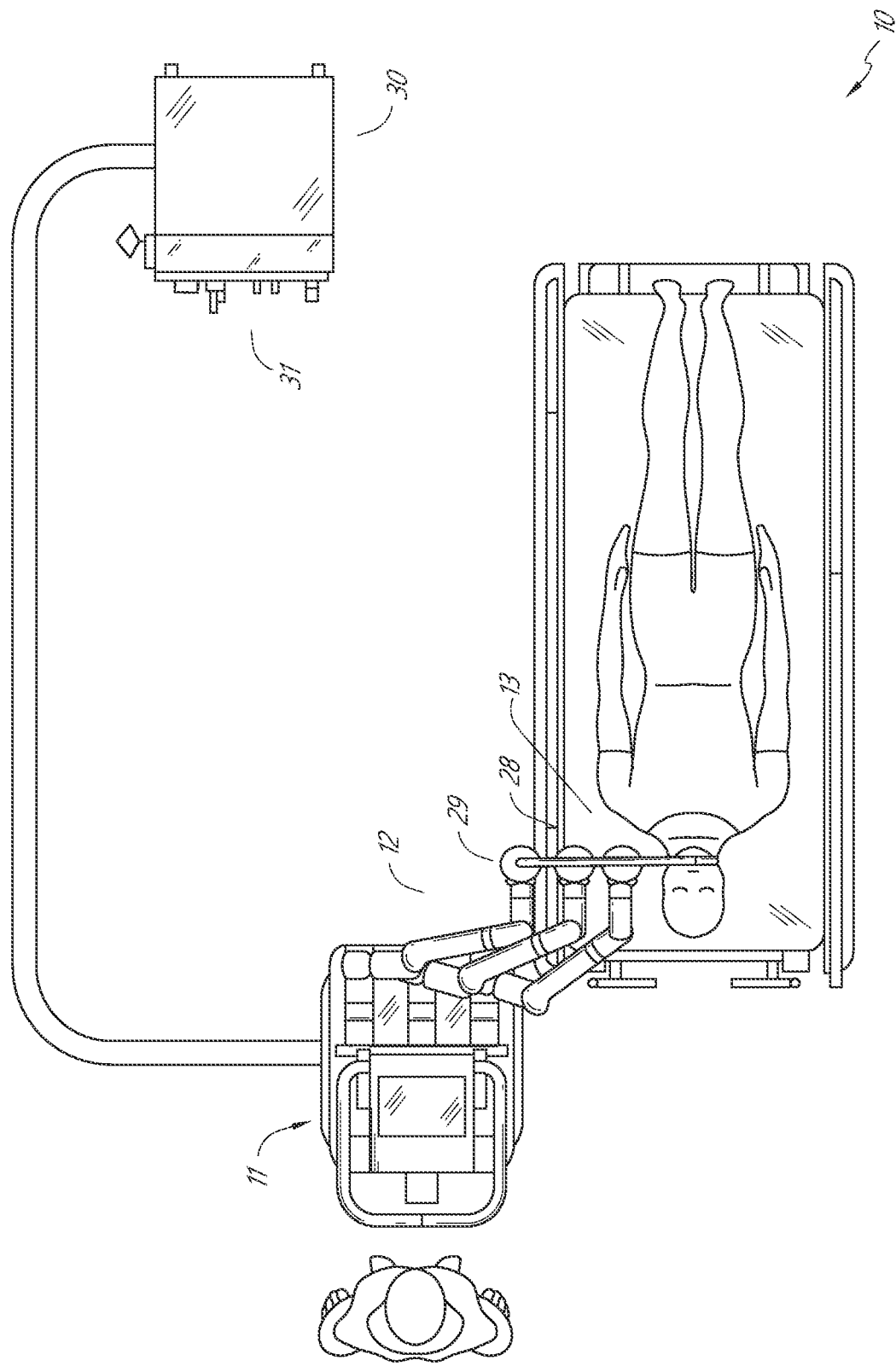
FIG. 1 illustrates an embodiment of a cart-based robotic system arranged for diagnostic and/or therapeutic bronchoscopy procedure(s).
Figure 2:
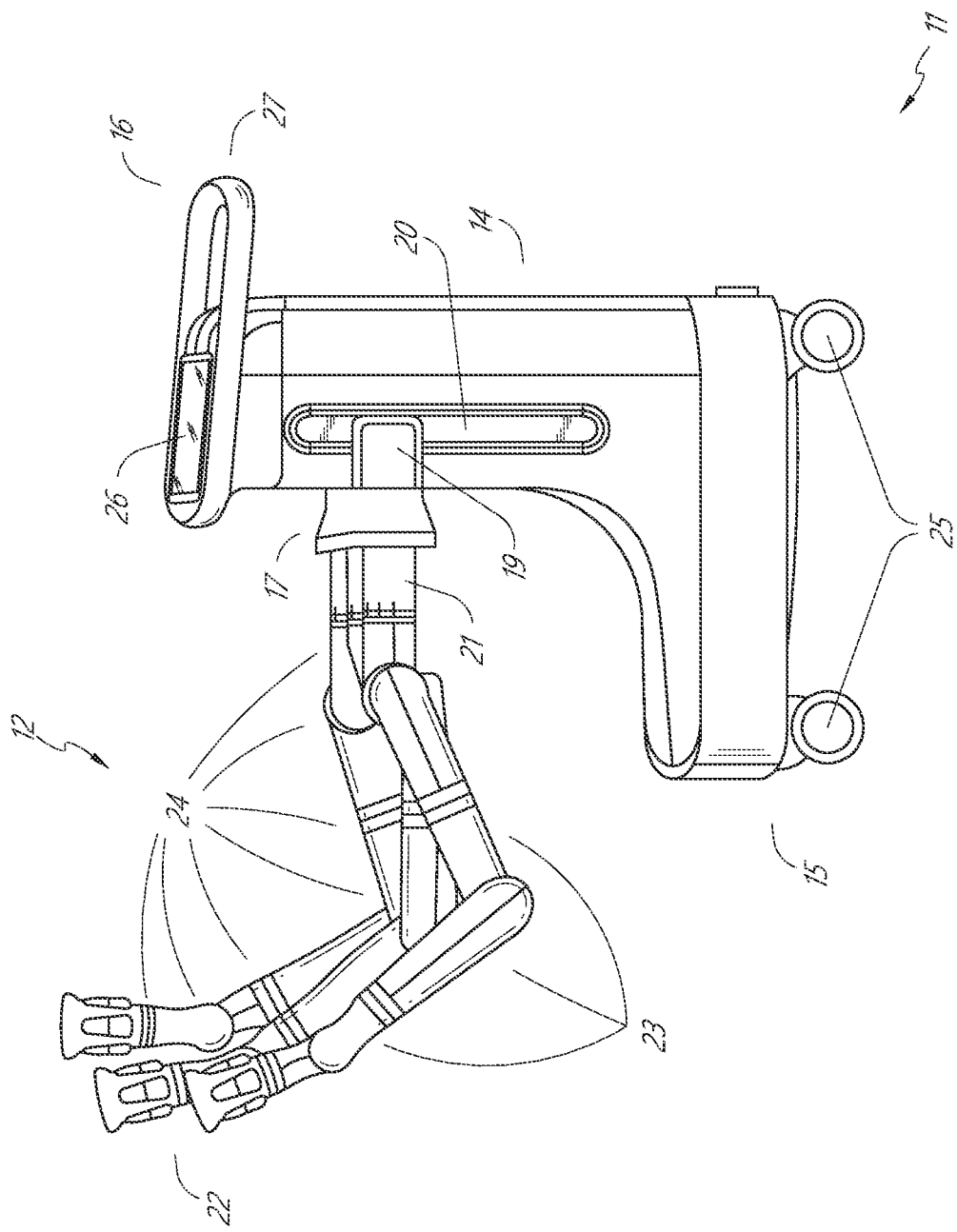
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI)

procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position the physician may view the console 16, robotic arms 12, and patient while operating the console 16 from behind the cart 11. As shown, the console 16 also includes a handle 27 to assist with maneuvering and stabilizing cart 11.

Figure 3:
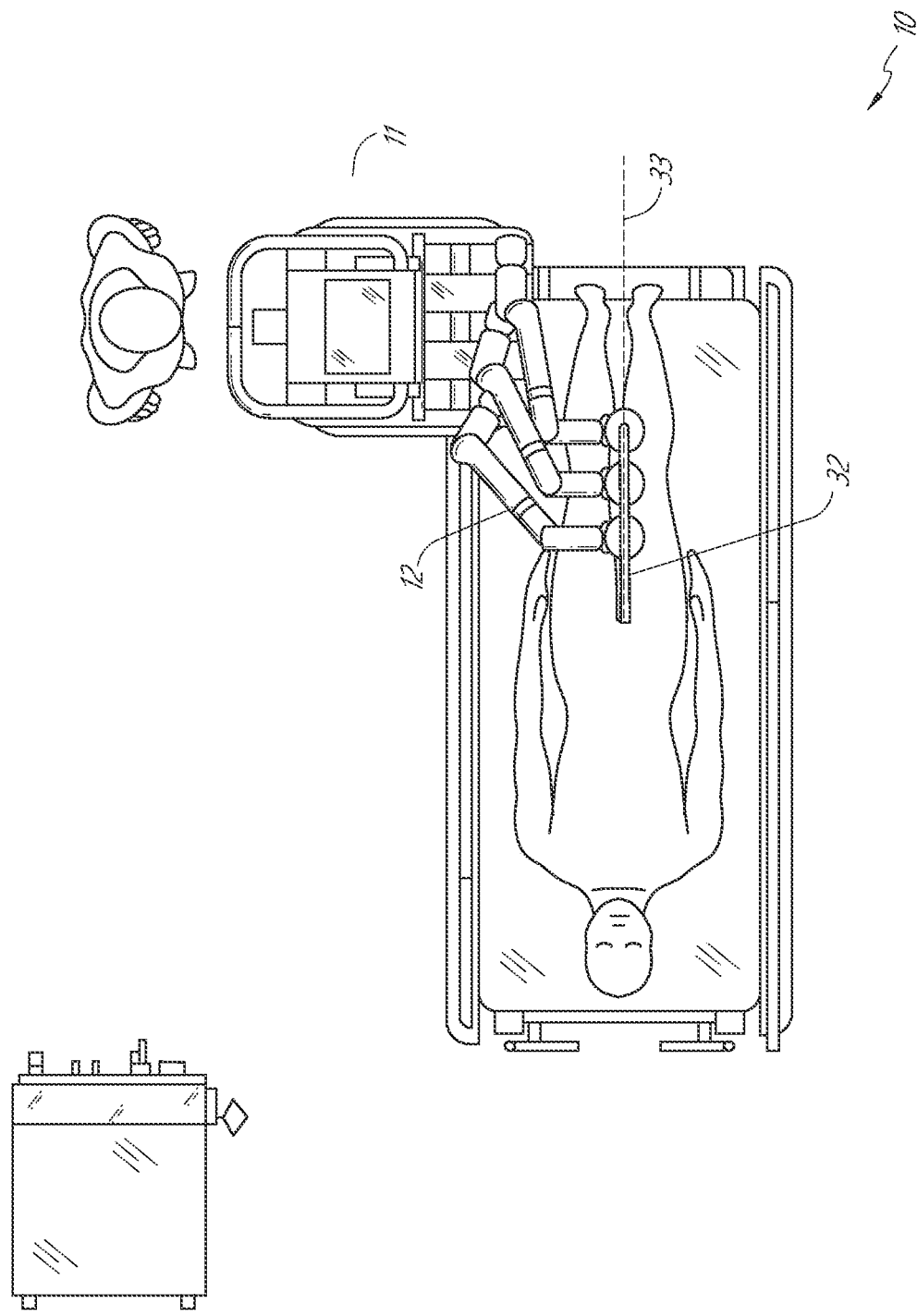
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
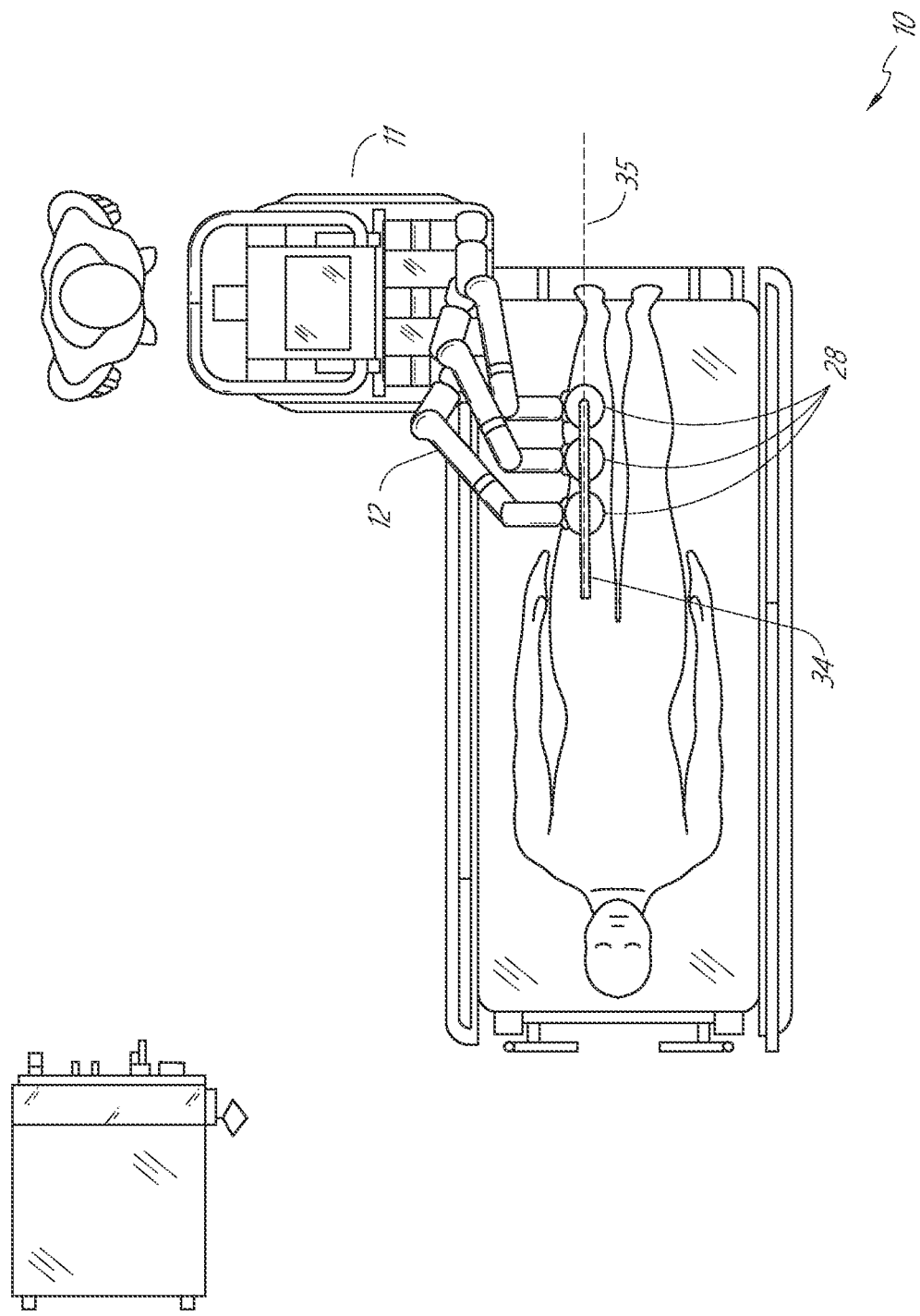
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
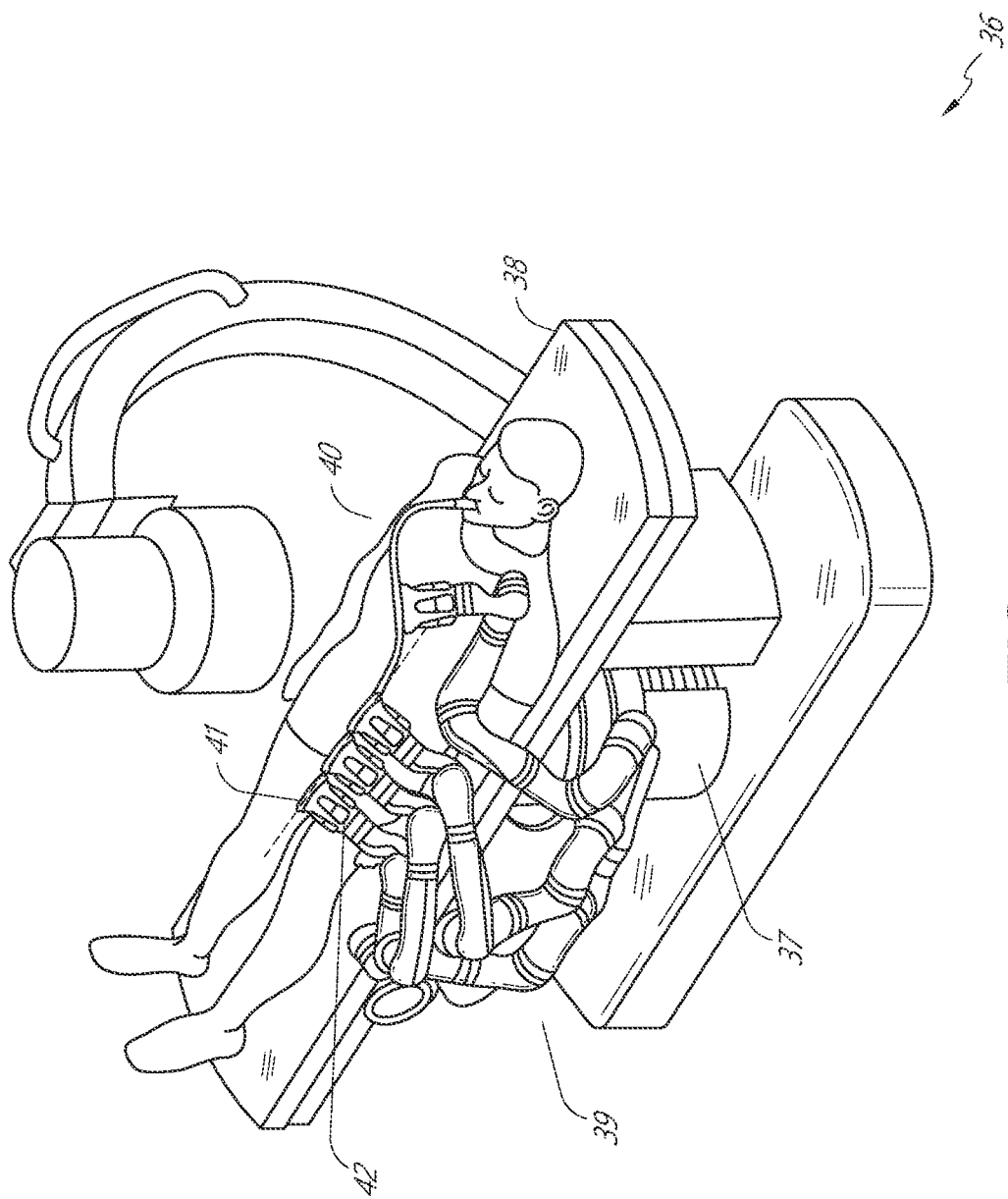
FIG. 5 illustrates an embodiment of a table-based robotic system arranged for a bronchoscopy procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
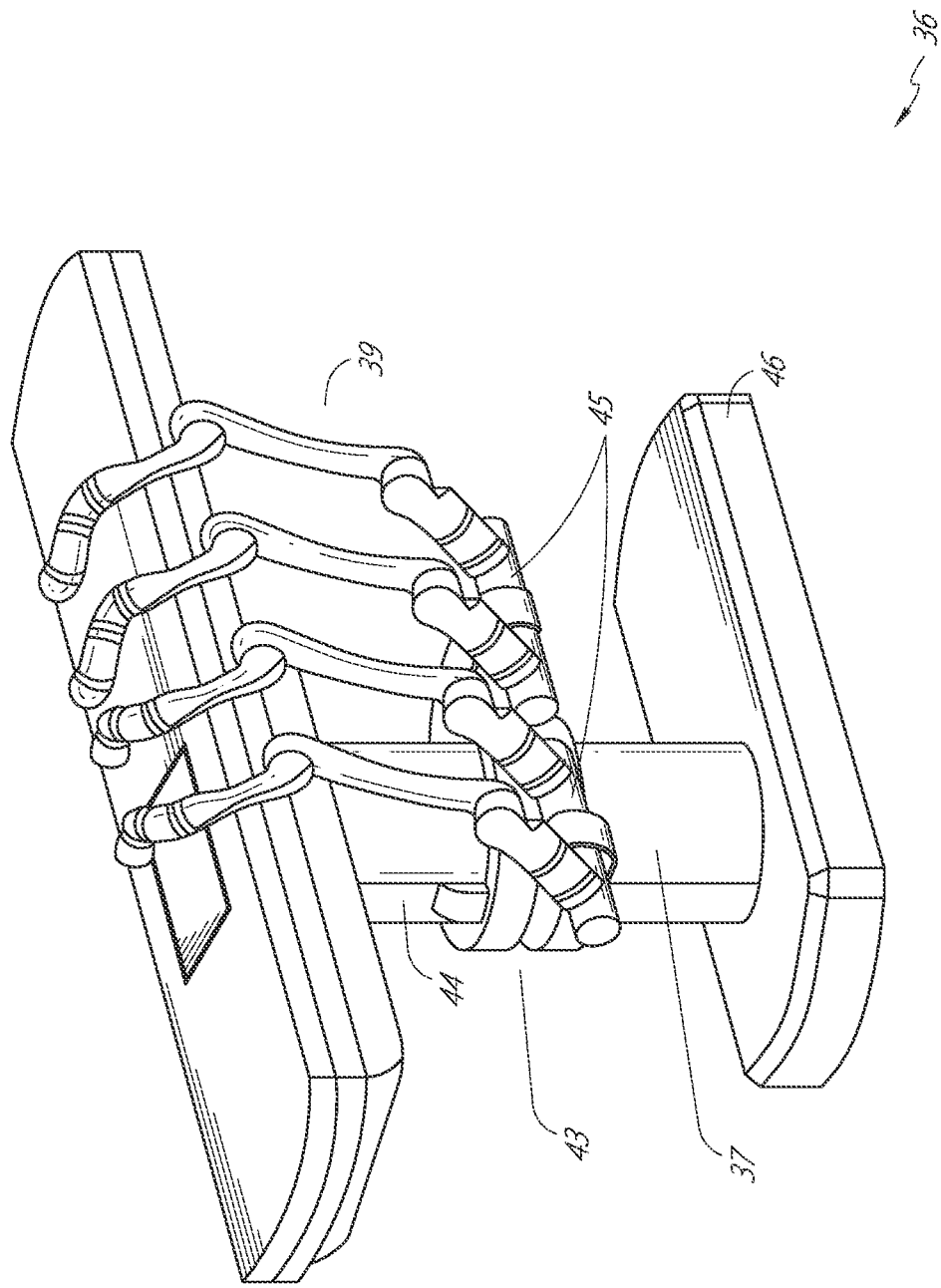
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
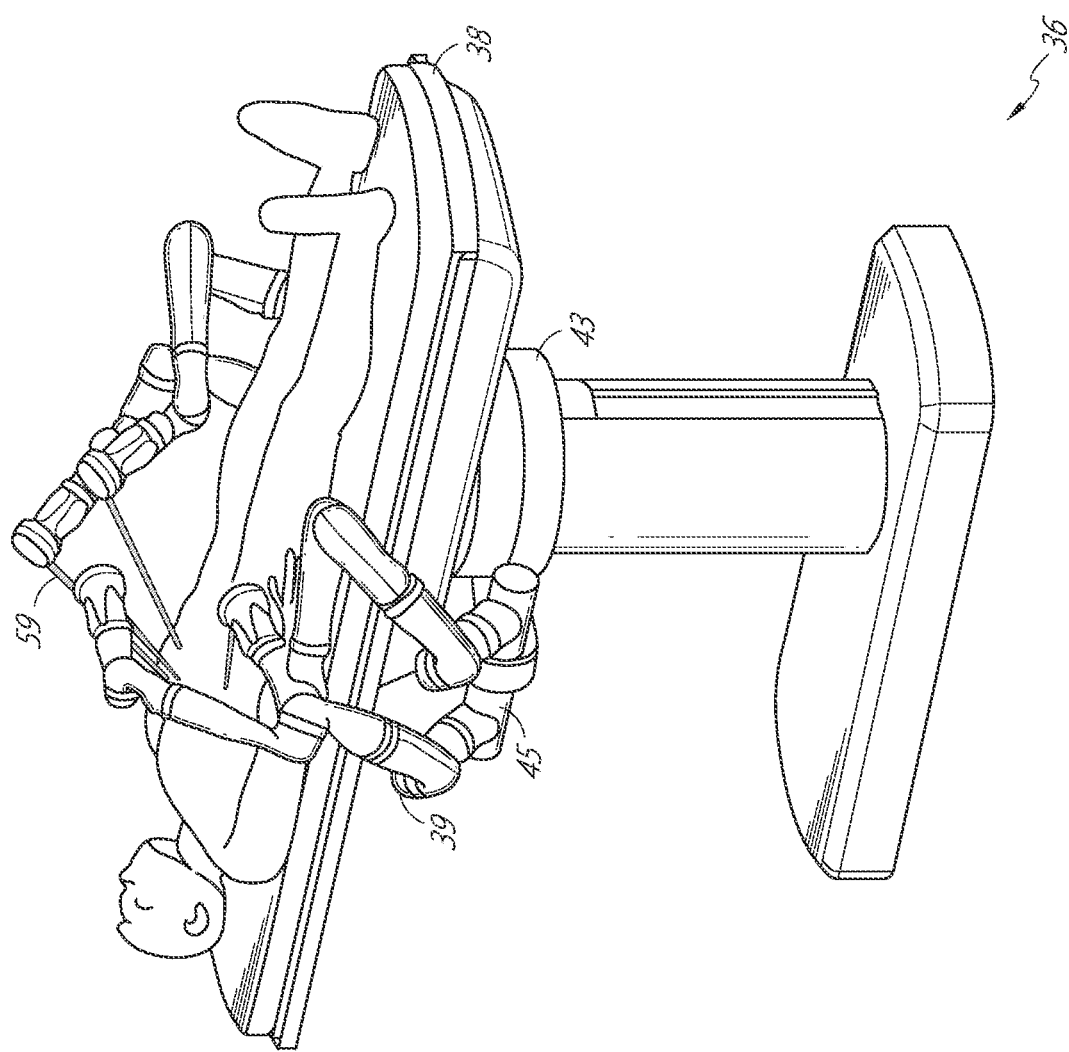
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
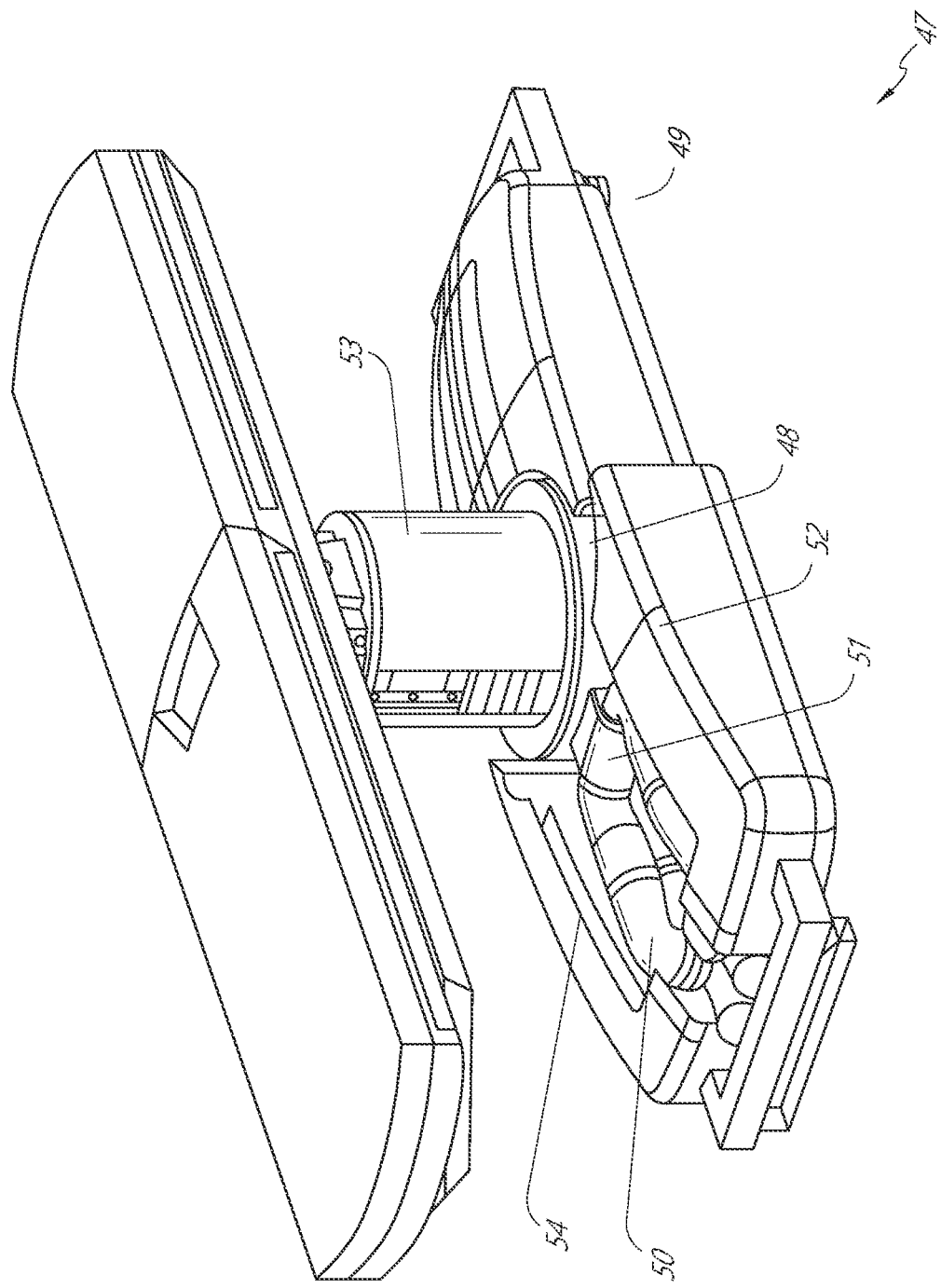
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
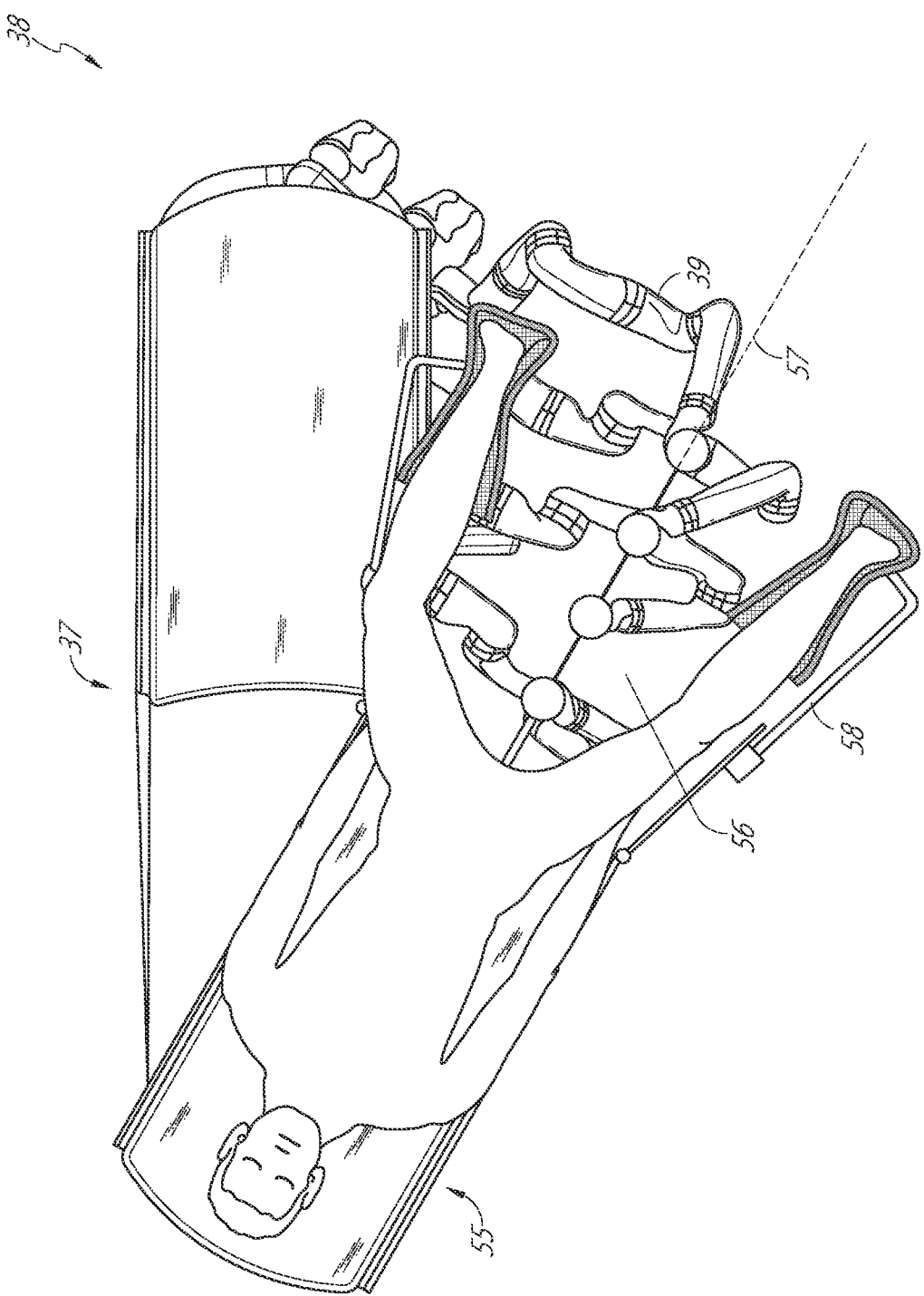
FIG. 8 illustrates an embodiment of a table-based robotic system configured for a ureteroscopy procedure.

FIG. 8 illustrates an embodiment of a robotically enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
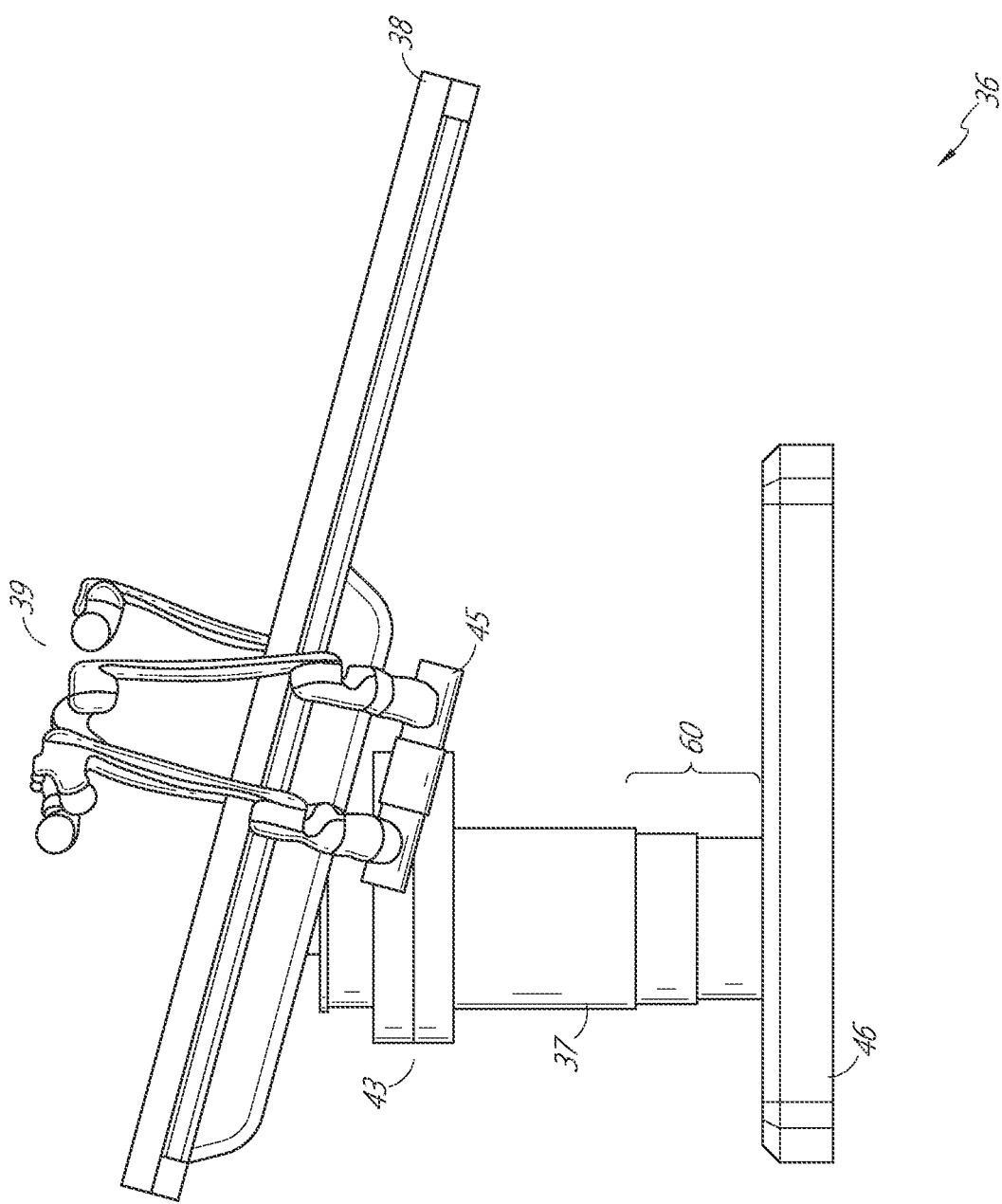
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
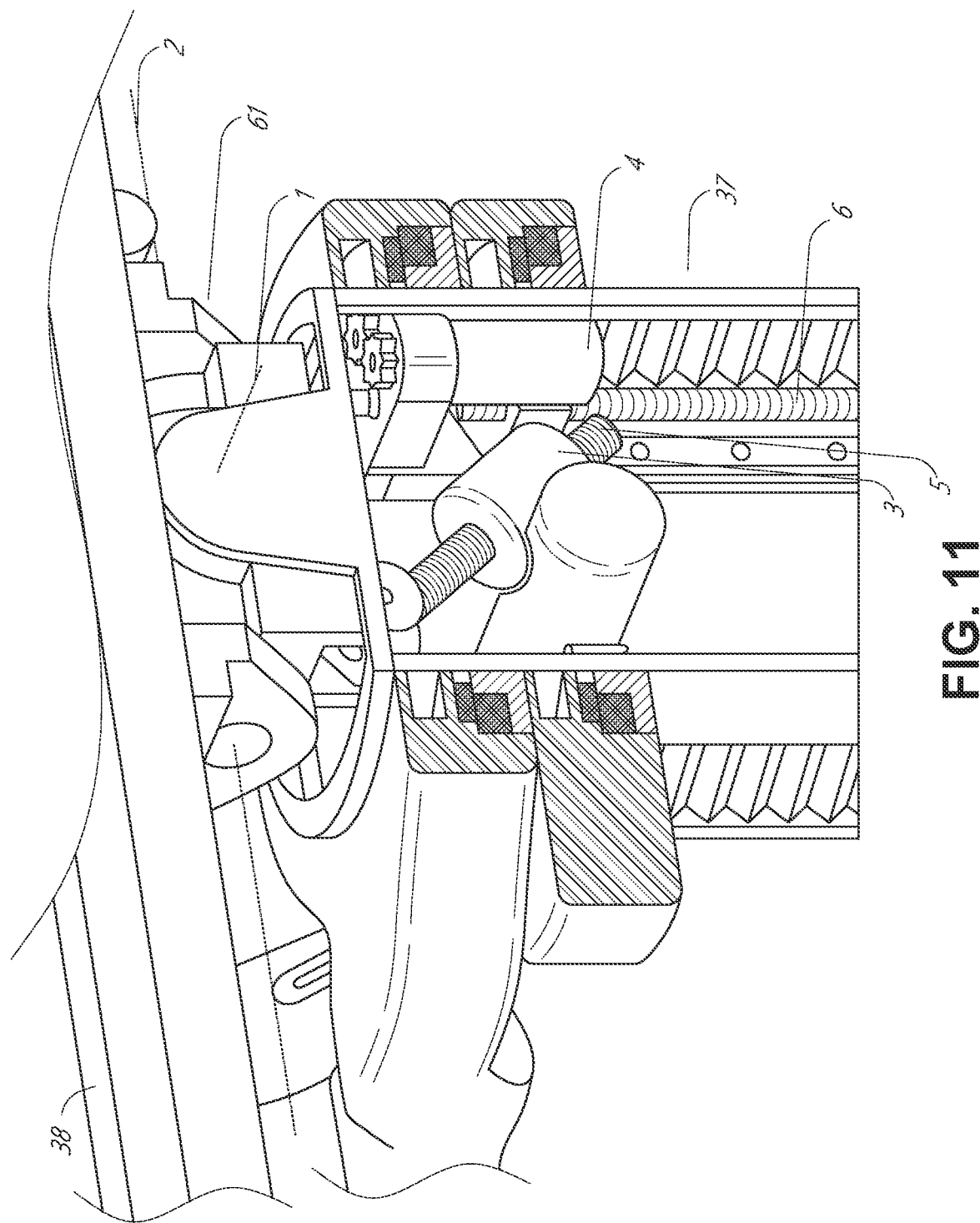
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 2, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic pro s tatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
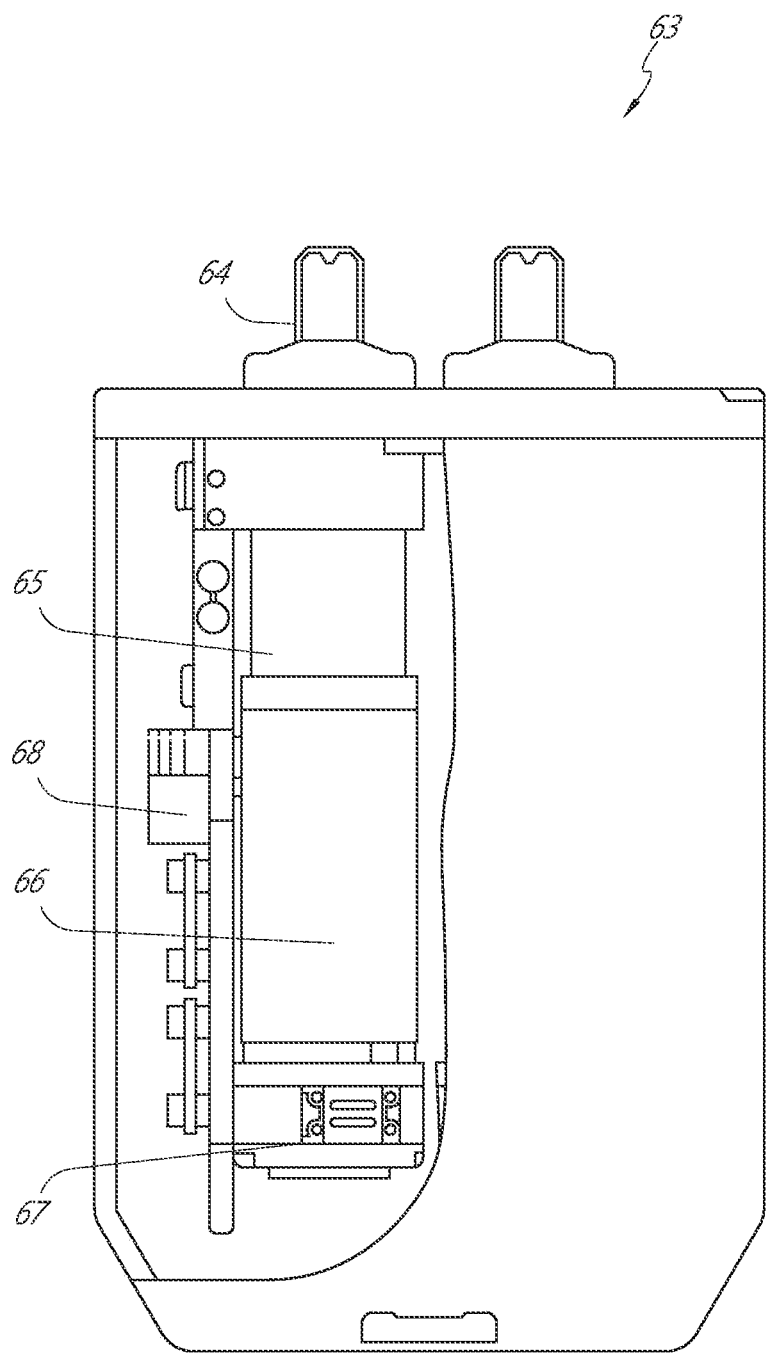
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
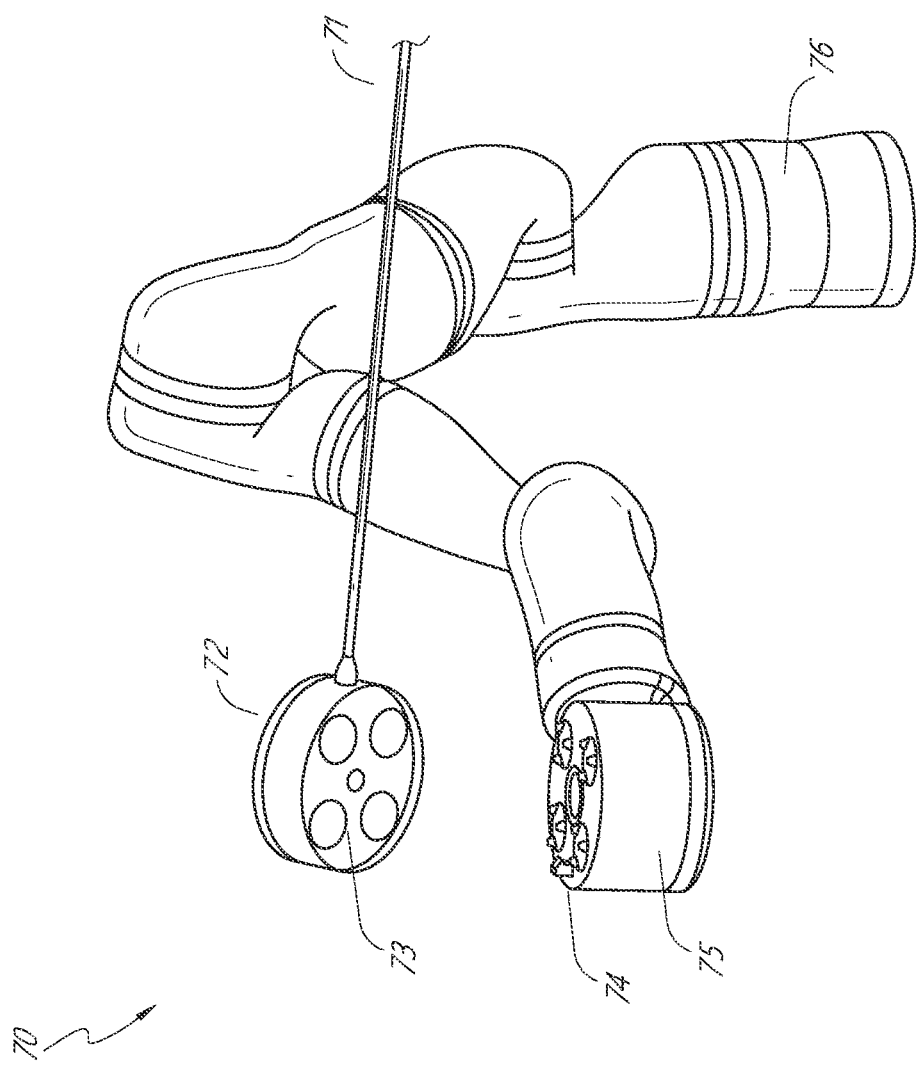
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shalt 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
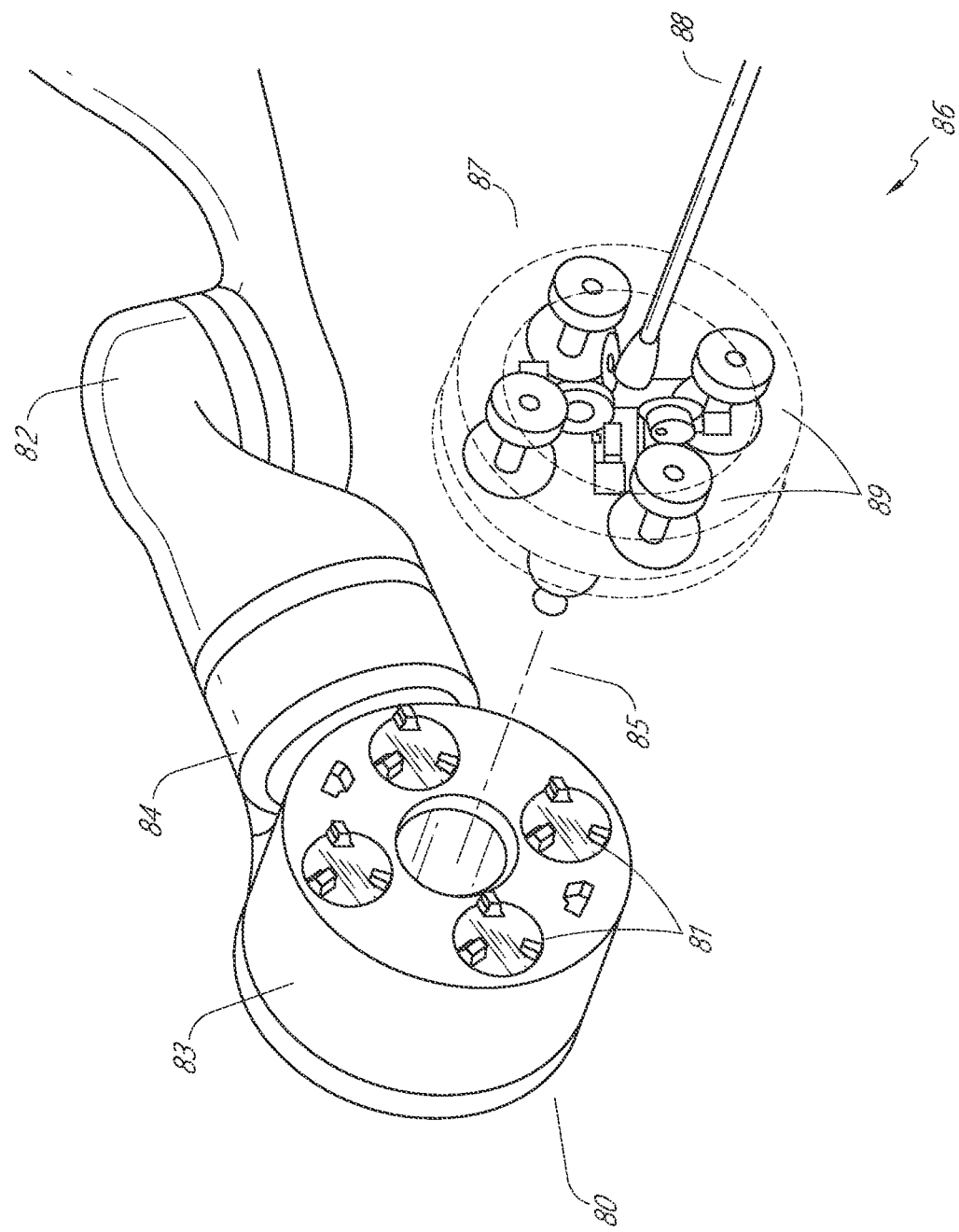
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
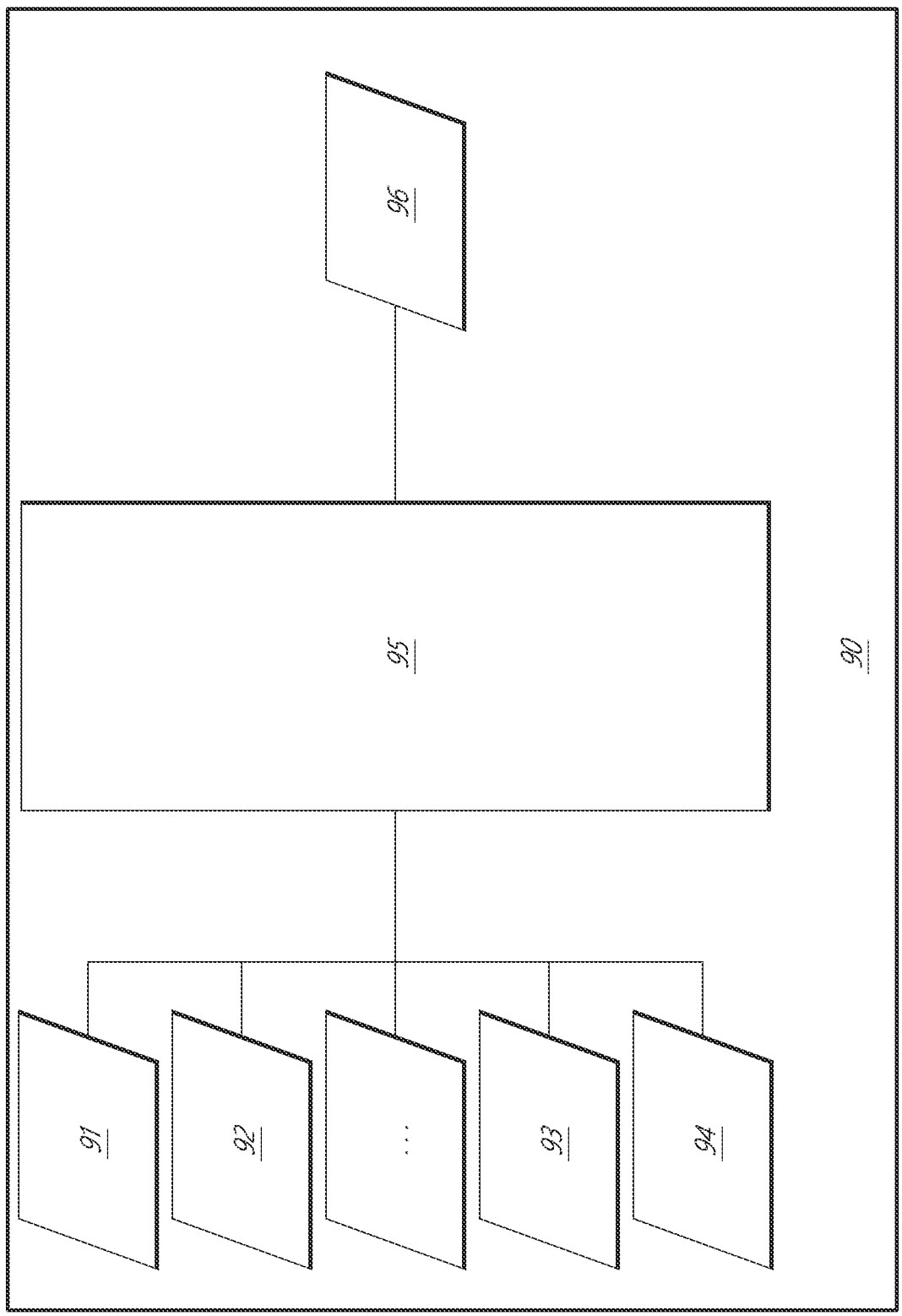
FIG. 15 depicts a block diagram illustrating a localization system that estimates a location of one or more elements of the robotic systems of FIGS. 1-10, such as the location of the instrument of FIGS. 13-14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans generate two-dimensional images, each representing a "slice" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Flexible Medical Robotics Systems and Techniques

Embodiments of the disclosure relate to versatile robotic systems and operational techniques associated with a single robotic system to be capable of performing multiple types of medical procedures. As described above, due to the varying requirements of different medical procedures, robotic systems may be designed and built specifically for performing a single medical procedure, and as a result may be unable to satisfy the requirements for performing other medical procedures.

For example, one existing system is purpose-built for laparoscopic surgery. The existing system is designed with robotic arm kinematics including a mechanically constrained remote center provided so that the robotic arm inserts, pitches, and yaws a medical instrument with respect to the remote center. The mechanically constrained remote center is effected by multiple joints that are connected to one another by bands, such that all joints are controlled by a single motor. While the inertia of the robotic arm is generally low and the robotic arm is able to maintain the remote center even under loss of power, a potential drawback of this design is that it is not used for performing non-laparoscopic procedures. For example, due to the mechanical remote center it may be difficult to utilize the robotic arm for endoscopic procedures because the mechanically constrained remote center makes it hard to align the robotic arm along a virtual rail. In addition, the bands used to create the mechanical remote center prevent compact storage of the robotic arm.

Similarly, existing serial link manipulators used for endoscopic procedures do not convert to laparoscopy well because it is hard to meet the stiffness and speed requirements for laparoscopy while maintaining a low inertia arm.

The above described problems, among others, are addressed by the multipurpose robotics systems and associated operating techniques described herein that are able to accommodate a wide range of procedures. For example, a robotic arm according to the present disclosure includes a versatile kinematic chain and is controlled by computer-implemented instructions that enable the robotic arm to operate in a variety of modes, with different modes usable for different types of medical procedures. The kinematic chain includes a number of motorized joints coupled by linkages in a serial fashion, with a revolute motorized joint at the proximal end of the robotic arm (e.g., closest to setup joints or a base of the robotic system), a prismatic motorized joint at the distal end of the robotic arm (e.g., closest to the medical instrument), and a number of additional motorized joints positioned serially between the first and second motorized joints. The additional motorized joints can be either revolute or prismatic as explained in more detail below. The robotic arm can be operated in a first mode with respect to a remote center to perform laparoscopic procedures and can be operated in a second mode with respect to a virtual rail to perform endoscopic procedures. While the present disclosure provides examples of first and second operating modes for laparoscopic and endoscopic procedures, respectively, the disclosed robotic systems can also be used to perform other types of medical procedures.

Figure 16:
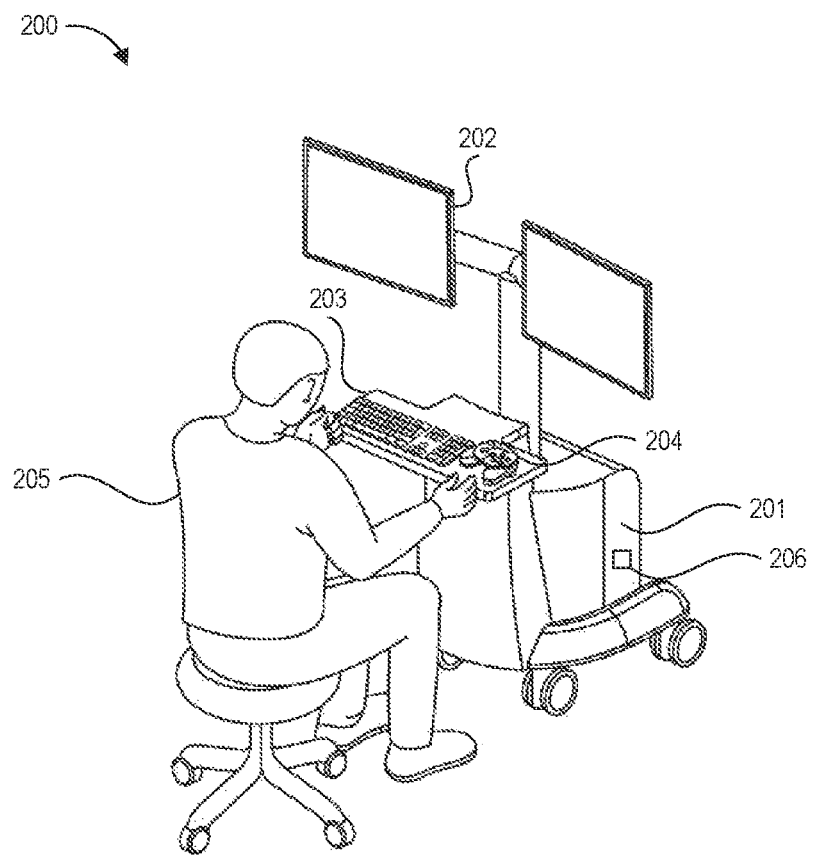
FIG. 16 illustrates an example command console for a medical robotic system as depicted in FIGS. 1-5 and 8-10, according to one embodiment.

The disclosed robotic systems can be controlled by a physician or other operator in order to perform medical procedures according to the disclosed modes. FIG. 16 illustrates an example command console 200 for a medical robotics system as described herein, for example in a medical robotic system as depicted in FIGS. 1-5 and 8-10. The command console 200 that can be used, for example, as the command console 105 in the example operating environment 100. The command console 200 includes a console base 201, display modules 202, e.g., monitors, and control modules, e.g., a keyboard 203 and joystick 204. In some embodiments, one or more of the command console 200 functionality may be integrated into a base of a medical robotic system as depicted in FIGS. 1-5 and 8-10 or another system communicatively coupled to the medical robotic system. A user 205, e.g., a physician, remotely controls the medical robotic system from an ergonomic position using the command console 200.

The console base 201 may include controller 206 including a one or more processors and memories, and optionally one or more data buses and associated data communication ports. Controller 206 is responsible for interpreting and processing signals such as robotic position data, camera imagery, and tracking sensor data, e.g., from a medical instrument such as endoscope 13, ureteroscope 32, medical instrument 34, laparoscope 59, gastroscope, bronchoscope, or another procedure-specific medical instrument. The memory of the controller 206 can store instructions for operation of the medical instruments and robotic systems described herein. In some embodiments, both the console base 201 and the base of the medical robotic system can perform signal processing for load-balancing, and thus the controller 206 may be split between different system components. The controller 206 may also process commands and instructions provided by the user 205 through the control modules 203 and 204. In addition to the keyboard 203 and joystick 204 shown in FIG. 16, the control modules may include other devices, for example, computer mice, trackpads, trackballs, control pads, controls such as handheld remote controllers, and sensors (e.g., motion sensors or cameras) that capture hand gestures and finger gestures. For example, for some laparoscopic robotic systems the control modules include a pair of seven degree-of-freedom ("7 DOF") haptic masters. A haptic master is a force controlled haptic interface that translates input (e.g., force applied by a human user) to output (e.g., displacement of the end effector of the robotic system) and also provides tactile feedback back to the user. A 7 DOF haptic master can provide three degrees of motion in the X, Y, Z directions and four degrees of motion of the pitch, yaw, roll and articulation. A control can include a set of user inputs (e.g., buttons, joysticks, directional pads, etc.) mapped to an operation of the instrument (e.g., articulation, driving, water irrigation, etc.).

The user 205 can control a medical instrument via a robotic arm as described herein using the command console 200 in a velocity mode or position control mode. In velocity mode, the user 205 directly controls pitch and yaw motion of a distal end of the medical instrument based on direct manual control using the control modules. For example, movement on the joystick 204 may be mapped to yaw and pitch movement in the distal end of the medical instrument. The joystick 204 can provide haptic feedback to the user 205. For example, the joystick 204 may vibrate to indicate that the medical instrument cannot further translate or rotate in a certain direction. The command console 200 can also provide visual feedback (e.g., pop-up messages) and/or audio feedback (e.g., beeping) to indicate that the medical instrument has reached maximum translation or rotation.

In position control mode, the command console 200 uses a 3D map of a patient luminal network and input from navigational sensors as described herein to control a medical instrument. The command console 200 provides control signals to robotic arms of the medical robotic system to manipulate the medical instrument to a target location. Due to the reliance on the 3D map, position control mode may require accurate mapping of the anatomy of the patient.

In some embodiments, users 205 can manually manipulate robotic arms of the medical robotic system without using the command console 200. During setup in a surgical operating room, the users 205 may move the robotic arms, medical instruments, and other surgical equipment to access a patient. The medical robotic system may rely on force feedback and inertia control from the users 205 to determine appropriate configuration of the robotic arms and equipment.

The displays 202 may include electronic monitors (e.g., LCD displays, LED displays, touch-sensitive displays), virtual reality viewing devices, e.g., goggles or glasses, and/or other display devices. For example, for some procedures (e.g., laparoscopy) the display can include a compact stereo viewer having a pair of apertures through which a user can view a stereoscopic image without the aid of glasses or goggles. This can be used, for example, to display a stereoscopic laparoscopic image. In some embodiments, the display modules 202 are integrated with the control modules, for example, as a tablet device with a touchscreen. In some embodiments, one of the displays 202 can display a 3D model of the patient's luminal network and virtual navigation information (e.g., a virtual representation of the end of the endoscope within the model based on EM sensor position) while the other of the displays 202 can display image information received from the camera or another sensing device at the end of the medical instrument. In some implementations, the user 205 can both view data and input commands to the medical robotic system using the integrated displays 202 and control modules. The displays 202 can display 2D renderings of 3D images and/or 3D images using a stereoscopic device, e.g., a visor or goggles. The 3D images provide an "endo view" (i.e., endoscopic view), which is a computer 3D model illustrating the anatomy of a patient. The "endo view" provides a virtual environment of the patient's interior and an expected location of a medical instrument inside the patient. A user 205 compares the "endo view" model to actual images captured by a camera to help mentally orient and confirm that the medical instrument is in the correct—or approximately correct—location within the patient. The "endo view" provides information about anatomical structures, e.g., the shape of airways, circulatory vessels, or an intestine or colon of the patient, around the distal end of the medical instrument. The display modules 202 can simultaneously display the 3D model and CT scans of the anatomy the around distal end of the medical instrument. Further, the display modules 202 may overlay the already determined navigation paths of the medical instrument on the 3D model and CT scans.

In some embodiments, a model of the medical instrument is displayed with the 3D models to help indicate a status of a surgical procedure. For example, the CT scans identify a lesion in the anatomy where a biopsy may be necessary. During operation, the display modules 202 may show a reference image captured by the medical instrument corresponding to the current location of the medical instrument. The display modules 202 may automatically display different views of the model of the medical instrument depending on user settings and a particular surgical procedure. For example, the display modules 202 show an overhead fluoroscopic view of the medical instrument during a navigation step as the medical instrument approaches an operative region of a patient. Such user-guided movement of the medical instrument can be constrained according to various pre-defined operating modes for a robotic arm as described herein.

2. Overview of Example Flexible Kinematic Chains

Figure 17:
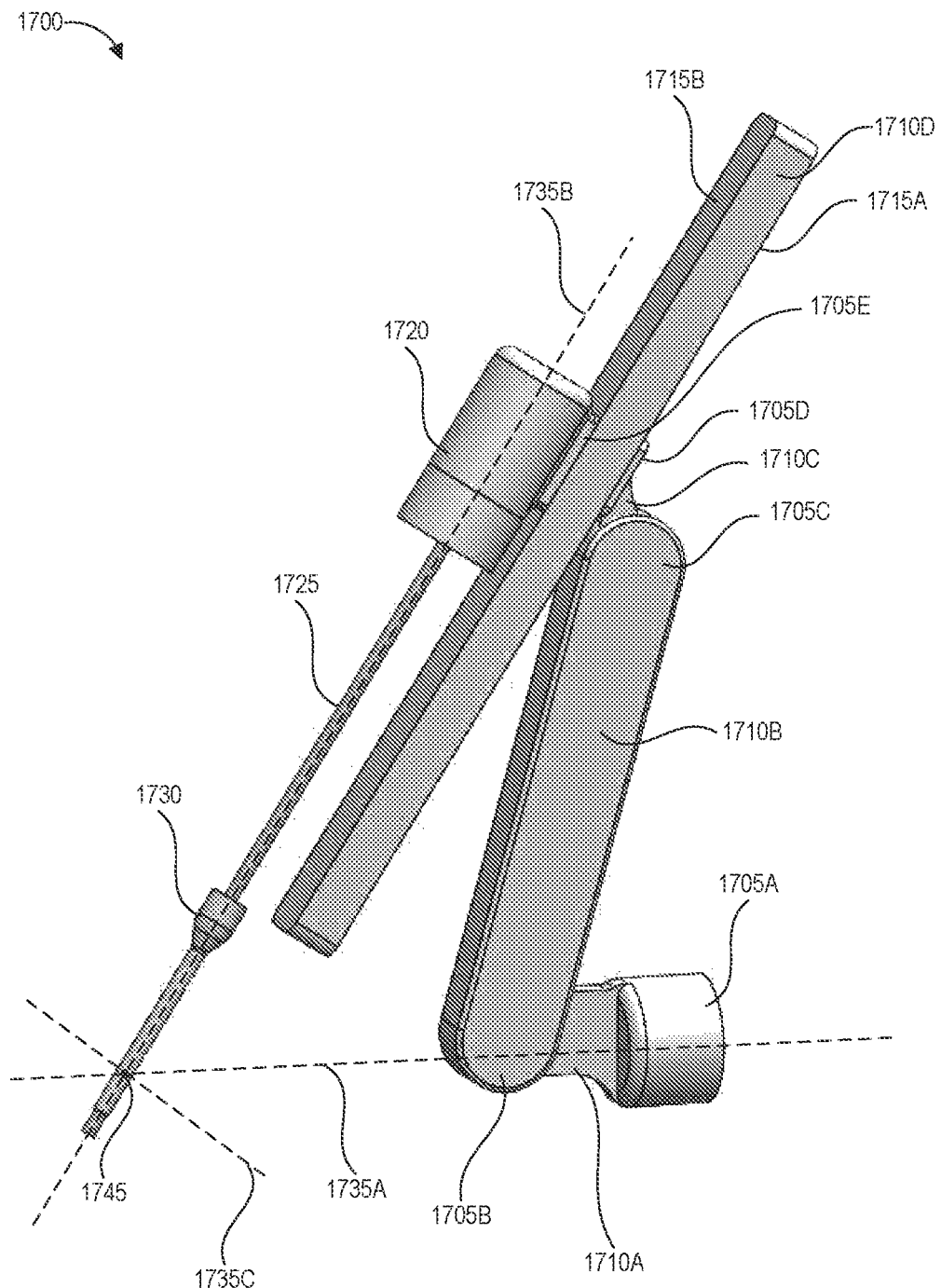
FIG. 17 illustrates an example of a robotic arm usable with the systems and components depicted in FIGS. 1-16.

FIG. 17 illustrates an example of a robotic arm 1700 usable with the systems and components depicted in FIGS. 1-16. The robotic arm 1700 comprises an RRRPP serial chain manipulator, with "R" referring to a revolute joint and "P" referring to a prismatic joint, with such joint labeling beginning at the proximal-most joint 1705A and moving serially along the robotic arm towards the distal-most joint 1705E. The robotic arm 1700 can be configured for use as a low-inertia remote center laparoscopy system or as a virtual rail endoscopic system.

The robotic arm 1700 includes a number of motorized joints 1705A-1705E connected in serial fashion by linkages 1710A-1710D. The first linkage 1710A connects the first motorized joint 1705A and the third motorized joint 1705B, the second linkage 1710B connects the third motorized joint 1705B to the fourth motorized joint 1705C, the third linkage 1710C connects the fourth motorized joint 1705C to the fifth motorized joint 1705D, and the fourth linkage 1710D connects the fifth motorized joint 1705D to the second motorized joint 1705E.

A first motorized joint 1705A at the proximal end of the robotic arm (e.g., closest to setup joints or a base of the robotic system to which the robotic arm 1700 is attached) is a revolute joint that causes rotational motion of medical instrument 1725 around yaw axis 1735A. A second motorized joint 1705E at the distal end of the robotic arm (e.g., closest to the medical instrument 1725) is a prismatic joint that moves linearly along distal face 1715B of the fourth linkage 1710D. Additional motorized joints 1705B, 1705C, 1705D are positioned serially between the first and second motorized joints.

The fifth motorized 1705D joint is a prismatic joint that moves linearly along the proximal face 1715A of the fourth linkage 1710D. The axes of prismatic joints 1705D and 1705E are depicted as being parallel to each other due to the shape of the fourth linkage 1710D, however in other embodiments the axes may not be parallel and the shape of the fourth linkage 1710D may vary accordingly.

The third motorized joint 1705B and fourth motorized joint 1705C are revolute joints that each rotate in a plane positioned orthogonally to the plane of rotation of the first motorized joint 1705A. Actuation of the third motorized joint 1705B and fourth motorized joint 1705C can cause the medical instrument 1725 to rotate about pitch axis 1735C.

Each motorized joint 1705A-1705E can comprise a motor, a position sensor, and a gearbox. In some embodiments, the motor can be an interior permanent magnet motor including a stator, a rotor rotatable within the stator, and a plurality of windings wound through the stator and configured to carry one or more phases of electrical current. The rotor can comprise a magnetically permeable material and at least one permanent magnet embedded within the magnetically permeable material. One example of the position sensor is an optical encoder positioned with a field of view encompassing the rotor such that the optical encoder can capture image data representative of the rotor, the image data usable to determine a position of the rotor. Other examples of suitable position sensors include closed loop position control systems that monitor the current in one or more of the windings of a motor (for example via a Hall sensor or other current sensor), as well as angular joint sensors that generate data usable to determine the angle between adjacent linkages (for example one or more of accelerometers, gyroscopes, magnetometers, conductive fibers, etc.). Output from the position sensors of each of the motorized joints 1705A-1705E can be used by the controller 206 to control actuation of the robotic arm 1700 in the operational modes described herein. The gearbox can include a number of gears to achieve a desired gear ratio for each joint. One example joint can have a 100:1 to 150:1 gear ratio in order to achieve the desired stiffness for operation during endoscopic medical procedures. The gearbox can be a harmonic gearbox using strain wave gearing and thus provides advantages over traditional gear-based gearboxes due to having low or no backlash, high compactness, and light weight.

An instrument driver 1720 can be coupled to the second motorized joint 1705E to secure and/or manipulate medical instrument 1725. The instrument driver 1720 can be the instrument driver described with respect to FIG. 12 in some embodiments. Movement of the second motorized joint 1705E along the distal face 1715B of the fourth linkage 1710D and/or movement of the fifth motorized joint 1705D along the proximal face 1715A of the fourth linkage 1710D can translate into linear motion of the medical instrument 1725 along the insertion axis 1725B. Actuation of the motorized joints 1705A-1705C together with one or more setup joints can also move the medical instrument 1725 along the insertion axis 1725B. The instrument driver 1720 can move the medical instrument 1725 in other degrees of freedom, for example roll of the medical instrument 1725 around the insertion axis 1725B, deflection of the tip of a steerable medical instrument, and the like. The medical instrument 1725 can be any endoscopic or laparoscopic tool, for example a bronchoscope, gastroscope, ureteroscope, colonoscope, steerable catheter, a laparoscope, a tool positioned within the working channel of such a scope (e.g., needles, forceps, cytology brushes, augers, etc.), electrosurgical shears, and other medical instruments used in the disclosed procedures.

In some medical procedures, the instrument 1725 can extend into a cannula 1730 positioned for example in an incision forming an opening into the body of a patient. In other medical procedures the instrument 1725 can extend directly into a natural orifice forming an opening into a luminal network of a patient and thus the cannula 1730 can be omitted. Some embodiments of the robotic arm 1700 can further include a dock (not illustrated, see for example dock 1840 of FIG. 18) that can couple the fourth linkage 1710D to the cannula 1730. The cannula 1730 may snap into the dock, and the dock can be removable from the fourth linkage 1710D. Not fixedly holding onto the cannula can provide advantages when looking to adapt from an endoscopic procedure to a laparoscopic procedure arm, however the proximity between the fourth linkage 1710D and the portion of the insertion axis that passes through the cannula makes it possible to provide a dock to hold the cannula. Such a dock can help resolve medical instrument forces and keep the cannula aligned with the medical instrument axis for medical instrument exchange. This dock can be removable for when the robotic arm 1700 is to be configured for an endoscopic procedure, and the fourth linkage 1710D can include a coupling for attaching to the dock, an additional instrument driver, or another type of attachment, like a patient introducer.

The specific depicted locations of the axes 1735A, 1735B, 1735C can be varied depending upon the positioning of the robotic arm 1700, with the yaw axis 1735A extending through the center of the first motorized joint 1705A and the insertion axis 1735B extending through the instrument driver 1720 coupled to the second motorized joint 1705E. It will be appreciated that simultaneous actuation of multiple joints 1705A-1705E can move the instrument 1725 along or about multiple axes simultaneously. The yaw axis 1735A can be considered as the axis of rotation of revolute joint 1705A and the co-axial axis of rotation of the motion translated to the medical instrument 1725. The present disclosure also refers to the yaw axis 1735A as a "first axis," the insertion axis 1735B as a "second axis," and the pitch axis 1725C as a "third axis."

Actuation of the motorized joints 1705A-1705E of robotic arm 1700 can be controlled programmatically by the controller 206 (automatically or in response to user guidance at console 200) based on different sets of motion constrains corresponding to different medical procedures. For example, in a laparoscopic configuration, configuring the robotic arm 1700 into a low-inertia remote center laparoscopic system is achieved by identifying a remote center 1745 location (corresponding to a point on a cannula and/or a location of an incision in the patient's body), orienting the revolute first axis 1735A to pass through the remote center 1745, constraining actuation of the three intermediate RRP joints (motorized joints 1705B, 1705C, and 1705D) based on software instructions to form remote pitch axis 1735C fixed in space and passing through the remote center 1745, and orienting the distal prismatic axis (along the linear distal face 1715B of the fourth linkage 1710D) parallel to the insertion axis 1735B such that the medical instrument 1725 is inserted through the remote center 1745. Thus, in this first mode of operation, the structures of the robotic arm 1700 that create the first axis 1735A and second axis 1735C are oriented such that these axes pass through the location of the remote center 1745, while the remote pitch axis 1735C is defined by the software constraints and fixed in space to pass through the remote center 1745. During use in the first mode, actuation of the motorized joints 1705A-1705E is controlled to maintain these three axes 1735A, 1735B, 1735C passing through the remote center 1745. Thus, in the first mode the robotic arm 1700 can be considered as a RRRPP serial chain manipulator with a first R axis 1735A configured to point towards the remote center 1745, a last P axis configured to be parallel to the insertion axis 1735B, and a software-constrained remote pitch axis 1735C formed by the intermediate RRP joints, where the robotic arm 1700 is controlled such that the axes 1735A, 1735B, 1735C intersect with one another at a pre-identified a remote center location. The remote center geometry (e.g., its distance along the yaw axis 1735A from the first motorized joint 1705A) can be adjusted during use, as described in more detail below with respect to FIGS. 24A and 24B.

In an endoscopic configuration, the software constraint relating to the remote center is removed, and the motorized joints 1705A-1705E are instead operated with respect to a virtual rail. A virtual rail can be considered as a linear axis in space that is aligned with an opening of a patient, for example a natural orifice leading to an interior luminal network of the patient. In some examples, an additional instrument driver 1720 can be affixed to one end of the fourth linkage 1710D in endoscopic mode. In some examples, motorized joints 1705A-1705E can be used to position a series of robotic arms 1700 next to each other with their insertion axes aligned along the virtual rail. The insertion axes of the various instrument drivers and/or arms need to be coincident, however the instrument drivers can be spaced apart along the virtual rail to provide a maximum workspace and/or to avoid collisions.

In some embodiments, the instrument driver 1720 can rotate relative to the second motorized joint 1705E as, for some endoscopic procedures, it is desirable to have a top-loading medical instrument. This can be achieved by adding a rotary degree of freedom between the instrument driver 1720 and second motorized joint 1705E. This degree of freedom can either be active or a passive setup joint. A passive setup joint can include detent positions or an integer number of positions where it can be latched, for example in order to facilitate rotating the instrument driver 1720 in 90-degree increments.

The robotic arm 1700 can be delivered by an active or passive setup joint. If the setup joint is active, the setup joint can re-position the workspace of the robotic arm 1700 intraoperatively while maintaining intersection of the axes 1735A, 1735B, 1735C with the remote center. The setup joint can also reposition the first motorized joint 1705A such that the first axis 1735A passes through the remote center. One advantage of using such a setup joint is that this puts a set of fast axes (e.g., axes with performance suitable for performing laparoscopic procedures with a limited workspace) on set of slow axes (e.g., axes that are not suitable for performing laparoscopic procedures alone but have a large workspace). As such, it is possible to perform null-space movements to keep the medical instrument 1725 centered on the fast axes, thus enabling the robotic arm 1700 to have a fast performance over a large workspace. This design reflects a trade-off for the robotic arm 1700 between range of motion of the robotic arm 1700 and minimizing size while still satisfying the requirements of laparoscopic procedures.

Figure 18:
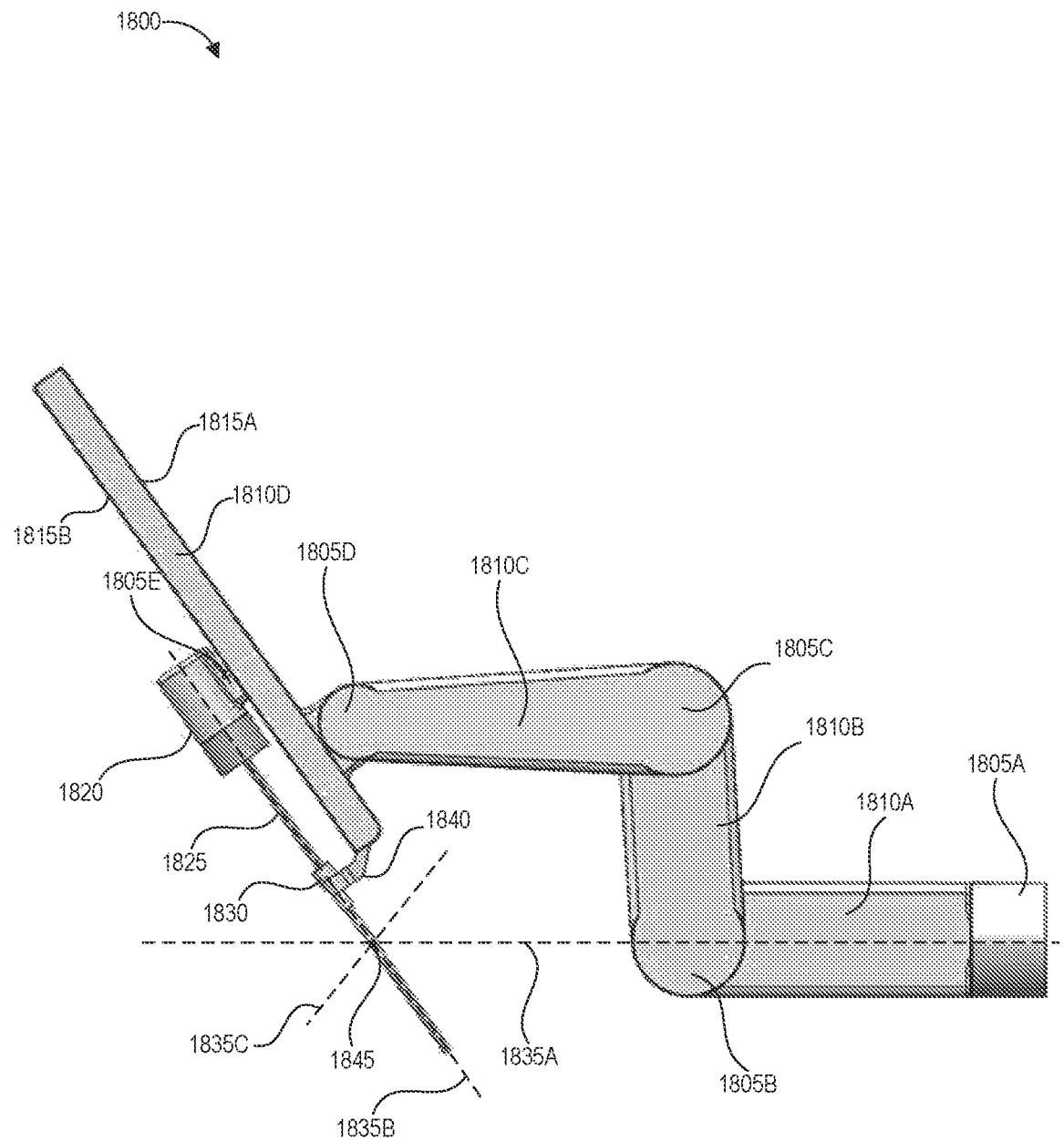
FIG. 18 illustrates another example of a robotic arm usable with the systems and components depicted in FIGS. 1-16.

FIG. 18 illustrates another example of a robotic arm 1800 usable with the systems and components depicted in FIGS. 1-16. The robotic arm 1800 comprises an RRRRP serial chain manipulator, with such joint labeling beginning at the proximal-most joint 1805A and moving serially along the robotic arm towards the distal-most joint 1805E.

The robotic arm 1800 includes a number of motorized joints 1805A-1805E connected in serial fashion by linkages 1810A-1810D. The first linkage 1810A connects the first motorized joint 1805A and the third motorized joint 1805B, the second linkage 1810B connects the third motorized joint 1805B to the fourth motorized joint 1805C, the third linkage 1810C connects the fourth motorized joint 1805C to the fifth motorized joint 1805D, and the fourth linkage 1810D connects the fifth motorized joint 1805D to the second motorized joint 1805E. In the embodiment of FIG. 18, the second linkage 1810B is shorter than the first linkage 1810A such that the fourth motorized joint 1805C can rotated by actuation of the third motorized joint 1805B in a full circle. For example, the fourth motorized joint 1805C can be rotated from its illustrated position on a first side of the first linkage 1810A past the first motorized joint 1805A to a second side of the first linkage 1810A due to the shorter length of the second linkage 1810B. During such a movement, the fourth joint 1805C can be actuated to prevent collision between the first motorized joint 1805A and the structures positioned distally from the fourth motorized joint 1805C (e.g., third linkage 1810C, fifth motorized joint 1805D, fourth linkage 1810D, second motorized joint 1805E, instrument driver 1810, and medical instrument 1825).

A first motorized joint 1805A at the proximal end of the robotic arm (e.g., closest to setup joints or a base of the robotic system to which the robotic arm 1800 is attached) is a revolute joint that causes rotational motion of medical instrument 1825 around yaw axis 1835A. A second motorized joint 1805E at the distal end of the robotic arm (e.g., closest to the medical instrument 1825) is a prismatic joint that moves linearly along distal face 1815B of the fourth linkage 1810D. Additional motorized joints 1805B, 1805C, 1805D are positioned serially between the first and second motorized joints, and are revolute joints that each rotate in a plane positioned orthogonally to the plane of rotation of the first motorized joint 1805A. Actuation of the additional motorized joints 1805B, 1805C, 1805D can cause the medical instrument 1825 to rotate about pitch axis 1835C. Each motorized joint 1805A-1805E can comprise a motor, a position sensor, and a gearbox, as described above with respect to the robotic arm 1700. Output from the position sensors of each of the motorized joints 1805A-1805E can be used to control actuation of the robotic arm 1800 in the operational modes described herein.

An instrument driver 1820 can be coupled to the second motorized joint 1805E to secure and/or manipulate medical instrument 1825. The instrument driver 1820 can be the instrument driver described with respect to FIG. 12 in some embodiments. Movement of the second motorized joint 1805E along the distal face 1815B of the fourth linkage 1810D and/or coordinate movement of the additional motorized joints 1805A-1805E, alone or together with one or more setup joints, can translate into linear motion of the medical instrument 1825 along the insertion axis 1825B. The instrument driver 1820 can move the medical instrument 1825 in other degrees of freedom, for example roll of the medical instrument 1825 around the insertion axis 1825B, deflection of the tip of a steerable medical instrument, and the like. The medical instrument 1825 can be any endoscopic or laparoscopic tool, for example a bronchoscope, gastroscope, ureteroscope, colonoscope, steerable catheter, a laparoscope, a tool positioned within the working channel of such a scope (e.g., needles, forceps, cytology brushes, augers, etc.), electrosurgical shears, and other medical instruments used in the disclosed procedures.

In some medical procedures, the instrument 1825 can extend into a cannula 1830 positioned for example in an incision forming an opening into the body of a patient. The robotic arm 1800 can further include a dock 1840 that can couple the fourth linkage 1810D to the cannula 1830. The cannula 1830 may snap into the dock, and the dock can be removable from the fourth linkage 1810D. Not fixedly coupling the robotic arm 1800 to the cannula 1830 can provide advantages when looking to adapt from an endoscopic procedure to a laparoscopic procedure arm, however the proximity between the fourth linkage 1810D and the portion of the insertion axis that passes through the cannula 1830 makes it possible to provide dock 1840 to hold the cannula. Dock 1840 can help resolve medical instrument forces and keep the cannula aligned with the medical instrument axis for medical instrument exchange. Dock 1840 can be removable for when the robotic arm 1800 is to be configured for an endoscopic procedure, and the fourth linkage 1810D can include a coupling for attaching to the dock 1840, an additional instrument driver, or another type of attachment, like a patient introducer. In some medical procedures the instrument 1825 can extend directly into a natural orifice forming an opening into a luminal network of a patient and thus the cannula 1830 can be omitted.

The specific depicted locations of the axes 1835A, 1835B, 1835C can be varied depending upon the positioning of the robotic arm 1800, with the yaw axis 1835A extending through the center of the first motorized joint 1805A and the insertion axis 1835B extending through the instrument driver 1820 coupled to the second motorized joint 1805E. It will be appreciated that simultaneous actuation of multiple joints 1805A-1805E can move the instrument 1825 along or about multiple axes simultaneously. The yaw axis 1835A can be considered as the axis of rotation of revolute joint 1805A and the co-axial axis of rotation of the motion translated to the medical instrument 1825. The present disclosure also refers to the yaw axis 1835A as a "first axis," the insertion axis 1835B as a "second axis," and the pitch axis 1825C as a "third axis."

Actuation of the motorized joints 1805A-1805E of robotic arm 1800 can be controlled programmatically by the controller 206 (automatically or in response to user guidance at console 200) based on different sets of motion constrains corresponding to different medical procedures. In a first mode suitable for laparoscopic procedures, as described above with respect to the robotic arm 1700, the robotic arm 1800 can be controlled via a software-constrained remote center architecture such that the first R axis 1835A extends through the remote center 1845, the software-defined remote pitch axis 1835C passes through the remote center 1845, and the insertion axis 1835B points through the remote center 1845. This remote center constraint can be removed to operate the robotic arm 1800 in a second mode suitable for an endoscopic procedure, where in the second mode the robotic arm 1800 is controlled with respect to a virtual rail, such that the insertion axis 1835B is maintained co-axial with the virtual rail.

It will be appreciated with respect to FIGS. 17 and 18 that the illustrated shapes and sizes of the linkages can be varied. For example, the linkages may be curved rather than straight in variations of the illustrated embodiments, and certain linkages may be lengthened or shortened.

2. Overview of Example Operational Modes

Figure 19A:
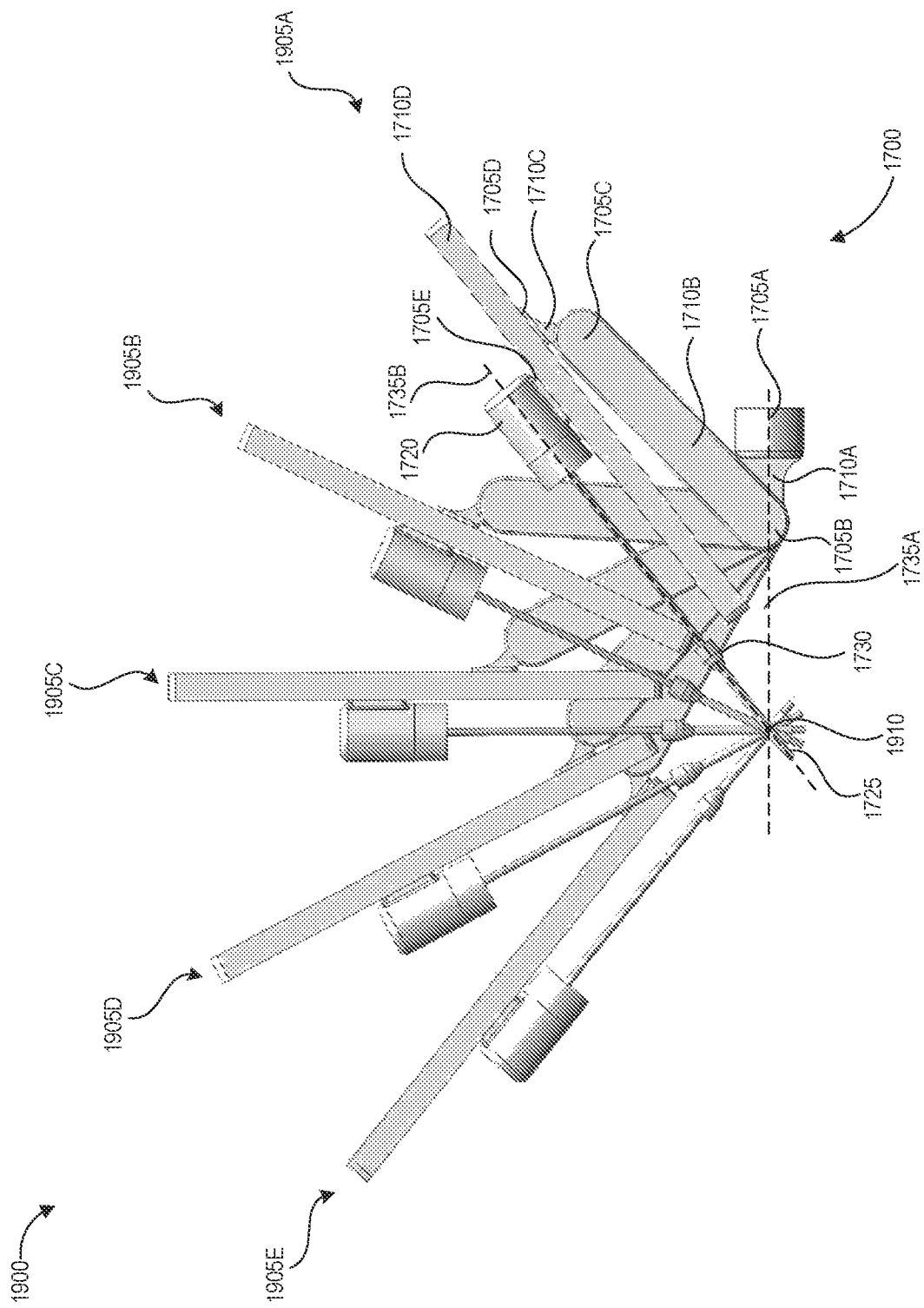
FIG. 19A depicts the robotic arm of FIG. 17 begin actuated in a first mode of operation.

FIG. 19A depicts the robotic arm 1700 of FIG. 17 begin actuated in a first mode of operation 1900. The first mode of operation 1900 can be suitable for laparoscopic procedures. The robotic arm 1800 of FIG. 18 can be operated in a similar manner in the first mode of operation. For clarity in the drawing, certain reference numbers shown for the robotic arm 1700 in FIG. 17 that are not specifically referenced in the discussion of FIG. 19A are omitted from FIG. 19A, and the reference numbers relating to the structures of the robotic arm 1700 are provided on only the first position 1905A of the five illustrated positions 1905A-1905E.

In the first mode of operation 1900, the movement of the robotic arm 1700 is controlled such that the first axis 1705A points through the remote center 1910 and the second axis 1735B also points through the remote center 1910. In the illustrated example, the software-defined remote pitch axis (the third axis) extends through the page of FIG. 19A at the location of the remote center 1910.

During use in the first mode of operation 1900, the robotic arm 1700 can be positioned in a number of different positions 1905A-1905E (as well as other in positions intermediately located between the illustrated positions) that span a range of possible positions between the first position 1905A and the last position 1905E. In each position, the motorized joint 1705A is oriented so that the first axis 1705A points through the remote center 1910. Further, in each position the actuations of motorized joints 1705B-1705D are cooperatively controlled such that the third axis intersects with the remote center 1910. Further, in each position the instrument driver 1720 is positioned such that the second axis 1735B points through the remote center 1910. The movement between the illustrated positions 1905A-1905E is effected by controlling the third, fourth, and fifth motorized joints 1705B-1705D to rotate the medical instrument 1725 around the remote pitch axis and the remote center 1910. Other movements are also possible while controlling the robotic arm 1700 under the constraints of the first mode of operation 1900.

As illustrated, the position and orientation of the first linkage 1710A may remain stationary, or the orientation may rotate around the first axis 1735A while its position remains stationary. In some embodiments the position of the first linkage 1710A can be varied by setup joints while maintaining intersection of the first axis 1735A with the remote center 1910. The positions and orientations of the second, third, and fourth linkages 1710B-1710D can vary relative to the position of the first motorized joint 1705A and relative to one another as the robotic arm 1700 is rotated around the remote pitch axis through the range of positions 1905A-1905E under control of the first operating mode 1900. Although the instrument driver 1720 as depicted in FIG. 19B is maintained a fixed distance from the cannula 1730, in other embodiments distance between the instrument driver 1720 and the cannula 1730 can be varied to adjust the insertion depth of the medical instrument 1725 within the body of the patient.

Figure 19B:
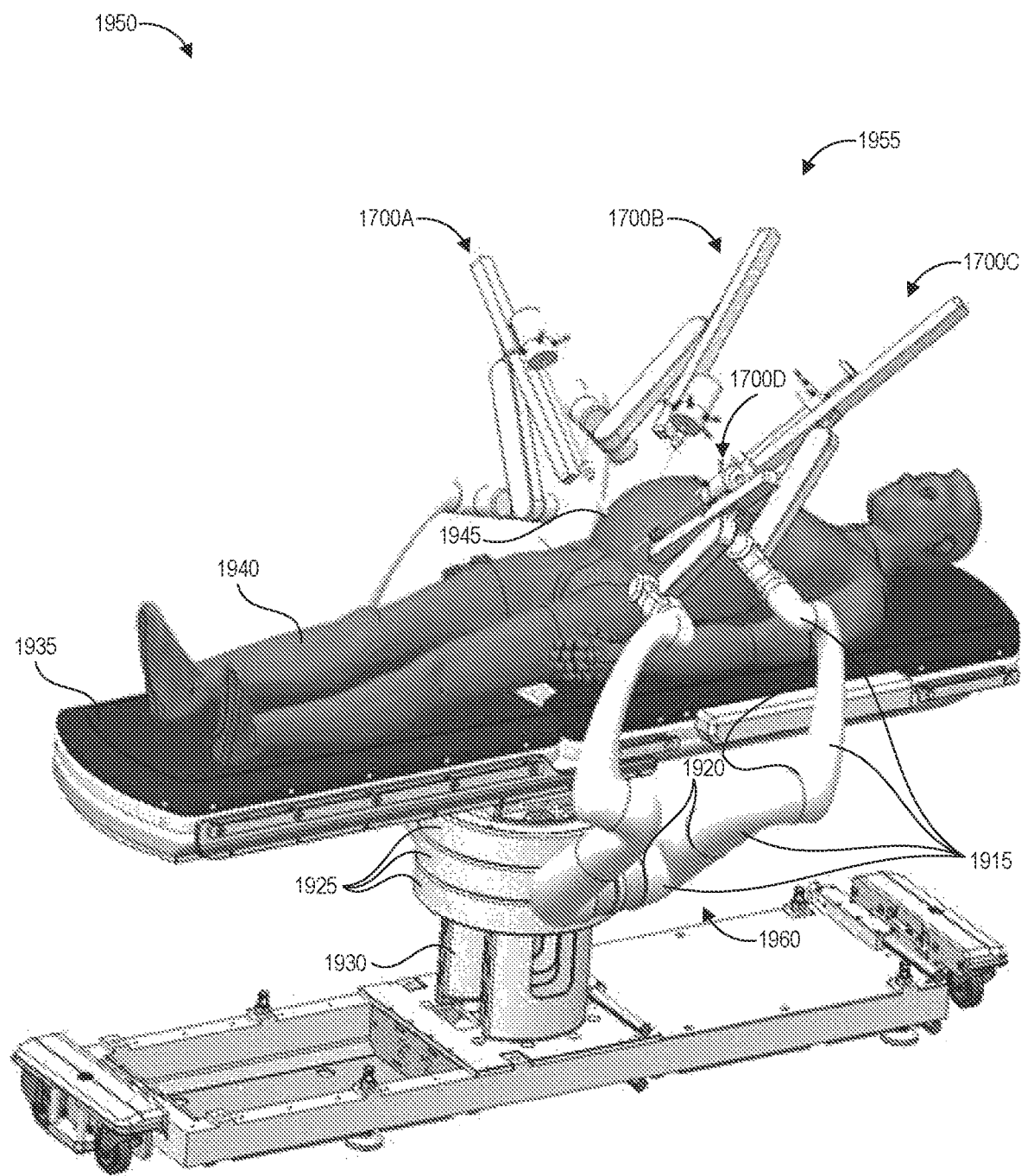
FIG. 19B depicts a table-based robotic system including a number of robotic arms as depicted in FIG. 17 configured for operating in the first mode for a laparoscopic procedure.

FIG. 19B depicts a table-based robotic system 1955 including a number of robotic arms as depicted in FIG. 17 in a first configuration 1950 suitable for operating in the first mode 1900 for a laparoscopic procedure. As illustrated, four robotic arms 1700A-1700D each control a medical instrument to rotate about a remote center located at (or near) an incision 1945 in the abdomen of a patient 1940. For clarity in the drawing, certain reference numbers shown for the robotic arm 1700 in FIG. 17 that are not specifically referenced in the discussion of FIG. 19A are omitted from FIG. 19A, and only one incision 1945 is labeled though each robotic arm 1700A-1700D is controlled with respect to a different remote center located at (or near) a different incision. The robotic arm 1800 can alternatively be used in place of one, some, or all of the robotic arms 1700 in other embodiments, and table-based robotic system 1950 can include greater or fewer than four robotic arms.

The table-based robotic system 1950 includes four setup arms 1960 each including a number of setup joints 1920 serially coupled by linkages 1915. The setup joints 1920 of a setup arm 1960 can be passive, active, or a mix. The configuration of a setup arm 1960 can be varied depending upon the intended usage of the table-based robotic system 1950. Each setup arm 1960 is attached to one of the robotic arms 1700A-1700D and thus positions the corresponding robotic arm in the space surrounding the patient 1940.

In the illustrated embodiment, the setup arms 1960 are attached to carriages 1925 that are secured around a column 1930 positioned under a bed such that setup arms 1960 emerge from below patient table 1935. The column 1930 is illustrated with three carriages 1925 and four robotic arms 1700A-1700D, where two arms are attached to the same carriage and one of the carriages may have no arms and may be omitted. In other embodiments the third carriage can have an additional arm or two arms, and the specific configuration of carriages and robotic arms can be modified based on the requirements of the system 1950. Further, the disclosed robotic arms are not limited to a table-based system as illustrated, and in other embodiments can be mounted to a movable cart or ceiling-mounted base. Regardless of how they are mounted, a robotic system 1950 including multiple arms 1700A-1700D retains the advantage of being able to perform both laparoscopic procedures and endoscopic procedures with the same system 1950.

During operation in the first mode, a single controller 206 or a group of controllers in communication with one another may be used to control motion of each of the robotic arms 1700A-1700D and setup arms 1960 so that the various physical structures do not collide or interfere with one another. Each controller 206 can include one or more processors and an associated memory configured with computer-executable instructions for controlling joint actuation in various operation modes based on user guidance via input controls, data from joint position encoders, stored mode-specific operational constraints, and stored size parameters of the structures of the robotic arms 1700A-1700D. Accordingly, the controller 206 may limit the range of motion or workspace of a particular arm or arms in order to prevent collisions. Such a limitation can be set at the beginning of a procedure or can be varied dynamically during the procedure based upon the positions of other arms. Though not illustrated, in some embodiments the table-based robotic system 1950 can include one or more image sensing devices positioned around the table 1935 and in communication with the controller 206 in order to identify positions of medical personnel around the patient and to control the robotic arms 1700A-1700D to avoid the positions of the medical personnel. The controller 206 can be located within the table 1935, column 1930, or a control system (for example console base 201), or distributed among these structures.

Figure 20A:
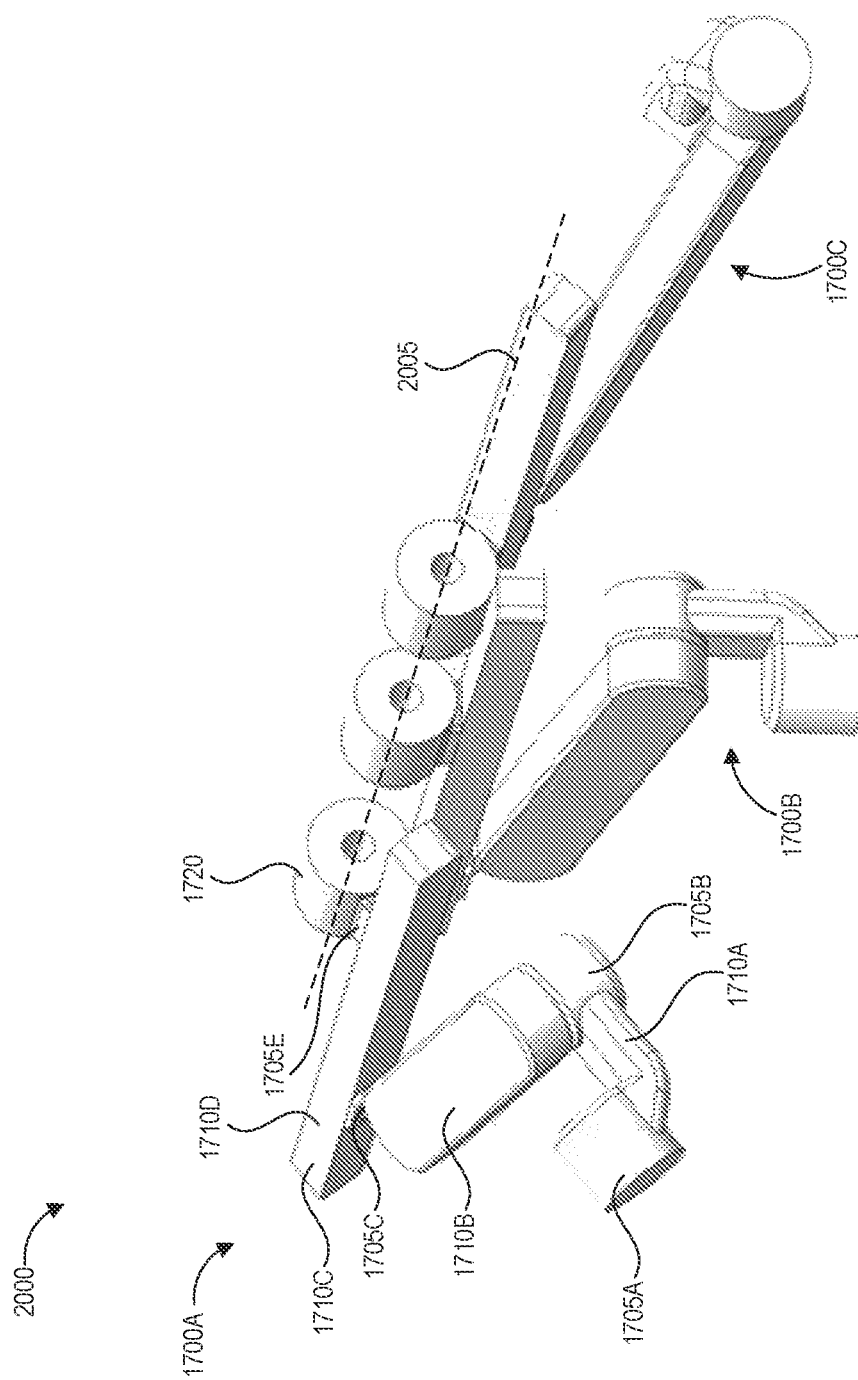
FIG. 20A depicts a number of the robotic arms of FIG. 17 configured in a second mode of operation.

FIG. 20A depicts three of the robotic arms 1700A-1700C of FIG. 17 configured in a second mode of operation 2000. The second mode of operation 2000 can be suitable for endoscopic procedures. The robotic arm 1800 of FIG. 18 can be operated in a similar manner in the second mode of operation 2000. For clarity in the drawing, certain reference numbers shown for the robotic arm 1700 in FIG. 17 that are not specifically referenced in the discussion of FIG. 20A are omitted from FIG. 20A, and the reference numbers relating to the structures of the robotic arm 1700 are provided only on the first robotic arm 1700A.

In the second mode of operation 2000, robotic arms 1700A-1700C are positioned such that the insertion axes (not labeled) that pass through the instrument driver 1720 of each robotic arm 1700A-1700C are aligned to be co-axial with virtual rail 2005. The robotic arms 1700A-1700C are further positioned such that none of the linkages 1710A-1710D, joints 1705A-1705E, or instrument driver 1720 of a particular robotic arm interferes with the required ranges of motion of the instrument drivers of the other robotic arms. Thus, the robotic arms 1700A-1700C can each be used to position and actuate (via the instrument driver) one of a number of coaxial medical instruments during an endoscopic procedure. For example, robotic arm 1700A may position and actuate a bronchoscope having a working channel, robotic arm 1700B may position and actuate a catheter (steerable or non-steerable) extending into and potentially beyond the working channel of the bronchoscope, and robotic arm 1700C may position a conduit that extends into the catheter and is coupled at its distal end to a needle or other medical tool. For example, robotic arm 1700C can extend and retract the needle relative to the catheter by actuating the second motorized joint 1705E, fifth motorized joint 1705D, and/or a combination of the motorized joints 1705B-1705E (with or without setup joint movement).

Figure 26:
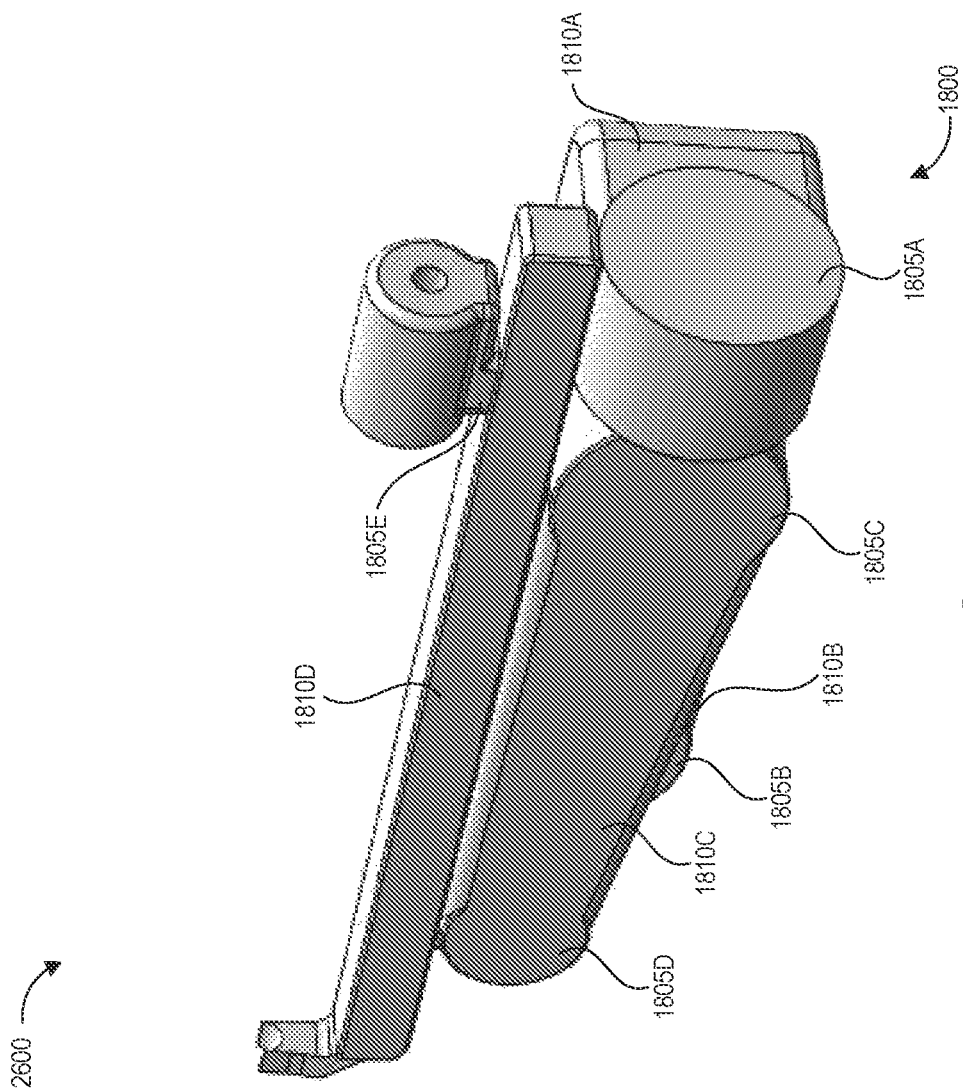
FIG. 26 depicts the robotic arm of FIG. 18 in a storage configuration.

FIG. 20B depicts a second configuration 2050 of the table-based robotic system 1955 of FIG. 19B including robotic arms 1700A-1700C configured as shown in FIG. 20A for operating in the second mode 2000 suitable for an endoscopic procedure. The fourth arm 1700D is folded into a compact storage configuration (one example of which is illustrated in FIG. 26 with respect to arm 1800) and is not visible in the view of FIG. 20B. The robotic arms 1700A-1700C position concentric endoluminal medical instruments 1725A, 1725B, 1725C along the virtual rail 2005 that is shown as being co-axial with the insertion axis 1725B of each robotic arm 1700A-1700C. The virtual rail 2005 is aligned with the natural orifice 2045 (mouth) of patient 1940.

In some medical procedures, it may be desirable to have one or a subset of the robotic arms 1700A-1700D of the table-based robotic system 1955 operating in the first mode 1900 and another or another subset of the robotic arms 1700A-1700D operating in the second mode 2000. For example, some uteroscopic procedures involve a first medical instrument that enters the kidney through an incision, which could be controlled by a robotic arm in the first mode 1900, as well as a second medical instrument passed endoluminally to the kidney through the ureter, which could be controlled by a robotic arm in the second mode 2000.

Figure 21A:
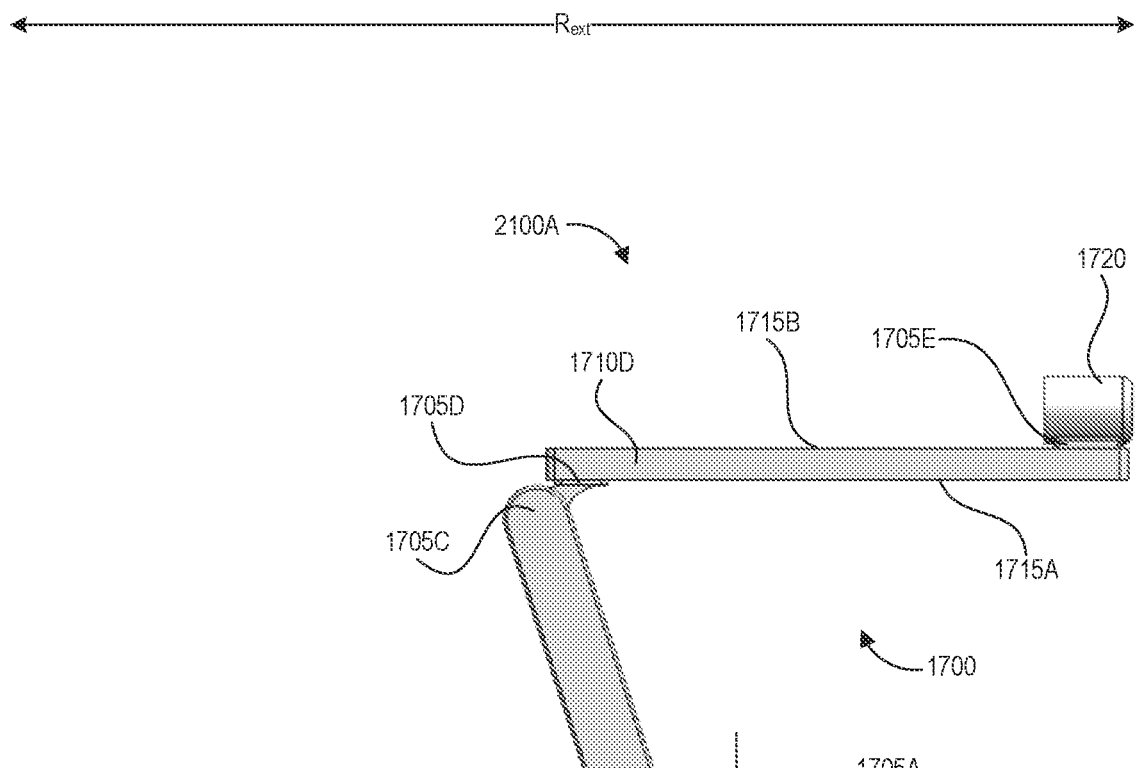
FIGS. 21A and 21B depict a range of positions for an instrument driver mounted to the robotic arm of FIG. 17.
Figure 21B:
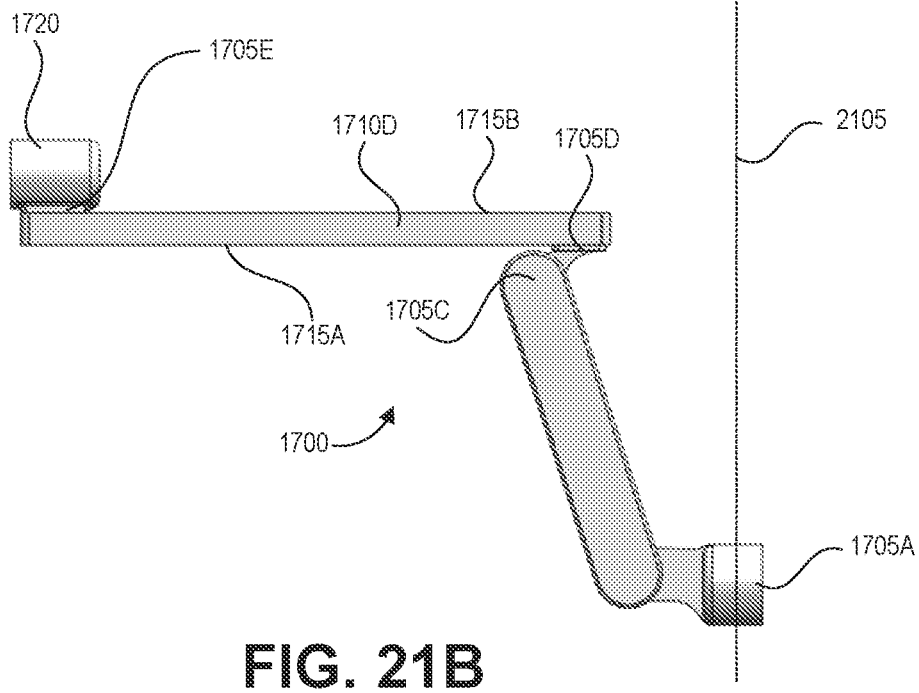

FIGS. 21A and 21B depict a range Rext of position options for the instrument driver 1720 mounted to the robotic arm of FIG. 17 given a fixed location of the fourth motorized joint 1705C. For example, the location of the fourth motorized joint 1705C may be fixed in the second mode of operation 2000 in order to maintain a coaxial insertion axis and software-constrained virtual rail location. The range Rext is provided by a "double insertion axis" resulting from the linear movement of the second motorized joint 1705E along the distal face 1715B of the fourth linkage 1710D and the linear movement of the fifth motorized joint 1705D along the proximal face 1715A of the fourth linkage 1710D. FIGS. 21A and 21B are illustrated with the first motorized joint 1705A aligned along axis 2105 in order to accurately depict the range $R_{ext}$.

In FIG. 21A, the robotic arm 1700 is positioned in a first configuration 2100A with the second motorized joint 1705E and instrument driver 1720 positioned at a first end of the fourth linkage 1710D and the fifth motorized joint 1705D positioned at a second end of the fourth linkage 1710D, the second end opposing the first end with the proximal and distal faces 1715A, 1715B extending therebetween. In FIG. 21B, the robotic arm 1700 is positioned in a second configuration 2100B with the second motorized joint 1705E and instrument driver 1720 positioned at the second end of the fourth linkage 1710D and the fifth motorized joint 1705D positioned at the first end of the fourth linkage 1710D. As illustrated, this provides a range Rext of possible locations to which the instrument driver 1720 may be moved using just the fifth and second motorized joints 1705D, 1705E, for example during operation of the robotic arm 1700 in the second mode of operation 2000. Though the instrument driver 1720 is depicted as facing the same direction in FIGS. 21A and 21B, the instrument driver 1720 may be rotated 180 degrees to cover the entire depicted range Rext. The double insertion axis thus provides advantages for endoscopic procedures, because it gives an insertion range of motion of that is double the length of the range of motion that would be provided using a single prismatic joint at the distal end of the robotic arm (for example, as in the embodiment of FIG. 18). This greater range of motion gives the robotic arm 1700 greater flexibility with endoscopic procedures.

FIGS. 22A-22D depict a series of example steps of a setup process 2200 for setting up the robotic arm of FIG. 18 to operate in the first mode 1900 depicted in FIG. 19A. Similar setup processes can be implemented using the robotic arm 1700 and other disclosed variations.

Figure 22A:
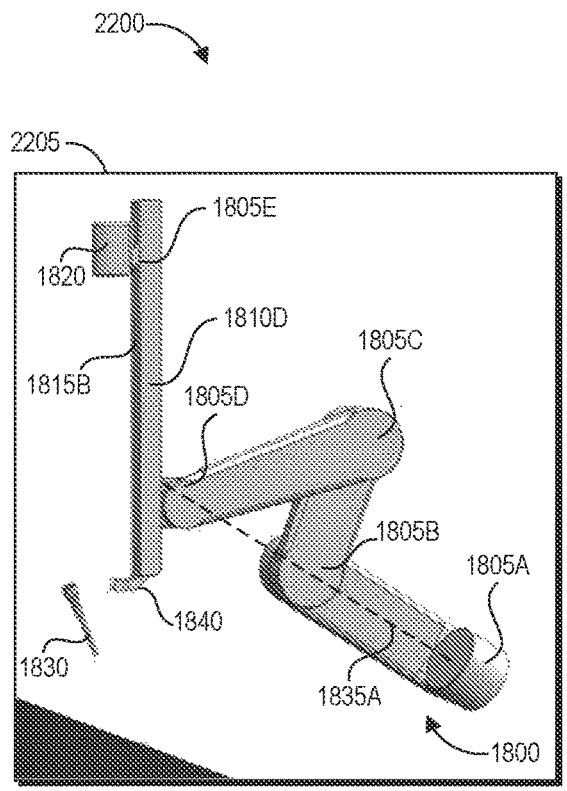
FIGS. 22A-22D depict a series of example steps for setting up the robotic arm of FIG. 18 to operate in the first mode depicted in FIG. 19A.

Block 2205 shown in FIG. 22A depicts the robotic arm 1800 with the dock 1840 uncoupled from cannula 1830. Though depicted as floating in space, in use the cannula 1830 may be positioned within an opening into the body of a patient.

Figure 22B:
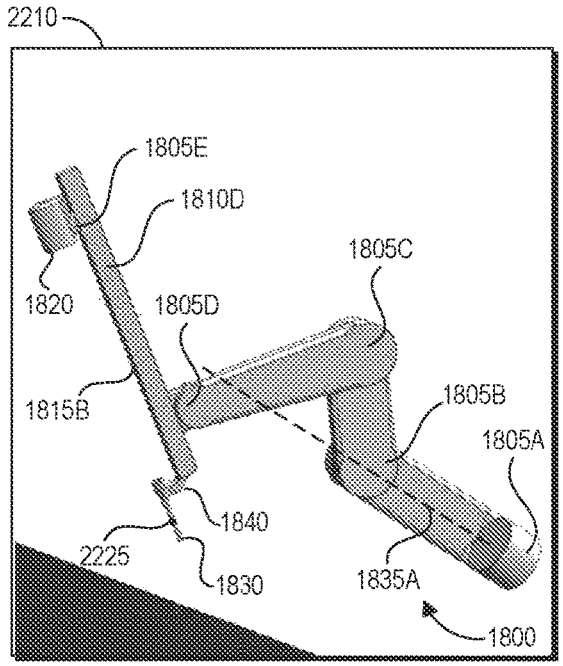

At block 2210 shown in FIG. 22B, the dock 1840 of the robotic arm 1800 is coupled to the cannula. For example, the motorized joints 1705A-1705E can be operated in a passive mode such that a user can manually move the robotic arm 1800 to connect the dock 1840 and the cannula 1830. The controller 206 of the robotic arm 1800 can identify when the cannula 1830 is docked, for example by a sensor or mechanical button in the dock 1840 or based on user input at a control system. Once docked, the controller 206 can identify the location of the remote center 2225 as a point along or within the cannula 1830. The location may be identified based on a pre-defined spatial relationship between the docked portion of the cannula 1830 and the remote center, based on user input designated a depth of insertion of the cannula into the opening, or identified automatically and then adjusted by user input. At block 2210, the yaw axis 1835A (the axis of revolution of first motorized joint 1705A) does not yet intersect with the remote center 2225, but the insertion axis (not illustrated) passes through the remote center 2225 due to the docking of the cannula 1930 and the geometry of the dock 1840.

Figure 22C:
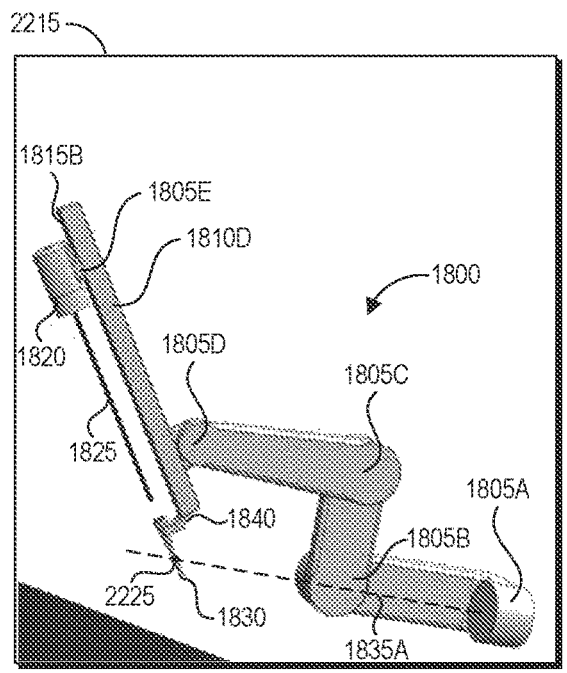

At block 2215 shown in FIG. 22C, the controller 206 can actuate setup joints (such as setup joints 1920 or a variation thereof) to position the first axis 1835A to intersect with the identified location of the remote center 2225. At the same time, the controller 206 can actuate some or all of the motorized joints 1705A-1705E to maintain a fixed position and orientation of the cannula 1830. As such, the actuation of robotic arm 1800 and any setup joints at block 2215 can be considered as a null-space movement that maintains the orientation of the insertion axis and the location of the remote center 2225.

Figure 22D:
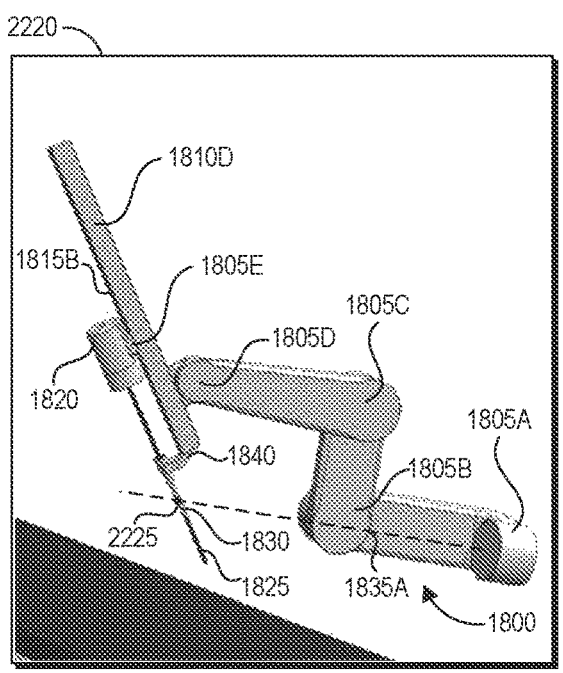

At block 2220 shown in FIG. 22D, the instrument driver 1820 is actuated along the distal surface 1815B of the fourth linkage 1810D in order to insert the medical instrument 1825 through the cannula 1830. Block 2220 can further involve actuation of the robotic arm 1800 in the first mode 1900 described herein.

The setup process 2200 provides advantages compared to setup with existing systems having mechanical remote centers that maintain a parallelogram (or virtual parallelogram) configuration of the robotic arm linkages. In such existing systems, a user needs to move the whole arm around to connect it to the cannula, which is accomplished with passive setup joints. A few challenges with this existing process are that either the user has to work hard to make the movements fluid during docking or the user efforts can be minimized at the cost of forcing other engineering and design tradeoffs, and the high inertia of the arm makes small adjustments difficult. With the ability to break the "parallelogram" of the arm by implementing a software-based remote center constraint, the disclosed robotic arms have additional degrees of freedom relative to the described existing systems, and these additional degrees of freedom allow a user to easily dock to the cannula 1830. The controller 206 can then actuate the motorized joints 1805A-1805E in order to reconstruct the remote center constraint (and create a parallelogram if desired, as described in more detail below), as described above with respect to block 2215. This is achieved by having the yaw axis point above the remote center, and then having the arm in an admittance mode. Then the setup person has 3 DOF of positioning control for the cannula attachment, and can dock it.

Figure 23A:
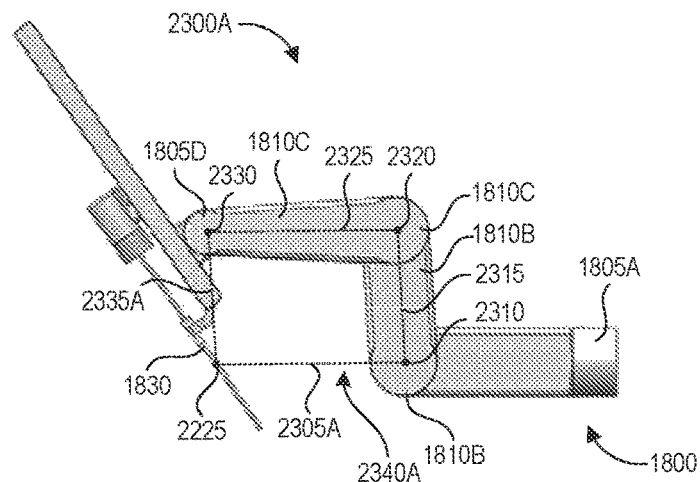
FIGS. 23A-23C depict different sub-modes for operating the robotic arm of FIG. 18 in the first mode depicted in FIG. 19A.
Figure 23B:
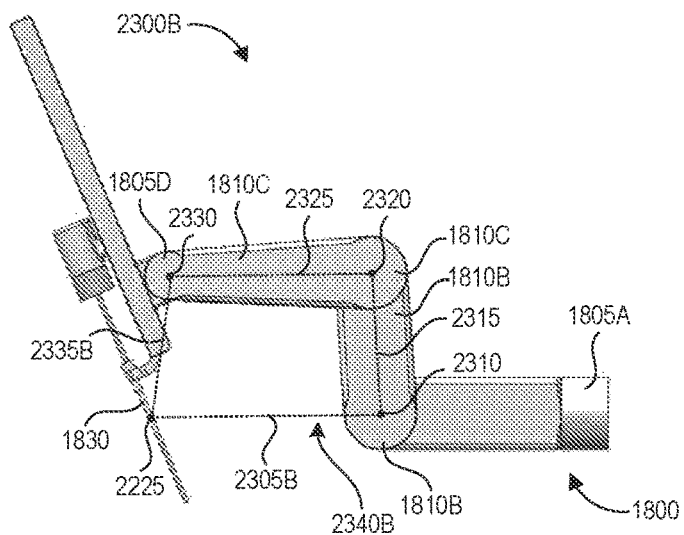
Figure 23C:
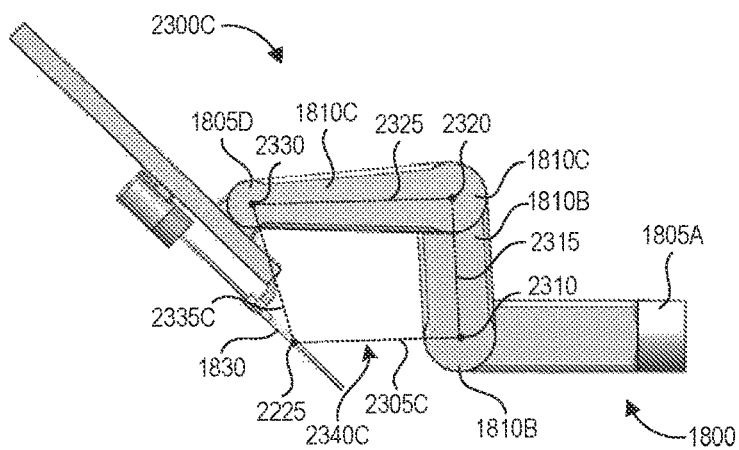

FIGS. 23A-23C depict different sub-modes for operating the robotic arm of FIG. 18 in the first mode 1900 depicted in FIG. 19A. Because the open kinematic chain of the robotic arm 1800 is not mechanically constrained to maintain a parallelogram, the controller 206 can vary the distance of the third motorized joint 1810B from the remote center 2225 along the yaw axis 1835A and can compute the kinematics needed to actuate the motorized joints 1805A-1805E to achieve the needed movement of the medical instrument 1825 while operating under the remote center architecture described for the first mode 1900. This achieves an additional setup degree of freedom, which can beneficially simplify the setup joint system. The tradeoffs of this additional degree of freedom are a relatively more limited range of motion around the pitch axis and non-linear joint velocities for the pitch motion, which in turn impart a requirement of faster joints in the design of the robotic arm 1800 in order to get an equivalent pitch velocity. These nonlinearities can be minimized through design optimization and further workspace limiting.

FIG. 23A depicts a parallelogram setup 2300A in which the configuration of the robotic arm 1800 forms a parallelogram 2340A. As implied by the geometric terminology, the parallelogram 2340A has a first set of parallel sides 2325, 2305A of equal length to one another and a second set of parallel sides 2315, 2335A of equal length to one another. Side 2325 is defined along the third linkage 1810C between a center 2330 of the fifth motorized joint 1805D and a center 2320 of the fourth motorized joint 1805C. Side 2315 is defined along the second linkage 1810B between a center 2330 of the fourth motorized joint 1805C and a center 2310 of the third motorized joint 1805B. Side 2335A is defined between a center 2330 of the fifth motorized joint 1805D and the remote center 2225. Side 2305A, also referred to as a "virtual link," is defined between the remote center 2225 and the center 2310 of the third motorized joint 1805B. In some embodiments, the controller 206 can configure the robotic arm 1800 in the parallelogram setup 2300A at block 2215 of FIG. 22C.

FIG. 23B depicts a broken parallelogram setup 2300B having a longer virtual link 2305B than the virtual link 2305A in parallelogram setup 2300A. Such a configuration is achievable due the open kinematic chain and software-constrained remote center architecture of the arm 1800. In the broken parallelogram setup 2300B, the virtual link 2305B is still parallel to the side 2325, however the length of the virtual link 2305B is greater than the length of side 2325. As a result, the sides 2335B and 2315 are not parallel and may have unequal lengths. Accordingly, a "broken" parallelogram 2340B is formed having a longer virtual link 2305B than side 2325. In some embodiments, the controller 206 can configure the robotic arm 1800 in the broken parallelogram setup 2300B at block 2215 of FIG. 22C. In some embodiments, the controller 206 can transition the robotic arm 1800 between the parallelogram setup 2300A and the broken parallelogram setup 2300B intraoperatively by actuating at least some of the motorized joints 1805A-1805E together with powered setup joints. During such a transition, the location of the remote center 2225 remains unchanged.

FIG. 23C depicts a broken parallelogram setup 2300C having a shorter virtual link 2305C than the virtual link 2305A in parallelogram setup 2300A. Such a configuration is achievable due the open kinematic chain and software-constrained remote center architecture of the arm 1800. In the broken parallelogram setup 2300C, the virtual link 2305C is still parallel to the side 2325, however the length of the virtual link 2305C is shorter than the length of side 2325. As a result, the sides 2335C and 2315 are not parallel and may have unequal lengths. Accordingly, a "broken" parallelogram 2340C is formed having a shorter virtual link 2305C than side 2325. In some embodiments, the controller 206 can configure the robotic arm 1800 in the broken parallelogram setup 2300C at block 2215 of FIG. 22C. In some embodiments, the controller 206 can transition the robotic arm 1800 between the parallelogram setup 2300A or broken parallelogram setup 2300B to the broken parallelogram setup 2300C intraoperatively by actuating at least some of the motorized joints 1805A-1805E together with powered setup joints. During such a transition, the location of the remote center 2225 remains unchanged.

Figure 24A:
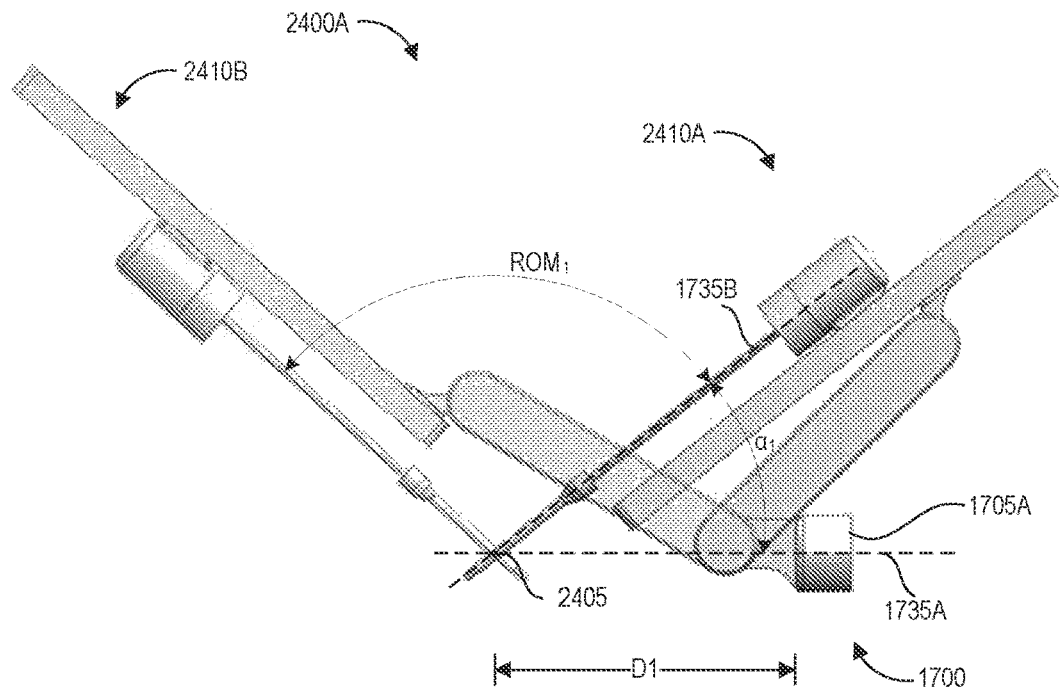
FIGS. 24A and 24B depict different sub-modes for operating the robotic arm of FIG. 17 in the first mode depicted in FIG. 19A.
Figure 24B:
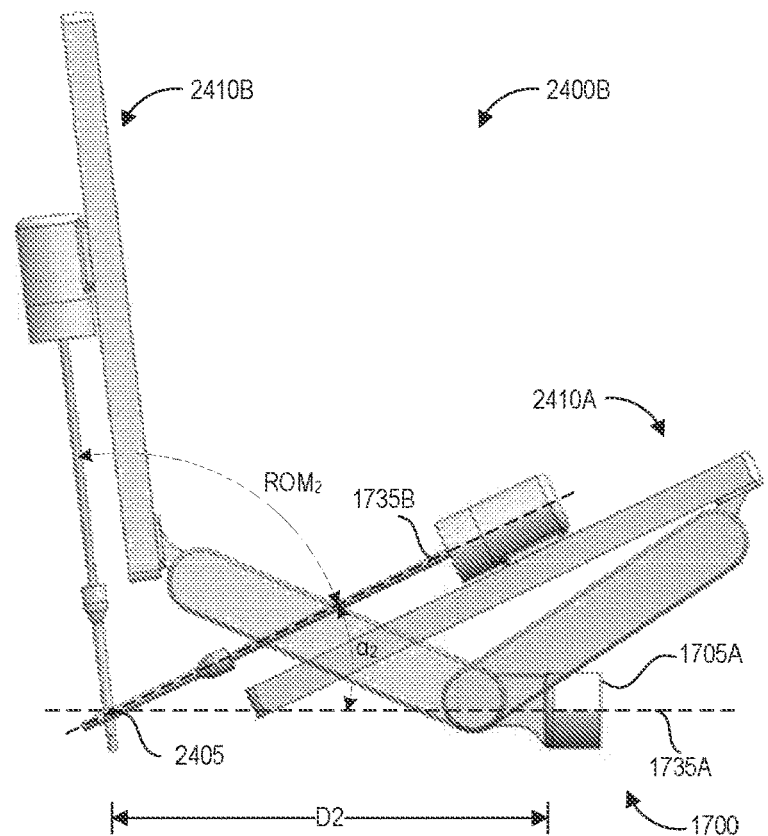

FIGS. 24A and 24B depict different sub-modes for operating the robotic arm 1700 of FIG. 17 in the first mode 1900 depicted in FIG. 19A. The controller 206 can configure the robotic arm 1700 in one of the sub-modes 2400A, 2400B (or a similar sub-mode having a fixed distance between the first motorized joint 1705A and the remote center) at the beginning of operating in the first mode 1900, or can transition the robotic arm 1700 between the sub-modes 2400A, 2400B intraoperatively using powered setup joints. The particular distances between the first motorized joint 1705A and the remote center are provided for example only, and the first motorized joint 1705A and the remote center can be positioned any mechanically possible distance apart along the first axis 1735A in use. Another null-space reconfiguring made possible by the open kinematic chain of the robotic arm 1700 thus is to intraoperatively adjust the distance between the first motorized joint 1705A and the remote center. By doing this, the robotic system can trade off the range of the workspace of the robotic arm 1700 with the capability to work at shallower pitch angles. This can be helpful when there is limited room in which the robotic arm 1700 can operate, for example in order to avoid interfering or colliding with other robotic arms, medical equipment, or medical personnel.

FIGS. 24A and 24B illustrate the impact on range of motion and minimum arm angle due to increasing the distance between the first motorized joint 1705A and the remote center. FIG. 24A depicts a first configuration 2400A of the robotic arm 1700 with the remote center 2405 located a first distance D1 from the first motorized joint 1705A along the yaw axis 1735A. In the first configuration 2400A, the robotic arm 1700 has a 40-degree minimum angle a1 between the insertion axis 1735B and the yaw axis 1735A with a 100-degree range of motion ROMi. FIG. 24B depicts a second configuration 2400B of the robotic arm 1700 with the remote center 2405 located a second distance D2 from the first motorized joint 1705A along the yaw axis 1735A, with the second distance D2 being greater than the first distance D1. In the second configuration 2400B, the robotic arm 1700 has a 25-degree minimum angle a2 between the insertion axis 1735B and the yaw axis 1735A with a 73-degree range of motion ROM2. This can help the robotic arm 1700 work closer to obstacles, for example other robotic arms, the patient bed, etc., without colliding with the obstacles. Though distances D1 and D2 are shown as being measured between the remote center 2405 and the cap of motorized joint 1705A, the distances can alternatively be measured between the remote center 2405 and any structure of the arm 1700 positioned along the first axis 1735A, for example the center of rotary joint 1705B.

Figure 25A:
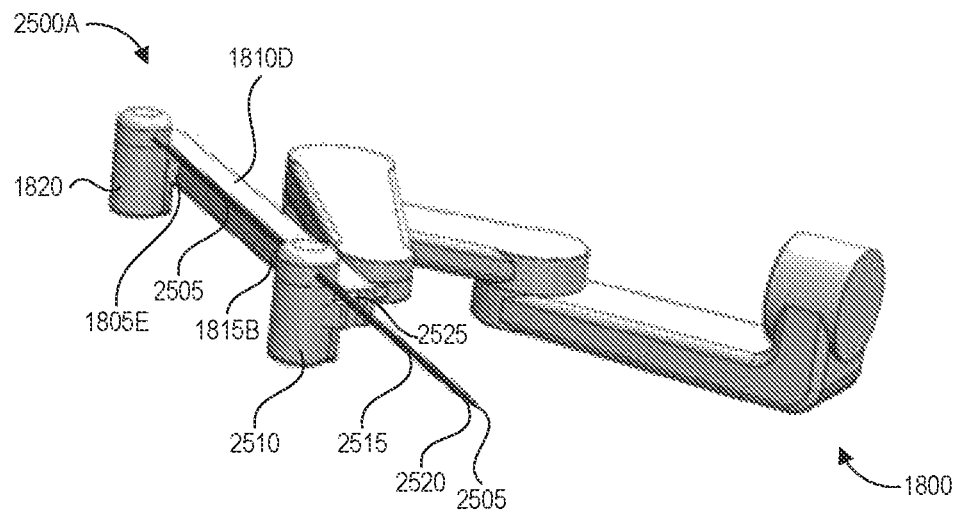
FIGS. 25A and 25B depict addition of a second instrument driver to the robotic arm of FIG. 18 during operation in the second mode depicted in FIG. 20A.
Figure 25B:
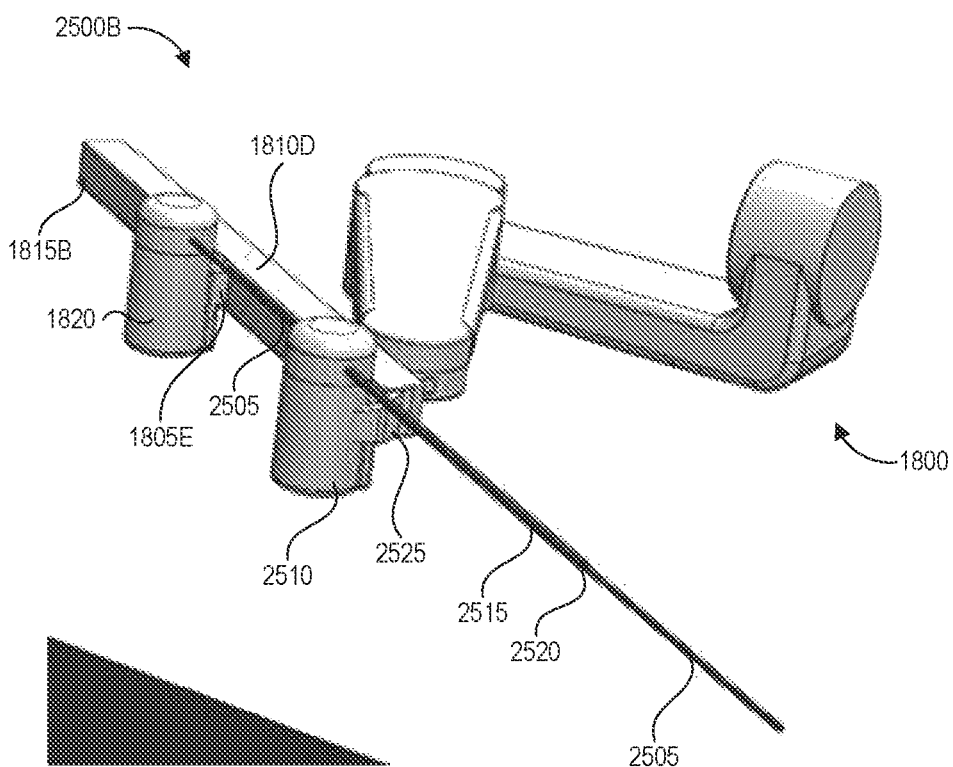

FIGS. 25A and 25B depict addition of a second instrument driver 2510 to the robotic arm 1800 of FIG. 18 during operation in the second mode 2000 depicted in FIG. 20A. As illustrated, the second instrument driver 2510 includes an attachment portion 2525 that secures to a docking port of the fourth linkage 1810D in place of the dock 1840. Addition of the second instrument driver 2510 allows the robotic arm 1800 to control first and second coaxial medical instruments 2505, 2515. System insertion of the medical instruments 2505, 2515 can be controlled with respect to a virtual rail defined along the axis of the first medical instrument 2505, for example.

As shown in FIG. 25A, the robotic arm 1800 can be positioned in a first configuration 2500A with the instrument driver 1820 positioned by the second motorized joint 1805E as far as possible from the second instrument driver 2510. As shown in FIG. 25B, the second motorized joint 1805E can be actuated along the distal surface 1815B of the fourth linkage 1810D to move the instrument driver 1820 towards the second instrument driver 2510. In the second configuration 2400B, this actuation advances the first medical instrument 2505 through the second medical instrument 2515 and farther beyond the end 2520 of the second medical instrument 2515 than in the configuration 2500A. The second motorized joint 1805E can continue to be actuated until the instrument driver 1820 is adjacent to the second instrument driver 2510, if desired to effect relative motion of the first and second medical instruments 2505, 2515.

FIG. 26 depicts the robotic arm 1800 of FIG. 18 in a storage configuration 2600. In the storage configuration 2600, the first, second, and third linkages 1810A-1810C are positioned in a stack in a substantially parallel fashion with the second linkage 1810B positioned between the first linkage 1810A and third linkage 1810C. The fourth linkage 1810D rests on the third linkage 1810C and is also substantially parallel to the other linkages 1810A-1810C. Substantially parallel refers to collapsing the arm as compact as possible with the proximal face of the fourth linkage 1810D resting against the third linkage 1810C and with the first, second, and third linkages 1810A-1810C positioned in the illustrated compact stack. The deviation from true parallel positioning depends upon the specific shapes of the linkages, which can be varied in some embodiments from the illustrated shapes. The storage configuration 2600 is possible due to the open kinematic chain of the robotic arm 1800, which allows breaking of the virtual link used during the first operational mode to provide for compact storage. This can be advantageous for a multi-arm system as shown in FIG. 20B, where some arms are not used in a particular procedure and can be stowed out of the way of the remaining arms and medical personnel, freeing up limited operating room space.

2. Additional Example Flexible Kinematic Chains

Figure 27:
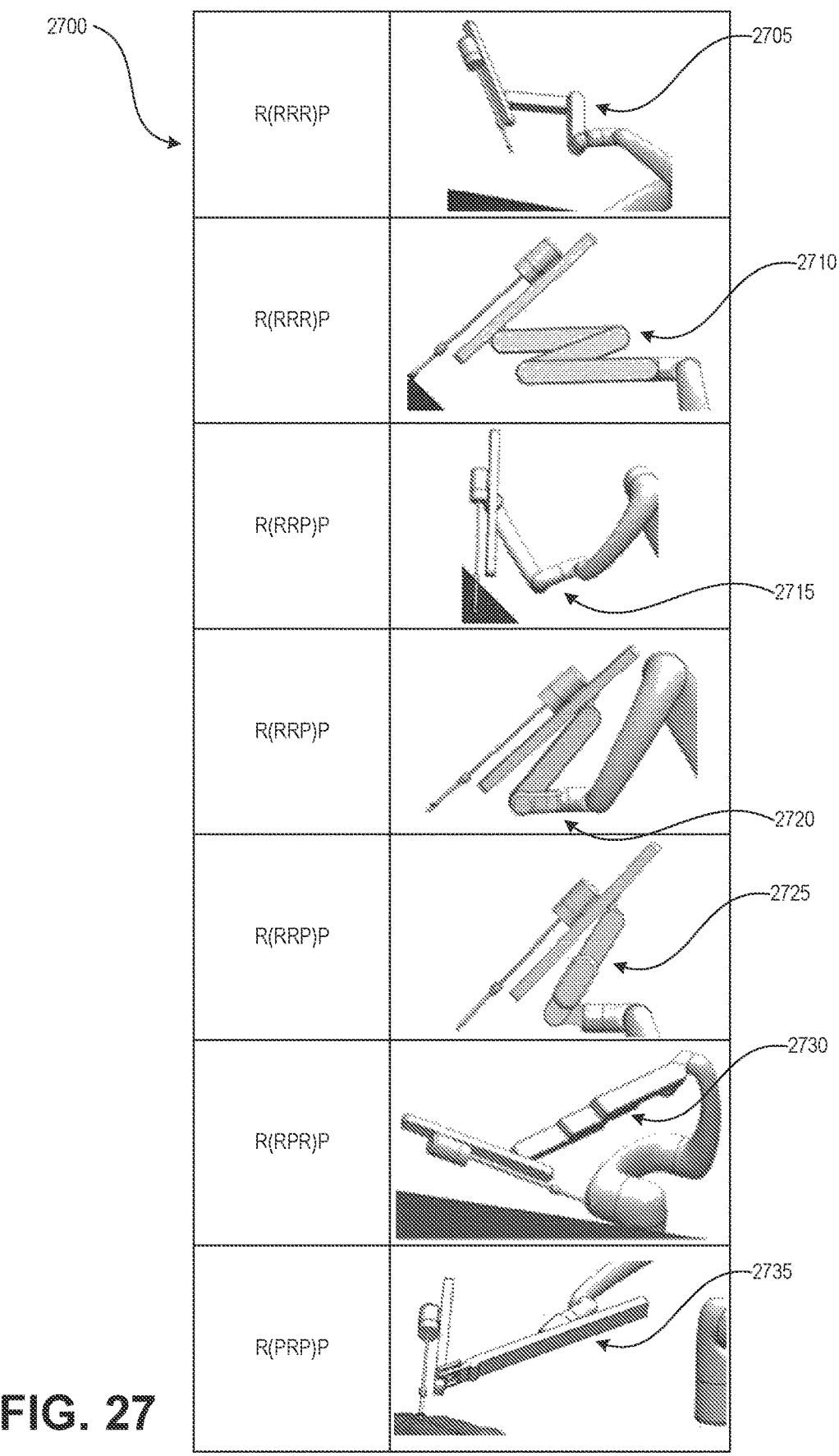
FIG. 27 depicts various examples of robotic arms according to the present disclosure.

FIG. 27 depicts a table 2700 showing various examples of robotic arms and their kinematic chains that can be operated in the various modes (e.g., 1900 and 2000) and sub-modes (e.g., 2200, 3200A-2300C, 2400A-2400B) or positioned in the various configurations (e.g., 2500A-2500B, 2600) of the present disclosure. The various illustrated arms are also depicted with setup arms that can be suitable for use with such arms, for example in a table-based, cart-based, or ceiling-based robotic system. As illustrated by the table, robotic arm 2705 is an embodiment of an RRRRP kinematic chain, robotic arm 2710 is another embodiment of an RRRRP kinematic chain, robotic arm 2715 is an embodiment of an RRRPP kinematic chain, robotic arm 2720 is another embodiment of an RRRPP kinematic chain, robotic arm 2725 is another embodiment of an RRRPP kinematic chain, robotic arm 2730 is an embodiment of an RRPRP kinematic chain, and robotic arm 2735 is an embodiment of an RPRPP kinematic chain. Each of these robotic arms is suitable for use in both the first operation mode 1900 and the second operating mode 2000 described herein.

Other configurations of the kinematic chain are also possible within the scope of the present disclosure. For example, if the design starts with a revolute joint at the proximal end of the robotic arm having a revolution axis capable of being pointed through a remote center and ends with a prismatic joint at the distal end of the robotic arm having a linear movement axis that is parallel to the tool insertion axis, the design provides a flexible R(XXX)P kinematic chain where the X's can be populated with either R or Ps to put together a series of joints that can perform a software constrained remote center as described herein. There are 8 categories of robotic arms that can satisfy the flexible R(XXX)P kinematic chain. Of these, R(PPP)P is not suitable for the first operating mode because at least one revolute is needed to create a remote pitch axis as described herein. There are various ways that each of the axes can be arranged and still have the same designation. For example, with respect to the R(RRP)P robotic arms 2715, 2720, and 2725, the last two prismatic axes are parallel to one another. However, in other embodiments these axes could also be configured to be at an angle to each other.

2. Overview of Operating Techniques

Figure 28:
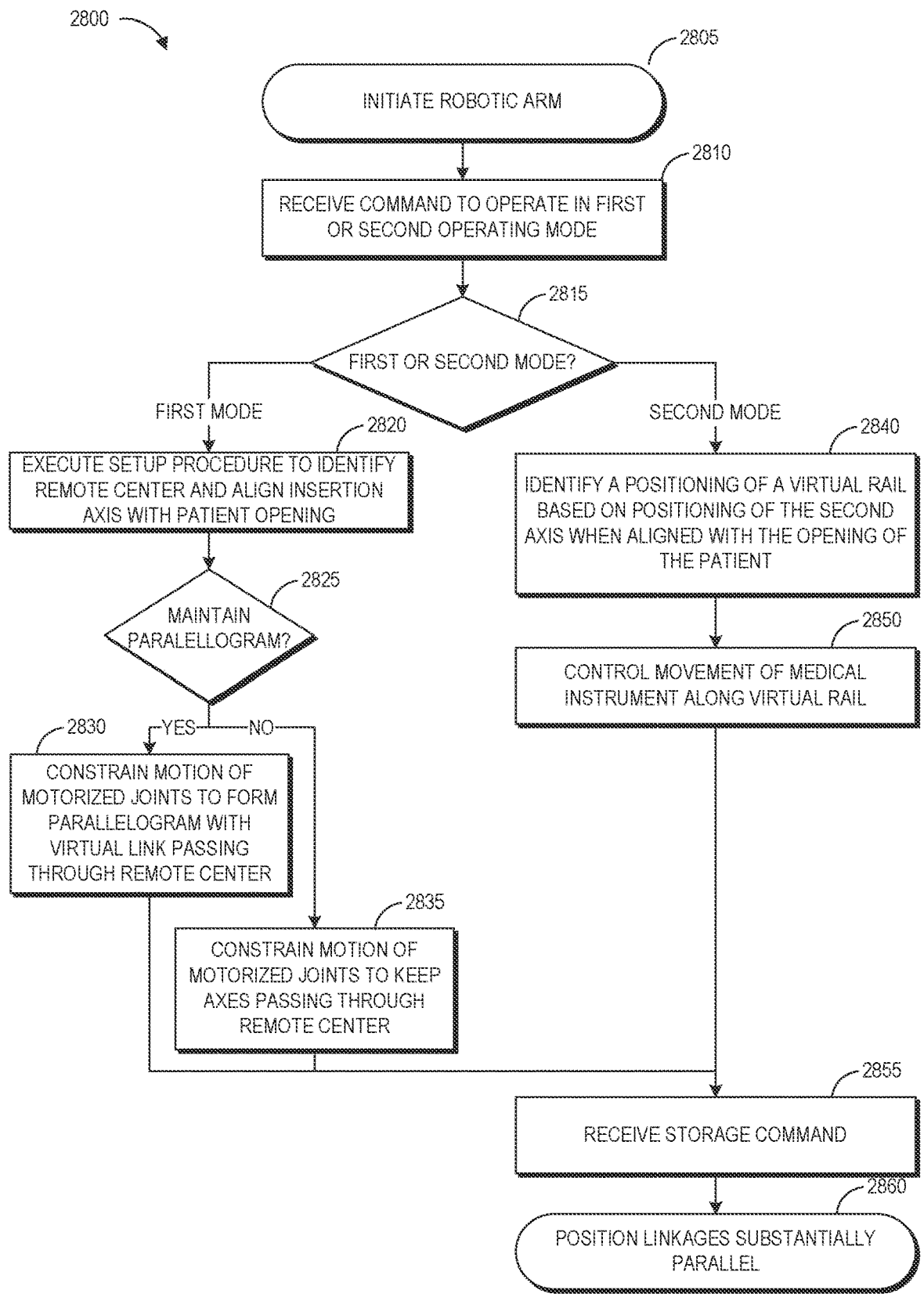
FIG. 28 depicts a flowchart of an example process for operating the robotic arms of FIGS. 17, 18, and 26.

FIG. 28 depicts a flowchart of an example process 2800 for operating the robotic arms 1700, 1800, 2705-2735 of FIGS. 17, 18, and 26. The process 2800 can be implemented wholly or partly by the controller 206 based on computer-executable instructions that control actuation of the motorized joints of the robotic arm, or may involve some motion imparted by human operators, as described below.

At block 2805, the controller 206 can initiate the robotic arm 1700, 1800, 2705-2735, for example by bringing it out of a storage configuration 2600 and/or by activating powered setup joints to position the robotic arm 1700, 1800, 2705-2735 near a patient or patient table.

At block 2810, the controller 206 can receive a command to operate the robotic arm 1700, 1800, 2705-2735 in either a first operating mode 1900 or a second operating mode 2000. At decision block 2815, the controller 206 can recognize the command and retrieve the appropriate operating instructions from a memory.

If the command is to operate the robotic arm 1700, 1800, 2705-2735 in the first operating mode 1900, the process 2800 transitions to block 2820 to execute a setup procedure. As shown in FIGS. 22A-22D, the setup procedure can involve (i) fixing a location of a remote center such that the second axis is aligned with an opening of a patient and passes through the remote center, and (ii) constraining the motion of the plurality of motorized joints when actuated in the first operating mode such that the second axis passes through the remote center. Fixing the location of the remote center can be accomplished based on docking the robotic arm 1700, 1800, 2705-2735 to a cannula and identifying the location as a point along or within the cannula. Block 2820 can involve one or more null space movements to align a yaw axis defined by the axis of revolution of a proximal revolute joint of the robotic arm 1700, 1800, 2705-2735 with the remote center, and creating a remote pitch axis that passes through the remote center.

At decision block 2825, the controller 206 can determine whether or not to maintain a parallelogram (or virtual parallelogram) in the configuration of the robotic arm 1700, 1800, 2705-2735 in the first operating mode 1900, as described with respect to FIGS. 23A-23B.

If so, the process 2800 transitions to block 2830 in which the controller 206 configures the robotic arm 1800, 2705 via null-space movements to form a parallelogram 2340A with a virtual link 2305A passing through the remote center 2225 and constrains actuation of the joints to maintain the parallelogram 2340A.

If not, the process 2800 transitions to block 2835 in which the controller 206 configures the robotic arm 1800, 2705 to form a broken parallelogram 2340B, 2340C and optionally to transition between a number of different broken parallelogram shapes while maintaining the position of the remote center 2225. The process 2800 may loop back to block 2825 intraoperatively after either of blocks 2830 and 2835 if the workspace or range of motion requirements for the robotic arm 1800, 2705 change.

For disclosed robotic arms such as robotic arm 1700 that may not be capable of forming a parallelogram (or virtual parallelogram), blocks 2825-2835 can instead involve the controller 206 determining a distance along the yaw axis 1735A between the remote center and the first motorized joint 1705A, as described with respect to FIGS. 24A and 24B.

If the command is to operate the robotic arm 1700, 1800, 2705-2735 in the second operating mode 2000, the process 2800 transitions to block 2840 to identify a positioning of a virtual rail based on positioning of the second axis when aligned with the opening of the patient. The second axis can be aligned with the patient opening by a user manually moving the robotic arm 1700, 1800, 2705-2735, by user control via command console 200, or by the controller 206.

At block 2850, the controller 206 controls movement of the medical instrument along the virtual rail. As described with respect to FIG. 20B, this can involve controlling movement of multiple medical instruments 1725A-1725C by multiple robotic arms 1700A-1700C along the virtual rail 2005. As described with respect to FIGS. 25A and 25B, this can involve controlling movement of multiple medical instruments 2505, 2515 by a single robotic arm 1800. In some embodiments, the robotic arms 1700A-1700C of FIG. 20B can be configured with additional instrument drivers as shown in FIGS. 25A and 25B. In some embodiments, the process 2800 can return to block 2840, for example if patient movement requires repositioning the virtual rail.

Blocks 2825-2835 for the first mode 1900 or block 2850 for the second mode 2000 can continue for the duration of a medical procedure. At block 2855, the controller 206 receives a storage command for some or all robotic arms of a robotic system. Accordingly, at block 2860 the controller 206 (or a user) can position the robotic arm 1800 in the storage configuration 2600 with the linkages positioned substantially parallel to one another. The other disclosed robotic arms 1700, 2705-2735 can have similar compact storage configurations and can be controlled to be positioned in such configurations manually or by the controller 206.

5. Alternatives

Several alternatives of the subject matter described herein are provided below.

Alternative 1. A robotic system configured to perform medical procedures, the system comprising: a robotic arm configured to control movement of a medical instrument with respect to at least first, second, and third axes, the robotic arm comprising a plurality of linkages serially coupling a plurality of motorized joints, the plurality of motorized joints including: a first motorized joint comprising a revolute joint, the first motorized joint configured to actuate the movement of the medical instrument about the first axis, a second motorized joint comprising a prismatic joint configured to linearly translate the medical instrument along the second axis, and a plurality of additional motorized joints positioned serially between the first and second motorized joints, the plurality of additional motorized joints configured to actuate the movement of the medical instrument about the third axis; at least one computer-readable memory having stored thereon executable instructions for operating the robotic system in one of a first and second operating modes; and at least one processor in communication with the at least one computer-readable memory and configured to execute the instructions to cause the system to at least: in response to receiving a command to operate in the first operating mode, (i) fix a location of a remote center such that the second axis is aligned with an opening of a patient and passes through the remote center, and (ii) constrain the motion of the plurality of motorized joints when actuated in the first operating mode such that the second axis passes through the remote center; and in response to receiving a command to operate in the second operating mode, (i) identify a positioning of a virtual rail based on positioning of the second axis when aligned with the opening of the patient, and (ii) control movement of the medical instrument along the virtual rail.

Alternative 2. The system of Alternative 1, wherein each of the plurality of motorized joints comprises its own motor.

Alternative 3. The system of Alternative 2, wherein each of the plurality of motorized joints further comprises a position sensor configured to determine a position of a rotor of the motor.

Alternative 4. The system of Alternative 3, wherein the at least one processor is configured to execute the instructions to cause the system to at least control positioning of the robotic arm in the first and second operating modes based at least partly on the position of the rotor of the motor of each of the plurality of motorized joints.

Alternative 5. The system of any one of Alternatives 1-4, wherein the at least one processor is configured to execute the instructions to cause the system to at least actuate the second motorized joint to move the medical instrument along the virtual rail.

Alternative 6. The system of any one of Alternatives 1-5, wherein the at least one processor is configured to execute the instructions to cause the system to at least coordinate actuation of two or more of the plurality of motorized joints to move the medical instrument along the virtual rail.

Alternative 7. The system of any one of Alternatives 1-6, wherein the plurality of additional motorized joints comprises third, fourth, and fifth joints.

Alternative 8. The system of Alternative 7, wherein, to constrain the motion of the plurality of motorized joints when actuated in the first operating mode, the at least one processor is configured to execute the instructions to cause the system to at least: identify a virtual orientation of a virtual linkage between the remote center and the third joint; and maintain positioning of a linkage of the plurality of linkages coupling the fourth and fifth joints parallel with the virtual orientation of the virtual linkage.

Alternative 9. The system of Alternative 8, wherein the at least one processor is configured to execute the instructions to cause the system to at least change a distance between the remote center and the third joint.

Alternative 10. The system of any one of Alternatives 8-9, the at least one processor is configured to execute the instructions to cause the system to at least fix a distance between the remote center and the third joint to be equal to a length of the linkage coupling the fourth and fifth joints.

Alternative 11. The system of any one of Alternatives 7-10, wherein each of the third, fourth, and fifth joints comprises an additional revolute joint.

Alternative 12. The system of Alternative 11, wherein a first linkage of the plurality of linkages couples the first and third joints, a second linkage of the plurality of linkages couples the third and fourth joints, and a first length of the first linkage is longer than a second length of the second linkage.

Alternative 13. The system of Alternative 12, wherein the at least one processor is configured to execute the instructions to cause the system to at least rotate the third and fourth joints such that the fourth joint passes from a first position on a first side of the first linkage past the first joint to a position on a second side of the first linkage.

Alternative 14. The system of any one of Alternatives 12-13, wherein a third linkage of the plurality of linkages couples the fourth and fifth joints, with the first, second, and third linkages being configured to be positioned in a substantially parallel fashion with the second linkage positioned between the first and third linkages.

Alternative 15. The system of Alternative 14, wherein the at least one processor is configured to position the first, second, and third linkages in the substantially parallel fashion in response to receiving a storage command.

Alternative 16. The system of any one of Alternatives 14-15, wherein a fourth linkage couples the second and fifth joints, the fourth linkage configured to be substantially parallel with and adjacent to the third linkage.

Alternative 17. The system of any one of Alternatives 7-16, wherein each of the third and fourth joints comprises first and second additional revolute joints and the fifth joint comprises an additional prismatic joint.

Alternative 18. The system of Alternative 17, wherein the additional prismatic joint is configured to move along an additional axis parallel to the second axis, wherein the at least one processor is configured to execute the instructions to cause the system to at least move the additional prismatic joint along the additional axis.

Alternative 19. The system of any one of Alternatives 1-18, further comprising an instrument driver coupled to the second motorized joint and configured to manipulate the medical instrument, wherein the at least one processor is configured to execute the instructions to cause the system to at least actuate the instrument driver to manipulate the medical instrument.

Alternative 20. The system of Alternative 19, wherein the instrument driver is aligned along the second axis.

Alternative 21. The system of Alternative 20, further comprising at least one additional robotic arm coupled to an additional instrument driver, wherein the at least one processor is configured to execute the instructions to cause the system to at least, in response to receiving the command to operate in the second operating mode, align the additional instrument driver along the virtual rail.

Alternative 22. The system of any one of Alternatives 19-21, wherein the first axis comprises a yaw axis, the second axis comprises an insertion axis, and the third axis comprises a pitch axis, wherein the at least one processor is configured to execute the instructions to cause the system to at least actuate the instrument driver to control movement of the medical instrument about a roll axis.

Alternative 23. The system of any one of Alternatives 19-22, further comprising a docking port coupled to an end of a linkage of the plurality of linkages with the second motorized joint configured to linearly move along the linkage, wherein the docking port is configured to couple to a cannula holder configured to retain a cannula inserted into the opening of the patient when the robotic arm is operated in the first operating mode, and wherein the docking port is configured to couple to an additional instrument driver when the robotic arm is operated in the second operating mode.

Alternative 24. The system of any one of Alternatives 1-23, further comprising a cannula holder coupled to a linkage of the plurality of linkages with the second motorized joint configured to linearly move along the linkage, wherein the at least one processor is configured to execute the instructions to cause the system to at least, in response to receiving the command to operate in the first operating mode: identify that a cannula is docked to the cannula holder; determine the location of the remote center based at least partly on a location of the cannula holder; and cause the robotic arm and at least one setup joint coupled to the robotic arm to perform at least one null-space movement to align the first axis to pass through the remote center, wherein during the null-space movement at least one joint of the plurality of motorized joints and the at least one setup joint is actuated and the location of the cannula holder remains fixed.

Alternative 25. The system of Alternative 24, wherein, after performing the at least one null-space movement, the at least one processor is configured to execute the instructions to cause the system to at least constrain the motion of the plurality of motorized joints in the first operating mode such that the first, second, and third axes pass through the remote center.

Alternative 26. The system of Alternative 25, wherein the at least one processor is configured to execute the instructions to cause the system to at least: receive a command to adjust a distance between the position of the first motorized joint and the location of the remote center; and perform at least one null-space movement to adjust the distance by actuating at least one joint from the plurality of additional motorized joints while maintaining alignment of the first, second, and third axes through the remote center.

Alternative 27. The system of any one of Alternatives 1-27, further comprising a setup joint coupled to the robotic arm, wherein a mechanical reach of the robotic arm extends throughout a workspace, and wherein the at least one processor is configured to execute the instructions to cause the system to at least actuate the setup joint to reposition the workspace of the robotic arm.

Alternative 28. The system of Alternative 27, wherein the at least one processor is configured to execute the instructions to cause the system to at least, in response to receiving the command to operate in the first operating mode, reposition the workspace of the robotic arm while performing null-space movement of the plurality of motorized joints such that the first, second, and third axes pass through the remote center.

Alternative 29. The system of any one of Alternatives 27-28, wherein the at least one processor is configured to execute the instructions to cause the system to at least, in response to receiving the command to operate in the second operating mode, reposition the workspace of the robotic arm while performing null-space movement of the plurality of motorized joints such that the second axis remains aligned with the opening of a patient.

Alternative 30. A non-transitory computer readable storage medium having stored thereon instructions that, when executed, cause at least one computing device to at least: receive a command to operate in one of a first operating mode and a second operating mode of controlling movement of a medical instrument with respect to at least first, second, and third axes via a robotic arm comprising a plurality of linkages serially coupling a plurality of motorized joints, the plurality of motorized joints including: a first motorized joint comprising a revolute joint, the first motorized joint configured to actuate the movement of the medical instrument about the first axis, a second motorized joint comprising a prismatic joint configured to linearly translate the medical instrument along the second axis, and a plurality of additional motorized joints positioned serially between the first and second motorized joints, the plurality of additional motorized joints configured to actuate the movement of the medical instrument about the third axis; in response to receiving the command to operate in the first operating mode, (i) fix a location of a remote center such that the second axis is aligned with an opening of a patient and passes through the remote center, and (ii) constrain the motion of the plurality of motorized joints when actuated in the first operating mode such that the such that the second axis passes through the remote center; and in response to receiving the command to operate in the second operating mode, align a virtual rail coaxial with the second axis with the opening of the patient.

Alternative 31. The non-transitory computer readable storage medium of Alternative 30, wherein each of the plurality of motorized joints comprises a motor having a rotor, and wherein the instructions, when executed, cause the at least one computing device to at least control positioning of the robotic arm in the first and second operating modes based at least partly on a position of the rotor of the motor of each of the plurality of motorized joints.

Alternative 32. The non-transitory computer readable storage medium of any one of Alternatives 30-31, wherein the instructions, when executed, cause the at least one computing device to at least, in response to receiving the command to operate in the second operating mode, (i) actuate at least some of the plurality of motorized joints to align the second axis with the opening of the patient, (ii) identify a positioning of a virtual rail based on positioning of the second axis when aligned with the opening of the patient, and (iii) control actuation of the medical instrument along the virtual rail.

Alternative 33. The non-transitory computer readable storage medium of any one of Alternatives 30-32, wherein the instructions, when executed, cause the at least one computing device to at least, in response to receiving the command to operate in the first operating mode: identify that a cannula is docked to a cannula holder coupled to a linkage of the plurality of linkages with the distal motorized joint configured to linearly move along the linkage; determine the location of the remote center based at least partly on a location of the cannula holder; and cause the robotic arm and at least one setup joint coupled to the robotic arm to perform at least one null-space movement to align the first axis to pass through the remote center, wherein during the null-space movement at least one joint of the plurality of motorized joints and the at least one setup joint is actuated and the location of the cannula holder remains fixed.

Alternative 34. The non-transitory computer readable storage medium of Alternative 33, wherein, after performing the at least one null-space movement, the instructions, when executed, cause the at least one computing device to at least constrain the motion of the plurality of motorized joints in the first operating mode such that the first, second, and third axes pass through the remote center.

Alternative 35. The non-transitory computer readable storage medium of Alternative 34, wherein the instructions, when executed, cause the at least one computing device to at least: receive a command to adjust a distance between the position of the first motorized joint and the location of the remote center; and perform at least one null-space movement to adjust the distance by actuating at least one of the plurality of motorized joints while maintaining alignment of the first, second, and third axes through the remote center.

Alternative 36. The non-transitory computer readable storage medium of any one of Alternatives 34-35, wherein the plurality of additional motorized joints comprises third, fourth, and fifth joints, and wherein the instructions to constrain the motion of the plurality of motorized joints when actuated in the first operating mode, when executed, cause the at least one computing device to at least: identify a virtual orientation of a virtual linkage between the remote center and the third joint; and maintain positioning of a linkage of the plurality of linkages coupling the fourth and fifth joints parallel with the virtual orientation of the virtual linkage.

Alternative 37. The non-transitory computer readable storage medium of any one of Alternatives 30-36, wherein a mechanical reach of the robotic arm extends throughout a workspace, and wherein the instructions, when executed, cause the at least one computing device to at least actuate a setup joint coupled to the robotic arm to reposition the workspace of the robotic arm.

Alternative 38. The non-transitory computer readable storage medium of Alternative 37, wherein the instructions, when executed, cause the at least one computing device to at least, in response to receiving the command to operate in the first operating mode, reposition the workspace of the robotic arm while performing at least one null-space movement of the plurality of motorized joints such that the first, second, and third axes pass through the remote center.

Alternative 39. The non-transitory computer readable storage medium of any one of Alternatives 37-38, wherein the instructions, when executed, cause the at least one computing device to at least, in response to receiving the command to operate in the second operating mode, reposition the workspace of the robotic arm while performing at least one null-space movement of the plurality of motorized joints such that the second axis remains aligned with the opening of a patient.

Alternative 40. The non-transitory computer readable storage medium of any one of Alternatives 30-39, wherein the instructions, when executed, cause the at least one computing device to at least, in response to receiving a storage command, position the plurality of linkages substantially parallel to one another.

Alternative 41. The non-transitory computer readable storage medium of any one of Alternatives 30-40, wherein the robotic arm further comprises an instrument driver coupled to the second motorized joint and configured to manipulate the medical instrument, wherein the instructions, when executed, cause the at least one computing device to at least actuate the instrument driver to manipulate the medical instrument.

Alternative 42. The non-transitory computer readable storage medium of Alternative 41, wherein the instructions, when executed, cause the at least one computing device to at least, in response to receiving the command to operate in the second operating mode: identify at least one additional robotic arm coupled to an additional instrument driver; and position the robotic arm and the additional robotic arm such that the instrument driver and additional instrument driver are aligned along the second axis.

Alternative 43. The non-transitory computer readable storage medium of any one of Alternatives 41-42, wherein the first axis comprises a yaw axis, the second axis comprises an insertion axis, and the third axis comprises a pitch axis, wherein the at least one processor is configured to execute the instructions to cause the system to at least actuate the instrument driver to control movement of the medical instrument about a roll axis.

Alternative 44. The non-transitory computer readable storage medium of any one of Alternatives 30-43, wherein one of the plurality of additional motorized joints positioned serially adjacent to the second motorized joint comprises an additional prismatic joint configured to move along an additional linear axis parallel to the second axis, and wherein the at least one processor is configured to execute the instructions to cause the system to at least move the additional prismatic joint along the additional linear axis.

Alternative 45. A method, comprising: receiving a command to operate in one of a first operating mode and a second operating mode of controlling movement of a medical instrument via a robotic arm comprising a plurality of linkages serially coupling a plurality of motorized joints, the plurality of motorized joints including: a first motorized joint comprising a revolute joint, the first motorized joint configured to rotate about a first axis, a second motorized joint comprising a prismatic joint configured to linearly translate the medical instrument along a second axis, and a plurality of additional motorized joints positioned serially between the first and second motorized joints, the plurality of additional motorized joints configured to actuate the movement of the medical instrument about a third axis; in response to receiving the command to operate in the first operating mode, (i) fixing a location of a remote center based on an opening of a patient, and (iii) constraining the motion of the plurality of motorized joints when actuated in the first operating mode such that the such that the second axis passes through the remote center; and in response to receiving the command to operate in the second operating mode, aligning a virtual rail coaxial with the second axis with the opening of the patient.

Alternative 46. The method of Alternative 45, performed programmatically by at least one computing device.

Alternative 47. The method of any one of Alternatives 45-46, wherein each of the plurality of motorized joints comprises a motor having a rotor, and wherein the method further comprises controlling positioning of the robotic arm in the first and second operating modes based at least partly on a position of the rotor of the motor of each of the plurality of motorized joints.

Alternative 48. The method of any one of Alternatives 45-46, further comprising, in response to receiving a command to operate in the second operating mode, (i) actuating at least some of the plurality of motorized joints to align the second axis with the opening of the patient, (ii) identifying a positioning of a virtual rail based on positioning of the second axis when aligned with the opening of the patient, and (iii) controlling actuation of the medical instrument along the virtual rail.

Alternative 49. The method of any one of Alternatives 45-46, further comprising, in response to receiving the command to operate in the first operating mode: identifying that a cannula is docked to a cannula holder coupled to a linkage of the plurality of linkages with the second motorized joint configured to linearly move along the linkage;

determining the location of the remote center based at least partly on a location of the cannula holder; and causing the robotic arm to perform at least one null-space movement to align the first axis to pass through the remote center, wherein during the null-space movement one or more of the plurality of motorized joints is actuated and the location of the cannula holder remains fixed.

Alternative 50. The method of Alternative 49, further comprising constraining the motion of the plurality of motorized joints in the first operating mode such that the first, second, and third axes pass through the remote center.

Alternative 51. The method of any one of Alternatives 45-50, wherein the plurality of additional motorized joints comprises third, fourth, and fifth joints, and wherein, to constrain the motion of the plurality of motorized joints when actuated in the first operating mode, the method further comprises: identifying a virtual orientation of a virtual linkage between the remote center and the third joint; and maintaining positioning of a linkage of the plurality of linkages coupling the fourth and fifth joints parallel with the virtual orientation of the virtual linkage.

Alternative 52. The method of Alternative 51, further comprising: receiving a command to adjust a distance between the position of the first motorized joint and the location of the remote center; and performing at least one null-space movement to adjust the distance by actuating at least one of the plurality of motorized joints while maintaining alignment of the first, second, and third axes through the remote center.

Alternative 53. The method of any one of Alternatives 45-52, wherein a mechanical reach of the robotic arm extends throughout a workspace, the method further comprising actuating a setup joint coupled to the robotic arm to reposition the workspace of the robotic arm.

Alternative 54. The method of Alternative 53, further comprising, in response to receiving the command to operate in the first operating mode, repositioning the workspace of the robotic arm while performing at least one null-space movement of the plurality of motorized joints such that the first, second, and third axes pass through the remote center.

Alternative 55. The method of any one of Alternatives 53-54, further comprising, in response to receiving the command to operate in the second operating mode, repositioning the workspace of the robotic arm while performing at least one null-space movement of the plurality of motorized joints such that the second axis remains aligned with the opening of a patient.

Alternative 56. The method of any one of Alternatives 45-55, further comprising: receiving a storage command for positioning of the robotic arm while not in use; and responsive to the storage command, positioning the plurality of linkages substantially parallel to one another.

Alternative 57. The method of any one of Alternatives 45-56, wherein the robotic arm further comprises an instrument driver coupled to the distal motorized joint and configured to manipulate the medical instrument, the method further comprising actuating the instrument driver to manipulate the medical instrument.

Alternative 58. The method of Alternative 57, further comprising, in response to receiving the command to operate in the second operating mode: identifying at least one additional robotic arm coupled to an additional instrument driver configured to manipulate an additional medical instrument; and positioning the robotic arm and the additional robotic arm such that the instrument driver and additional instrument driver are aligned along the second axis.

Alternative 59. The method of any one of Alternatives 57-58, wherein the first axis comprises a yaw axis, the second axis comprises an insertion axis, and the third axis comprises a pitch axis, the method further comprising actuating the instrument driver to control movement of the medical instrument about a roll axis.

Alternative 60. The method of any one of Alternatives 45-59, wherein one of the plurality of additional motorized joints positioned serially adjacent to the distal motorized joint comprises an additional prismatic joint configured to move along an additional linear axis parallel to the second axis, the method further comprising moving the additional prismatic joint along the additional linear axis.

Alternative 61. A robotic system configured to perform medical procedures, the system comprising: a robotic arm configured to control movement of a medical instrument with respect to at least first, second, and third axes, the robotic arm comprising a plurality of linkages serially coupling a plurality of motorized joints, the plurality of motorized joints including: a first motorized joint comprising a revolute joint, the first motorized joint configured to actuate the movement of the medical instrument about the first axis, a second motorized joint comprising a prismatic joint configured to linearly translate the medical instrument along the second axis, and a plurality of additional motorized joints positioned serially between the first and second motorized joints, the plurality of additional motorized joints configured to actuate the movement of the medical instrument about the third axis; at least one computer-readable memory having stored thereon executable instructions for operating the robotic system; and at least one processor in communication with the at least one computer-readable memory and configured to execute the instructions to cause the system to at least: fix a location of a remote center relative to an opening of a patient, and constrain the motion of the plurality of motorized joints when actuated such that the second axis passes through the remote center.

Alternative 62. The system of Alternative 61, wherein each of the plurality of motorized joints comprises its own motor.

Alternative 63. The system of Alternative 62, wherein each of the plurality of motorized joints further comprises a position sensor configured to determine a position of a rotor of the motor.

Alternative 64. The system of Alternative 63, wherein the at least one processor is configured to execute the instructions to cause the system to at least control positioning of the robotic arm based at least partly on the position of the rotor of the motor of each of the plurality of motorized joints.

Alternative 65. The system of any one of Alternatives 61-64, wherein the plurality of additional motorized joints comprises third, fourth, and fifth joints.

Alternative 66. The system of Alternative 65, wherein each of the third, fourth, and fifth joints comprises an additional revolute joint.

Alternative 67. The system of Alternative 66, wherein a first linkage of the plurality of linkages couples the first and third joints, a second linkage of the plurality of linkages couples the third and fourth joints, and a first length of the first linkage is longer than a second length of the second linkage.

Alternative 68. The system of Alternative 67, wherein the at least one processor is configured to execute the instructions to cause the system to at least rotate the third and fourth joints such that the fourth joint passes from a first position on a first side of the first linkage past the first joint to a position on a second side of the first linkage.

Alternative 69. The system of any one of Alternatives 67-68, wherein a third linkage of the plurality of linkages couples the fourth and fifth joints, the first, second, and third linkages being configured to be positioned in a substantially parallel fashion with the second linkage positioned between the first and third linkages.

Alternative 70. The system of Alternative 69, wherein a fourth linkage couples the second and fifth joints, the fourth linkage configured to be substantially parallel with and adjacent to the third linkage.

Alternative 71. The system of any one of Alternatives 65-70, wherein each of the third and fourth joints comprises first and second additional revolute joints and the fifth joint comprises an additional prismatic joint.

Alternative 72. The system of Alternative 71, wherein the additional prismatic joint is configured to move along an additional axis parallel to the second axis, wherein the at least one processor is configured to execute the instructions to cause the system to at least move the additional prismatic joint along the additional axis.

Alternative 73. The system of any one of Alternatives 61-72, further comprising an instrument driver coupled to the second motorized joint and configured to manipulate the medical instrument, wherein the at least one processor is configured to execute the instructions to cause the system to at least actuate the instrument driver to manipulate the medical instrument.

Alternative 74. The system of Alternative 73, wherein the instrument driver is aligned along the second axis.

Alternative 75. The system of any one of Alternatives 73-74, wherein the first axis comprises a yaw axis, the second axis comprises an insertion axis, and the third axis comprises a pitch axis, wherein the at least one processor is configured to execute the instructions to cause the system to at least actuate the instrument driver to control movement of the medical instrument about a roll axis.

Alternative 76. The system of any one of Alternatives 61-75, further comprising a cannula holder coupled to a linkage of the plurality of linkages with the second motorized joint configured to linearly move along the linkage, wherein the at least one processor is configured to execute the instructions to cause the system to at least: identify that a cannula is docked to the cannula holder; determine the location of the remote center based at least partly on a location of the cannula holder; and cause the robotic arm and at least one setup joint coupled to the robotic arm to perform at least one null-space movement to align the first axis to pass through the remote center, wherein during the null-space movement at least one joint of the plurality of motorized joints and the at least one setup joint is actuated and the location of the cannula holder remains fixed.

Alternative 77. The system of Alternative 76, wherein, after performing the at least one null-space movement, the at least one processor is configured to execute the instructions to cause the system to at least constrain the motion of the plurality of motorized joints such that the first, second, and third axes pass through the remote center.

Alternative 78. The system of any one of Alternatives 76-77, further comprising a motorized setup joints coupled to the robotic arm, wherein the at least one processor is configured to execute the instructions to cause the system to at actuate the motorized setup joint to perform the null-space movement.

Alternative 79. The system of any one of Alternatives 76-78, wherein each of the third, fourth, and fifth joints comprises an additional revolute joint, and wherein, to constrain the motion of the plurality of motorized joints after performing the at least one null-space movement, the at least one processor is configured to execute the instructions to cause the system to at least: identify a virtual orientation of a virtual linkage between the remote center and the third joint; and maintain positioning of a linkage of the plurality of linkages coupling the fourth and fifth joints parallel with the virtual orientation of the virtual linkage.

Alternative 80. The system of Alternative 79, wherein the at least one processor is configured to execute the instructions to cause the system to at least change a distance between the remote center and the third joint.

Alternative 81. The system of any one of Alternatives 79-80, the at least one processor is configured to execute the instructions to cause the system to at least fix a distance between the remote center and the third joint to be equal to a length of the linkage coupling the fourth and fifth joints.

Alternative 82. The system of Claim any one of Alternatives 76-81, wherein the at least one processor is configured to execute the instructions to cause the system to at least: receive a command to adjust a distance between the position of the first motorized joint and the location of the remote center; and perform at least one null-space movement to adjust the distance by actuating at least one joint from the plurality of additional motorized joints while maintaining alignment of the first, second, and third axes through the remote center.

Alternative 83. The system of any one of Alternatives 61-82, further comprising a setup joint coupled to the robotic arm, wherein a mechanical reach of the robotic arm extends throughout a workspace, and wherein the at least one processor is configured to execute the instructions to cause the system to at least actuate the setup joint to reposition the workspace of the robotic arm.

Alternative 84. The system of Alternative 83, wherein the at least one processor is configured to execute the instructions to cause the system to at least reposition the workspace of the robotic arm while performing null-space movement of the plurality of motorized joints such that the first, second, and third axes pass through the remote center.

Alternative 85. The system of any one of Alternatives 83-84, wherein the at least one processor is configured to execute the instructions to cause the system to at least reposition the workspace of the robotic arm while performing null-space movement of the plurality of motorized joints such that the second axis remains aligned with the opening of a patient.

6. Implementing Systems and Terminology

Implementations disclosed herein provide systems, methods and apparatus for convertible medical robotic systems that leverage a versatile, open kinematic chain together with a set of medical-procedure-specific software-controlled actuation constraints in order to perform a variety of medical procedures.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The various functions for controlling actuation of the robotic arms described herein according to the disclosed operational modes may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system for robotic manipulation of a medical instrument, comprising:
   at least one robotic arm comprising a plurality of motors configured to cooperate to move a medical instrument, a first motor of the plurality of motors configured to rotate the medical instrument about a first axis, and a second motor of the plurality of motors configured to translate the medical instrument along a second axis, wherein the robotic arm is coupled to an elongated shaft coaxial with the second axis and adapted to deploy through a body opening of a patient; and
   a control unit configured to:
      cause the at least one robotic arm to align the elongated shaft such that the elongated shaft passes through the body opening;
      determine a remote center location that corresponds to an intersection between the elongated shaft and the body opening;
      constrain the at least one robotic arm so that the second axis is fixed through the remote center location while the at least one robotic arm manipulates the medical instrument;
      cause the at least one robotic arm to align the first axis to pass through the remote center location while being constrained with the second axis fixed through the remote center location; and
      relax the constraint on the at least one robotic arm to facilitate docking of the at least one robotic arm to a cannula and, subsequent to the docking, reinstate the constraint on the at least one robotic arm.

2. The system of claim 1, wherein causing the at least one robotic arm to align the first axis to pass through the remote center location while being constrained with the second axis fixed through the remote center location comprises causing the at least one robotic arm to perform a null-space movement in which the elongated shaft remains fixed.

3. The system of claim 1, wherein the first axis is a yaw axis of the medical instrument with respect to the remote center location and the second axis is an insertion axis through the remote center location.

4. The system of claim 3, wherein the control unit is further configured to:
   determine a third axis fixed in space and passing through the remote center location; and
   cause the at least one robotic arm to pitch the medical instrument with respect to the remote center location along the third axis while being constrained with the insertion axis fixed through the remote center location.

5. The system of claim 4, wherein the control unit is further configured to cause the at least one robotic arm to adjust a distance between a position of the first motor and the remote center location while maintaining alignment of the first axis, the second axis, and the third axis through the remote center location.

6. The system of claim 4, wherein the control unit is further configured to actuate at least one additional motor while maintaining alignment of the first axis, the second axis, and the third axis through the remote center location.

7. The system of claim 3, wherein the control unit is further configured to:
   determine a pitch axis fixed in space and passing through the remote center location; and
   cause the at least one robotic arm to insert, pitch, and yaw the medical instrument with respect to the remote center location.

8. The system of claim 1, wherein the control unit is further configured to activate the first motor to impart linear motion to the medical instrument along the second axis and through the remote center location and body opening.

9. The system of claim 1, further comprising:
   a first robotic arm comprising a first instrument driver at a distal end of the first robotic arm; and
   a second robotic arm comprising a second instrument driver at a distal end of the second robotic arm,
   wherein a proximal portion of the medical instrument is operably coupled to the first instrument driver and a distal portion of the medical instrument is operably coupled to the second instrument driver,
   wherein the control unit is further configured to:
      cause the first and second robotic arms to coaxially align the proximal portion and the distal portion of the medical instrument to create a virtual rail passing through the remote center location;
reposition the virtual rail in space by manipulating at least one of the first and second robotic arms into a different position; and
translate the first and second instrument drivers along the virtual rail to cause an inner telescoping portion of the medical instrument to telescope relative to an outer portion of the medical instrument or to advance or retract with respect to the body opening.

10. The system of claim 1, wherein the plurality of motors comprises an instrument driver, wherein the control unit is further configured to actuate the instrument driver to roll the medical instrument around the second axis.

11. The system of claim 1, wherein the plurality of motors comprises an instrument driver, wherein the control unit is further configured to:
determine a virtual location of a distal tip of the medical instrument; and
actuate the instrument driver to cause a deflection of the distal tip while maintaining alignment of the first axis and the second axis through the remote center location.

12. The system of claim 1, wherein the at least one robotic arm comprises a plurality of linkages, wherein the plurality of motors comprises a motorized joint, and wherein the control unit is further configured to:
identify an orientation of a virtual link defined between the remote center location and the motorized joint, and an orientation of a respective linkage of the plurality of linkages; and
adjust a position of the at least one robotic arm such that the virtual link and the respective linkage are parallel to each other.

13. The system of claim 12, wherein the control unit is further configured to cause the at least one robotic arm to form a parallelogram based on a positioning of at least two of the plurality of linkages, an orientation of the elongated shaft, and the virtual link defined between the remote center location and the motorized joint.

14. The system of claim 1, wherein the at least one robotic arm is operating in a first mode when the at least one robotic arm is constrained with the second axis fixed through the remote center location, and wherein the control unit is further configured to switch to a second mode in which the at least one robotic arm is no longer constrained to maintain the second axis fixed through the remote center location.

15. The system of claim 1, wherein the at least one robotic arm comprises a first robotic arm, and the first motor comprises a first motorized joint of the first robotic arm, and the second motor comprises a second motorized joint of the first robotic arm.

16. The system of claim 15, wherein the first and second motorized joints each comprise a position sensor configured to determine a position of the motorized joint, wherein causing the at least one robotic arm to align the elongated shaft and to align the first axis comprises positioning the first robotic arm based at least partly on the determined position of the first and second motorized joints.

17. A machine-implemented method for robotic manipulation of a medical instrument, comprising:
robotically facilitating movement of at least one robotic arm comprising a plurality of motors configured to cooperate to move a medical instrument, a first motor of the plurality of motors configured to rotate the medical instrument about a first axis, and a second motor of the plurality of motors configured to translate the medical instrument along a second axis, wherein the robotic arm is coupled to an elongated shaft coaxial with the first second axis and adapted to deploy through a body opening of a patient;
causing the at least one robotic arm to align the elongated shaft such that the elongated shaft passes through the body opening;
determining a remote center location that corresponds to an intersection between the elongated shaft and the body opening;
constraining the at least one robotic arm so that the second axis is fixed through the remote center location while the at least one robotic arm manipulates the medical instrument;
causing the at least one robotic arm to align the first axis to pass through the remote center location while being constrained with the second axis fixed through the remote center location;
relaxing the constraint on the at least one robotic arm to facilitate docking of the at least one robotic arm to a cannula; and
subsequent to the docking, reinstating the constraint on the at least one robotic arm.

18. The machine-implemented method of claim 17, wherein causing the at least one robotic arm to align the first axis to pass through the remote center location while being constrained with the second axis fixed through the remote center location comprises causing the at least one robotic arm to perform a null-space movement in which the elongated shaft remains fixed.

19. The machine-implemented method of claim 17, further comprising:
coupling first and second robotic arms to respective proximal and distal portions of the medical instrument;
causing first and second robotic arms to coaxially align the proximal and distal portions of the medical instrument with the remote center location to create a virtual rail passing through the remote center location;
repositioning the virtual rail in space by manipulating at least one of the first and second robotic arms into a different position; and
translating distal ends of the first and second robotic arms along the virtual rail to cause an inner telescoping portion of the medical instrument to telescope relative to an outer portion of the medical instrument or to advance or to retract with respect to the body opening.

20. A non-transitory machine-readable medium comprising instructions stored thereon that, when executed by a control unit, causes the control unit to perform operations, comprising:
robotically facilitating movement of at least one robotic arm comprising a plurality of motors configured to cooperate to move a medical instrument, a first motor of the plurality of motors configured to rotate the medical instrument about a first axis, and a second motor of the plurality of motors configured to translate the medical instrument along a second axis, wherein the robotic arm is coupled to an elongated shaft coaxial with the second axis and adapted to deploy through a body opening of a patient;
causing the at least one robotic arm to align the elongated shaft such that the elongated shaft passes through the body opening;
determining a remote center location that corresponds to an intersection between the elongated shaft and the body opening;

constraining the at least one robotic arm so that the second axis is fixed through the remote center location while the at least one robotic arm manipulates the medical instrument;

causing the at least one robotic arm to align the first axis to pass through the remote center location while being constrained with the second axis fixed through the remote center location;

relaxing the constraint on the at least one robotic arm to facilitate docking of the at least one robotic arm to a cannula; and subsequent to the docking, reinstating the constraint on the at least one robotic arm.

21. The system of claim 1, wherein the control unit is configured to cause the at least one robotic arm to form a broken parallelogram based on a positioning of a first linkage of the at least one robotic arm, a second linkage of the at least one robotic arm, an orientation of the elongated shaft, and a virtual link defined between the remote center location and a motorized joint of the at least one robotic arm, the virtual link parallel to the second linkage and having a different length than the second linkage.

22. The machine-implemented method of claim 17, further comprising causing the at least one robotic arm to form a broken parallelogram based on a positioning of a first linkage of the at least one robotic arm, a second linkage of the at least one robotic arm, an orientation of the elongated shaft, and a virtual link defined between the remote center location and a motorized joint of the at least one robotic arm, the virtual link parallel to the second linkage and having a different length than the second linkage.

23. The non-transitory machine-readable medium of claim 20, wherein the instructions, when executed by the control unit, cause the control unit to:

cause the at least one robotic arm to form a broken parallelogram based on a positioning of a first linkage of the at least one robotic arm, a second linkage of the at least one robotic arm, an orientation of the elongated shaft, and a virtual link defined between the remote center location and a motorized joint of the at least one robotic arm, the virtual link parallel to the second linkage and having a different length than the second linkage.

* * * * *